United States Patent [19]

Belleau et al.

[11] 4,065,623
[45] Dec. 27, 1977

[54] O-2-ISOCEPHEM-4-CARBOXYLIC ACID DERIVATIVES AS ANTIBACTERIAL AGENTS

[75] Inventors: Bernard R. Belleau, Westmont, Canada; Terrence W. Doyle, Fayetteville, N.Y.; Bing Yu Luh; Terry T. Conway, both of Brossard, Canada

[73] Assignee: Bristol-Myers Company, New York, N.Y.

[21] Appl. No.: 715,944

[22] Filed: Aug. 19, 1976

Related U.S. Application Data

[62] Division of Ser. No. 538,271, Jan. 2, 1975, Pat. No. 4,012,383.

[51] Int. Cl.$^2$ .................................... C07D 265/34
[52] U.S. Cl. ............................................ 544/105
[58] Field of Search .................................. 260/244

[56] References Cited

U.S. PATENT DOCUMENTS 3,835,130  9/1974  Woodward ............... 260/243 C

FOREIGN PATENT DOCUMENTS 2,046,822  3/1972  Germany.
2,046,823  3/1972  Germany.
2,046,824  3/1972  Germany.
2,355,209  3/1974  Germany.
1,377,715  12/1974  United Kingdom.

OTHER PUBLICATIONS

Brunwin et al, J. Chem. Soc. Chem. Comm., 865-867 (1971).
Brunwin et al, J. Chem. Soc. Chem. Comm., 589-590 (1972).
Brunwin et al, J. Chem. Soc. (c) 3756-3762 (1971).
Wolfe et al, Can. J. Chem., 50, 2895-2905 (1972).
Kukolja, J.A.C.S. 93, 6267-6270 (1971).
Kukolja, J.A.C.S. 94, 7590-7593 (1972).
Lowe, et al, J. Chem. Soc. Perkins I, 1321-1328 (1973).
Luttringer et al, Tetrahedron Letters, 4163-4166 (1973).
Sheehan et al, J. Heterocycl. Chem., 5, 779-783 (1968).
Mukerjee et al, Synthesis, 327-346 (1973).

*Primary Examiner*—Jane S. Myers
*Attorney, Agent, or Firm*—David M. Morse

[57] ABSTRACT

There is described the stereoselective total synthesis by a variety of routes of novel suitably substituted $\Delta^{2,3}$-1,4-morpholine-2-carboxylic acids possessing a fused $\beta$-lactam ring in the 1,6-position and carrying a substituent cis to carbon 5 in the 7-position of the fused ring system represented by the general formula

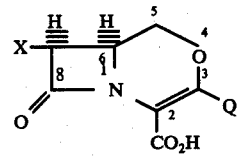

wherein Q is hydrogen, alkyl, aralkyl or $-CH_2COOZ$ where Z is hydrogen or the residue of an ester group and X is amino, azido or acylamino. Also included in the invention are compounds of the above formula in which the carboxyl group at the 2-position is protected as by an easily cleavable ester group and salts of both the free acids and carboxyl-protected compounds. Those compounds in which X is acylamino and their physiologically hydrolyzed esters and pharmaceutically acceptable salts are potent antibacterial agents.

12 Claims, No Drawings

O-2-ISOCEPHEM-4-CARBOXYLIC ACID DERIVATIVES AS ANTIBACTERIAL AGENTS

CROSS-REFERENCE TO RELATED APPLICATION

This is a divisional application of co-pending application Ser. No. 538,271 filed Jan. 2, 1975 now U.S. Pat. No. 4,012,383.

BACKGROUND OF THE INVENTION

1. Field of the Invention

The chemical processes of the present invention produce novel antibacterial agents of the β-lactam type containing a hitherto unknown nucleus and useful intermediates for their synthesis.

2. Description of the Prior Art

Penicillins and cephalosporins comprise a group of well-known antibacterial agents commonly grouped together as a class called β-lactam antibiotics. For a recent review of this field with many citations (especially the first ten) to the prior work, see J. P. Hou and J. W. Poole, β-lactam Antibiotics: Their Physicochemical Properties and Biological Activities in Relation to Structure, J. Pharmaceutical Sciences, 60(4), 503-532 (Apr. 1971). Most of the work in this field has fundamentally been done, speaking broadly, with 6-aminopenicillanic acid, 7-aminocephalosporanic acid and derivatives thereof produced by fermentation or chemical transformation of the natural products. Despite the extensive progress made in preparing active derivatives of 6-aminopenicillanic acid and 7-aminocephalosporanic acid, there is a continuing search for synthetic and semi-synthetic routes to new families of β-lactam antibiotics which may possess more advantageous properties then those derived from the known penicillin and cephalosporin nuclei.

Considerable work has been done on total chemical synthesis of both known β-lactams and nuclear analogs of such known compounds. A recent review is the text by M. S. Manhas and A. K. Bose, Synthesis of Penicillin, Cephalosporin C and Analogues, Marcel Decker, Inc., 95 Madison Avenue, New York, New York, 1969. Another extensive review is by R. B. Morin and B. G. Jackson, Chemistry of Cephalosporin Antibiotics, Fortschr. Chem. Org. Naturst., 28, 343-403 (1970), especially pages 379-393; the now famous "Woodward Intermediate" is shown therein as compound 146 on page 387. A more recent review of β-lactams is that by M. S. Manhas and A. K. Bose, Beta-Lactams: Natural and Synthetic: Part 1, Wiley-Interscience, New York, New York, 1971. A still further review article on the synthesis of β-lactams is that by A. K. Mukerjee et al., Synthesis, 327 (1973).

Other pertinent publications relating to synthesis of β-lactams are:

a. D. M. Brunwin, G. Lowe and J. Parker, J.C.S. Chem. Comm., 1971, 865-867, describing synthesis of nuclear analogs of the penicillin-cephalosporin group.

b. D. M. Brunwin et al., J. Chem. Soc. (C), 1971, 3756-3762 and J.C.S. Chem. Comm., 1972, 589-590 describing total synthesis of nuclear analogs of penicillins and cephalosporins.

c. S. Kukolja, J. Amer. Chem. Soc., 93, 6267-6270 (1971) and 94, 7590-7593 (1972) describing preparation of 6-phthalimido-5-epipenicillanates and disulfide analogs of penicillins.

d. J. A. Webber et al., J. Medicinal Chemistry, 14(11), 1136-1138 (1971) describing preparation of 3-cyanomethyl cephem nucleus.

e. West German Patent Specification No. 2,219,601 (Farmdoc 76,051T) describing synthesis of β-lactams of the formula

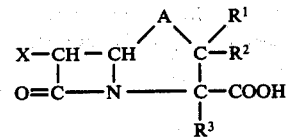

wherein X is halo, $N_3$— or $H_2N$—, A is —S—, —S—$CH_2$—, —O—, —O—$CH_2$—, —$CH_2$, —$CH_2CH_2$— or —NH— and $R^1$, $R^2$ and $R^3$ are hydrogen, $C_1$-$C_6$ alkyl or aryl.

f. U.K. Pat. No. 1,308,822 disclosing β-lactams of the formula

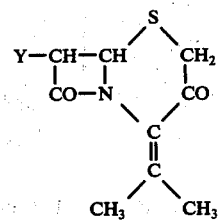

where Y = amino or substituted amino.

g. S. Wolfe et al., Can. J. Chem., 50, 2894-2905 (1972) describing synthesis of sulfur-free penicillin derivatives.

h. French Patent 2,111,859 describing nuclei of the formula

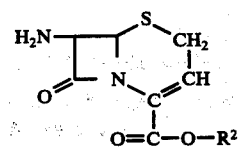

and 7-acylated derivatives thereof.

i. Helvetica Chimica Acta, 55(2), 388-429 (1972) describing nuclear modified cephalosporins and penicillins.

j. F. Moll et al., Zeit. fur Naturforsch. B, 27(b)6, 727 (1972) describing nuclear analogs of cephalosporins.

k. U.K. Specifications 1,271,013 and 1,271,014 describing γ-lactams of 7-(acylamino)-3-aminomethyl-ceph-3-em-4-carboxylic acids.

l. U.K. Pat. Specification No. 1,271,180 describing preparation of novel thiazoline azetidinone rearrangement products useful as intermediates in penicillin and cephalosporin synthesis.

m. German Patent Specifications Nos. 2,046,822, 2,046,823 and 2,046,824 describing synthesis of novel azetidinone intermediates.

n. G. Lowe et al., J. Chem. Soc. Perkins I, 1322 (1973) describing total synthesis of nuclear analogs of 7-methylcephalosporins having the formula o. D. M. Brunwin et al., J. Chem. Soc. Chem. Comm., 865 (1971) describing synthesis of compounds of the formula

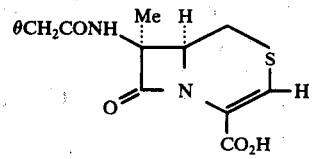

p. S. Wolfe et al., Canadian J. Chem., 50, 2902 (1972) describing compounds of the formula

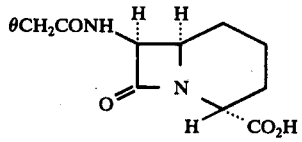

q. J. P. Luttringer et al., Tetrahedron Letters, 4163–4166 (1973) describing compounds of the formula

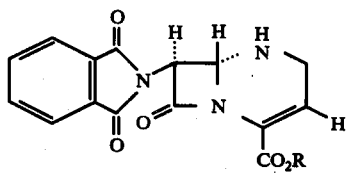

SUMMARY OF THE INVENTION

The present invention provides stereoselective total synthesis of certain novel substituted $\Delta^{2,3}$-1,4-morpholine-2-carboxylic acids possessing a fused $\beta$-lactam ring in the 1,6-position and carrying a substituent cis to carbon 5 in the 7-position of the fused ring system represented by the general formula

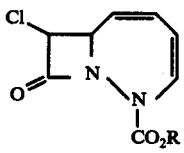

wherein Q is hydrogen, alkyl, aralkyl or —CH$_2$COOZ where Z is hydrogen or the residue of an ester group and X is azido, amino or acylamino. When X is acylamino, these acids (and their pharmaceutically acceptable salts and physiologically hydrolyzed esters) are potent antibacterial agents.

Also included in this invention are various novel intermediates useful in preparing the active $\beta$-lactam derivatives described above and various processes for the production of the intermediates and active compounds.

The compounds having the above general formula represent a new family of $\beta$-lactam antibiotics. They can be considered nuclear analogs of cephalosporins in which the sulphur atom of the dihydrothiazine ring is replaced by an oxygen atom and shifted from position 5 to position 4 of the $\beta$-lactam ring system as numbered in the formula above. The nomenclature to be used could be the following:

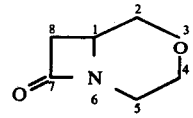

3-oxa-6-aza-bicyclo-[4,2,0]octan-7-one.

However, Sheehan has used the term O-cephem for the structure

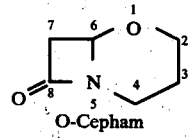

[J.C. Sheehan and M. Dadic, J. Heterocyclic Chem., 5, 770 (1968)] and we propose the use of the term 0-2-isocepham for the basic system having the formula

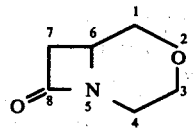

The numerical prefix indicates the position of the hetero-atom.

To illustrate the above system, the intermediate of the formula

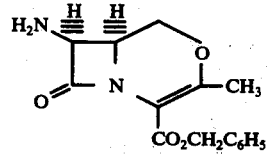

may be named benzyl 7$\beta$-amino-3-methyl-$\Delta^3$-0-2-isocephem-4-carboxylate and the compound of the formula

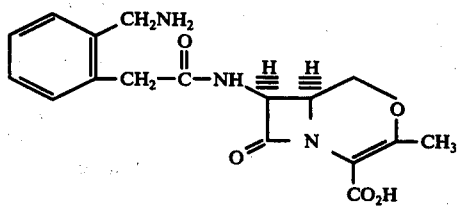

named 7$\beta$-(2-aminomethylphenylacetamido)-3-methyl-$\Delta^3$-0-2-isocephem-4-carboxylic acid.

The general methods of synthesis for the compounds of the present invention are illustrated below for the case in which Q is methyl in Charts A & B, for Q as benzyl in Chart C, for Q as phenethyl in Chart D, for Q as —CH$_2$COOZ in Chart E and for Q as hydrogen in Charts F, G, H, and J. Additional routes to desirable intermediates and final antibacterial agents are to be found in Chart I and in the examples and other disclosure which follow.
CHART A
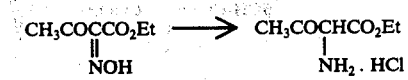
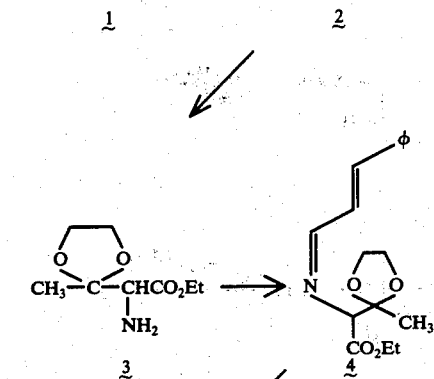
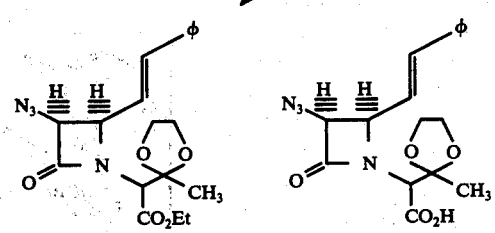
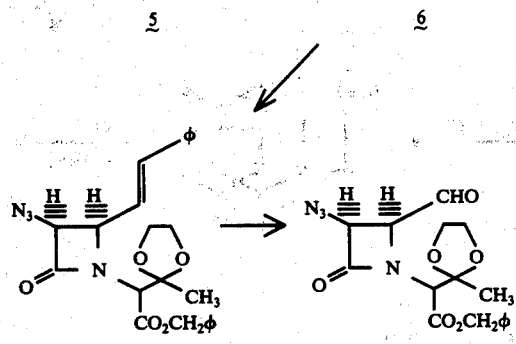
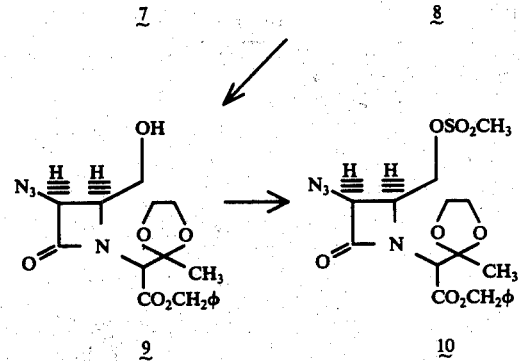
-continued
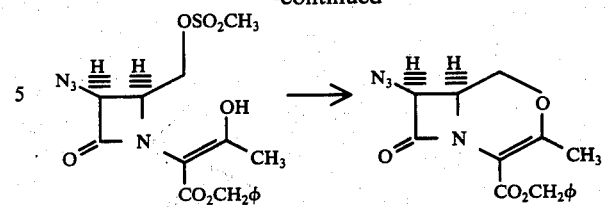
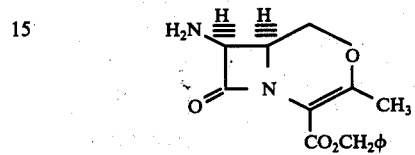
Et = $C_2H_5$
$\phi$ = $C_6H_5$
CHART A'
(simultaneous reduction and deblocking)
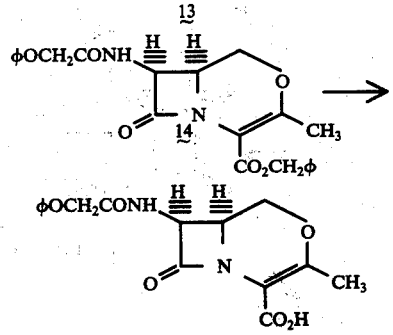
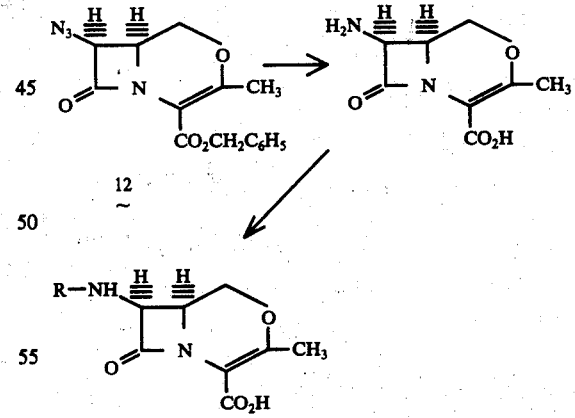
R = acyl group
CHART B
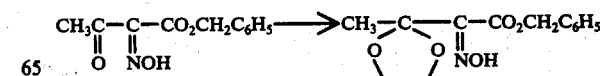

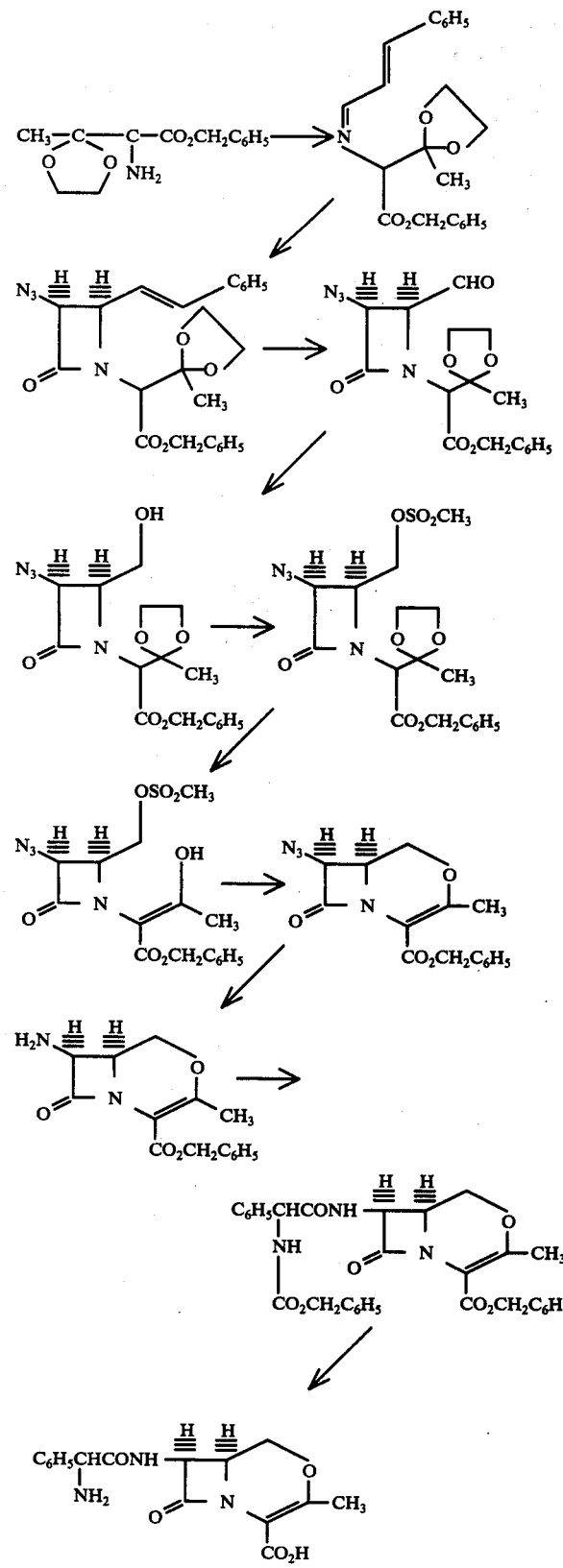
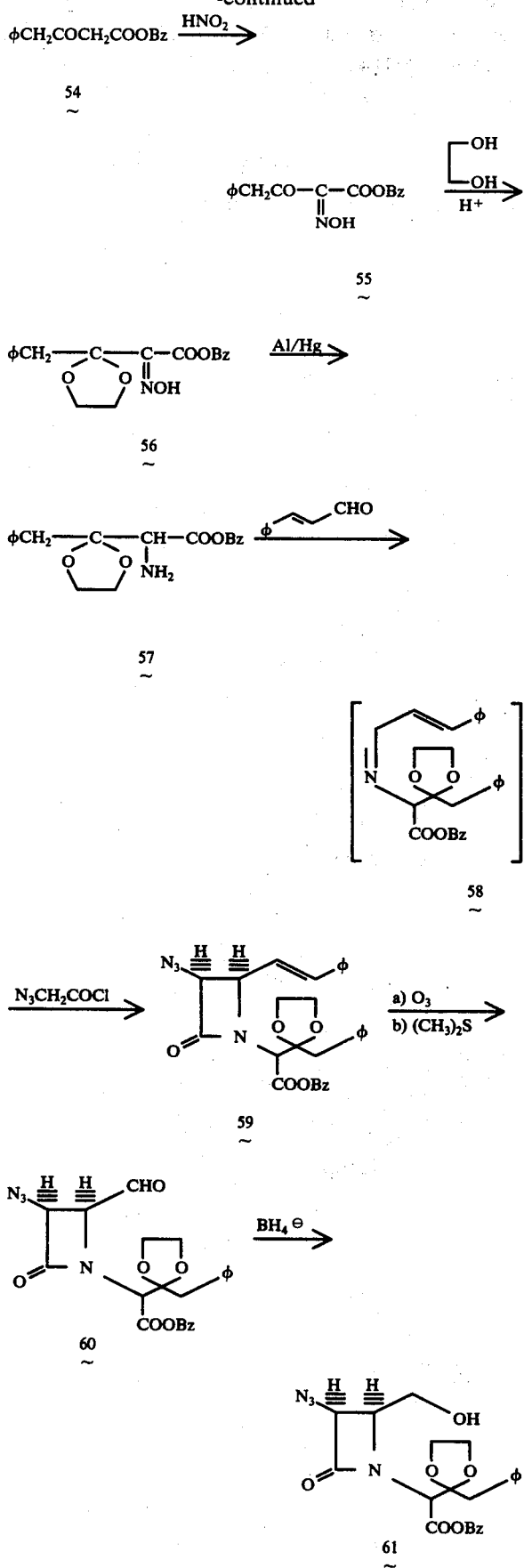
CHART C

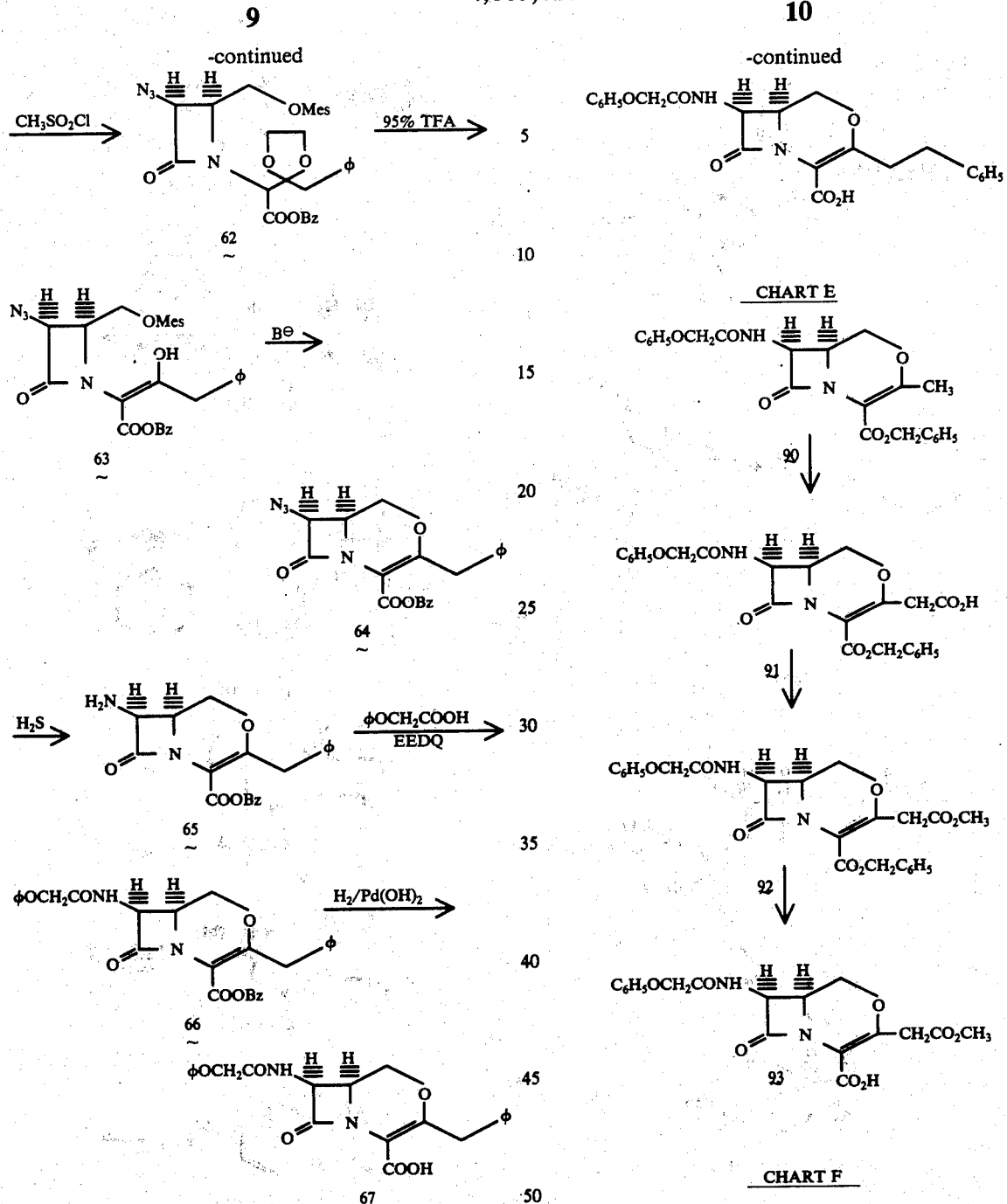

-continued
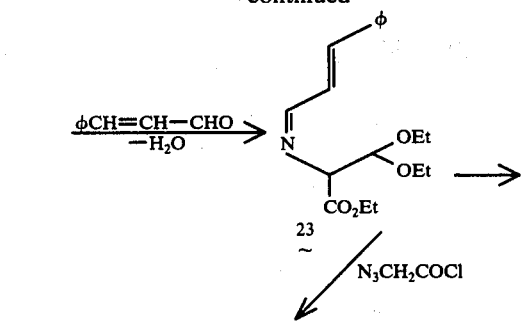
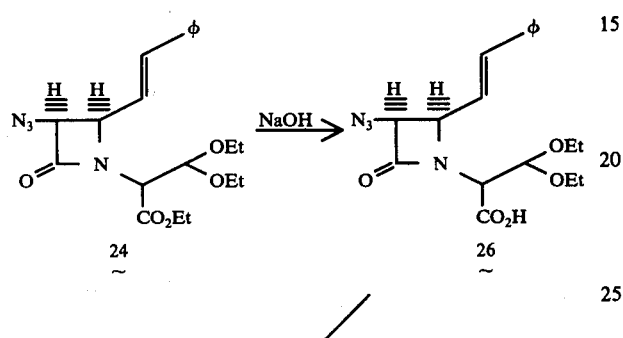
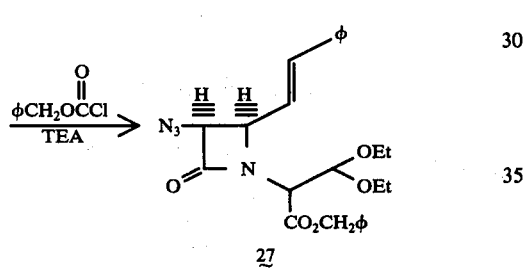
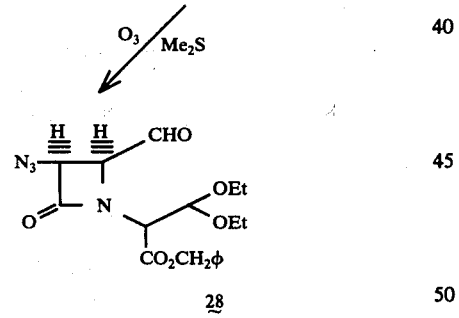
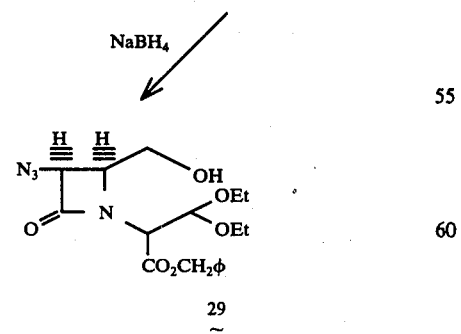
-continued
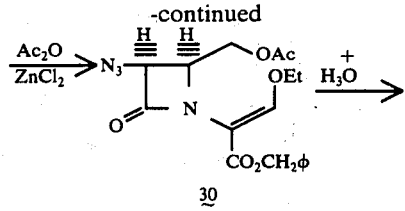
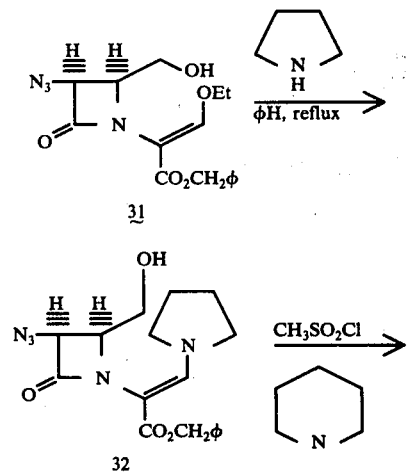
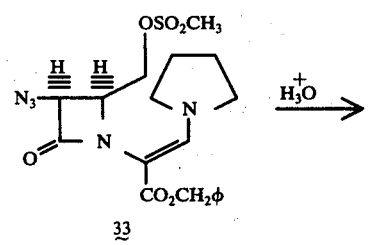
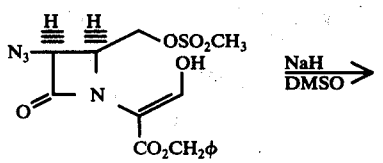
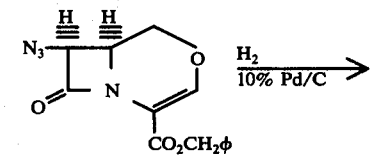
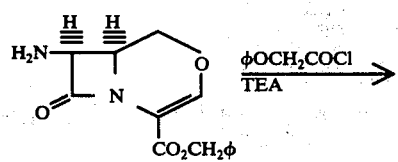
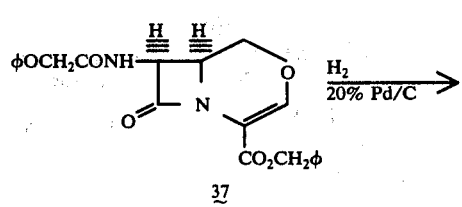

4,065,623
-continued
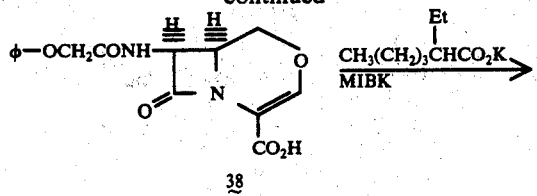
38
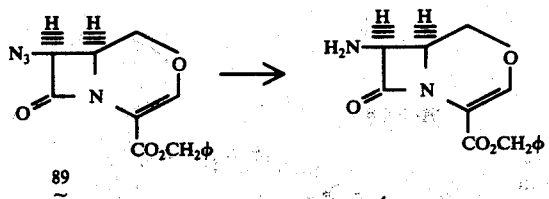
39
Et = C₂H₅
Ac = CH₃CO
φ = C₆H₅
DMSO = dimethylsulfoxide
Me = CH₃
MIBK = methyl isobutyl Ketone
CHART G
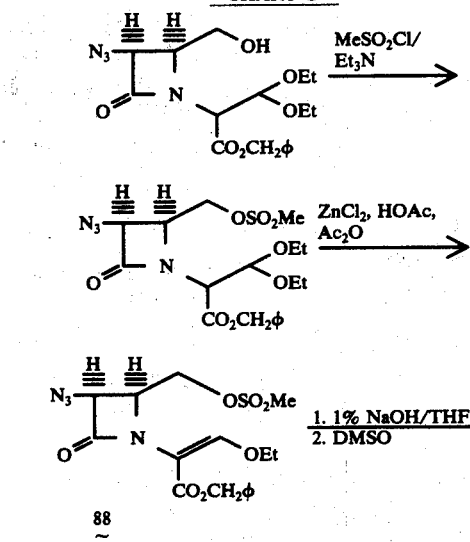
88
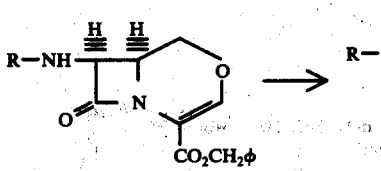
89
R = acyl group
CHART H
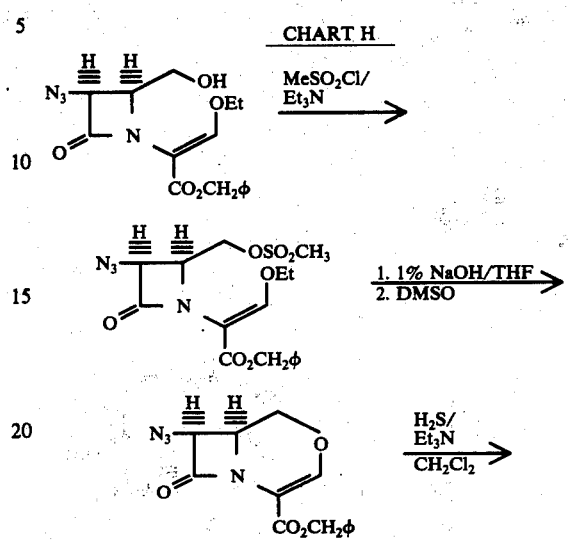
Me = CH₃
Et = C₂H₅
φ = C₆H₅
THF = tetrahydrofuran
DMSO = dimethylsulfoxide
R = acyl group
CHART I
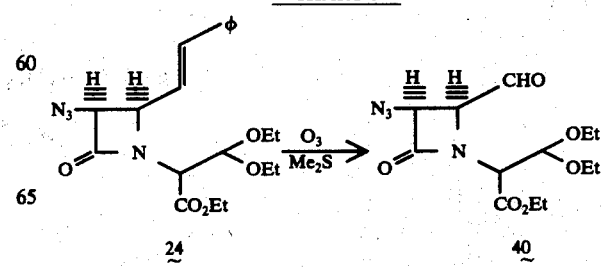
24    40
Et = C₂H₅
φ = C₆H₅
Me = CH₃
HOAc = CH₃COOH
Ac₂O = (CH₃CO)₂O
THF = tetrahydrofuran
DMSO = dimethylsulfoxide -continued
CHART I
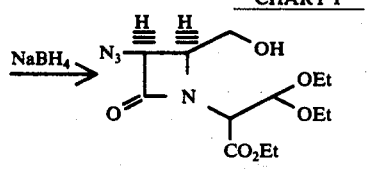
41
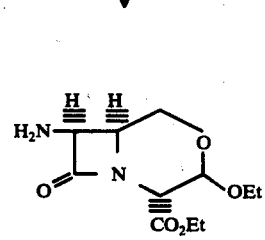
42
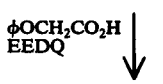
44
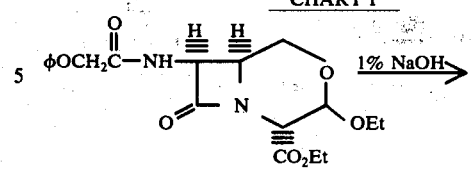
45
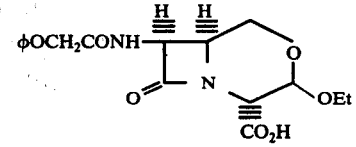
46
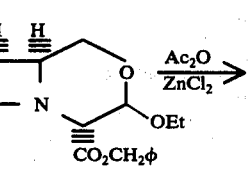
43
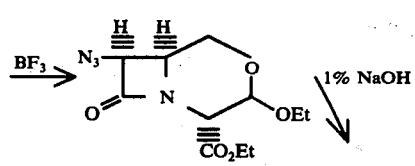
43
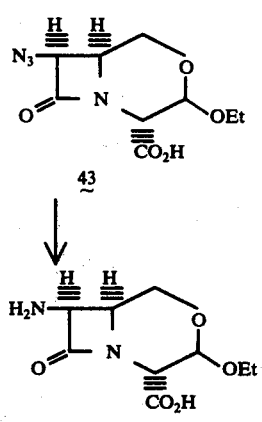
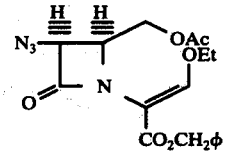
30
Et = C$_2$H$_5$
Me = CH$_3$
φ = C$_6$H$_5$
Ac$_2$O - (CH$_3$CO)$_2$O
CHART J
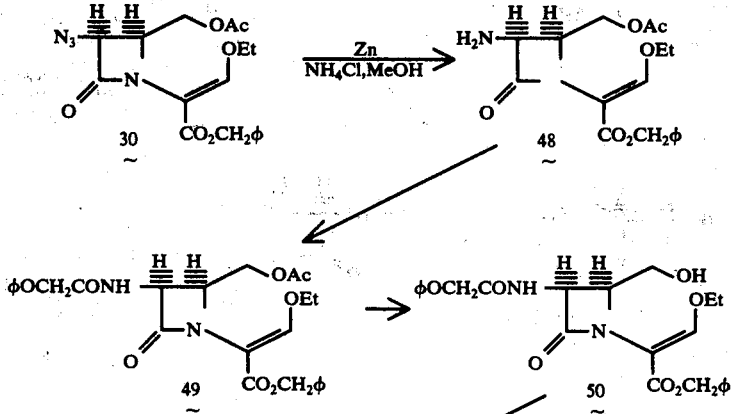

-continued

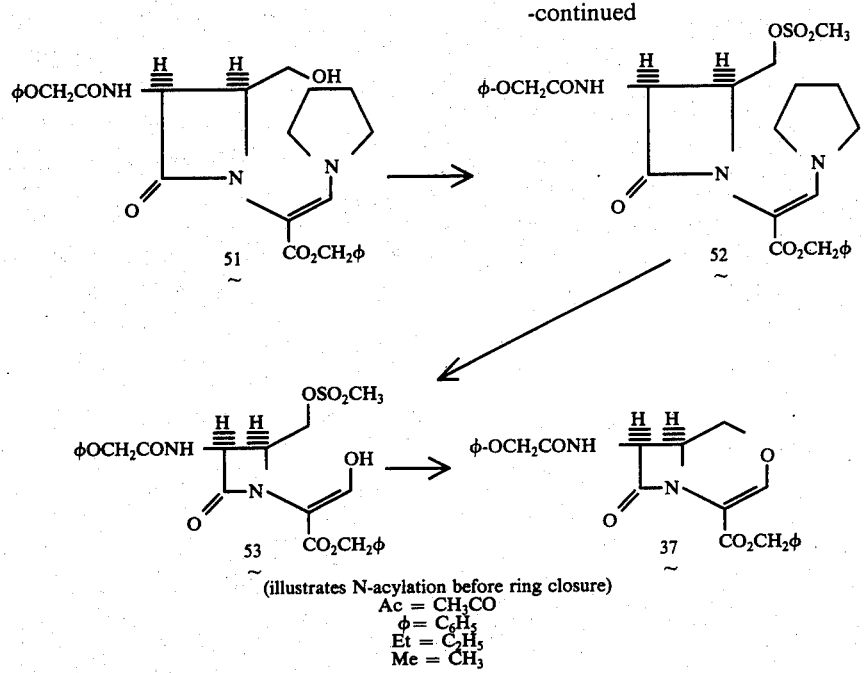

(illustrates N-acylation before ring closure)
Ac = CH₃CO
φ = C₆H₅
Et = C₂H₅
Me = CH₃

There is thus provided by the present invention the novel 0-2-isocephem compounds having the formula

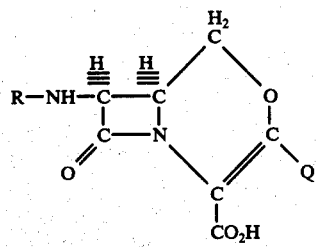

wherein R is an acyl group and Q is hydrogen, alkyl, aralkyl or —CH₂COOZ in which Z is hydrogen or the residue of an ester group and easily cleavable esters and pharmaceutically acceptable salts thereof.

The acyl group R can be chosen from a wide variety of organic acyl radicals which yield products of improved properties and is preferably an acyl radical which is contained in a naturally occurring or biosynthetically, semi-synthetically or totally-synthetically active N-acyl derivative of 6-aminopenicillanic acid or 7-aminocephalosporanic acid. Examples of suitable acyl groups are defined in the following general formulae, but it should be noted that this is not intended to be an exhaustive list of all the possible acyl groups which may be used.

$$R^a C_n H_{2n} CO—\qquad\qquad (i)$$

where $R^a$ is aryl (carbocyclic or heterocyclic), substituted aryl, cycloalkyl, substituted cycloalkyl, cycloalkenyl, substituted cycloalkenyl or a nonaromatic or mesoionic heterocyclic group, and n is an integer from 1–4. The preferred $R^a$ substituents are (a) aryl selected from phenyl, 2-thienyl, 3-thienyl, furyl, 4-isoxazolyl, pyridyl, tetrazolyl, sydnone-3 or -4, imidazolyl, naphthoyl, quinoxalinyl, triazolyl, isothiazolyl, thiadiazolyl, thiazolyl, oxazolyl, oxadiazolyl, pyrazolyl, furazan, pyrazinyl, pyrimidinyl, pyridazinyl or triazinyl; (b) substituted aryl in which the aryl groups mentioned above under (a) are substituted by one or more radicals selected from chloro, bromo, iodo, fluoro, nitro, amino, cyano, (lower)alkanoyloxy, (lower)alkanoyl, (lower)alkoxyamino, (lower)alkoxy, (lower)alkyl, (lower)alkylamino, hydroxy, guanidino, (lower)alkylthio, carboxy, phenyl, halophenyl, trifluoromethyl, di(lower)alkylamino, sulfamyl, (lower)alkanoylamino, phenyl(lower)alkylamido, cycloalkylamino, allylamido morpholinocarbonyl, pyrrolidinocarbonyl, piperidinocarbonyl, tetrahydropyridino, furfurylamido or N-alkyl-N-anilino; (c) $C_3$–$C_{12}$ cycloalkyl; (d) substituted $C_3$–$C_{12}$ cycloalkyl where the substituents are one or more radicals selected from chloro, bromo, fluoro, iodo, nitro, trifluoromethyl, $C_1$–$C_4$ alkyl, $C_1$–$C_4$ alkylamino, $C_1$–$C_2$ alkoxy or amino; (e) $C_3$–$C_{12}$ cycloalkenyl, said cycloalkenyl group having 1 or 2 double bonds; and (f) substituted $C_3$–$C_{12}$ cycloalkenyl, said cycloalkenyl group having 1 or 2 double bonds and being substituted by one or more radicals selected from chloro, bromo, fluoro, iodo, nitro, trifluoromethyl, $C_1$–$C_4$ alkyl, $C_1$–$C_4$ alkylamino, $C_1$–$C_2$ alkoxy or amino. The most preferred $R^a$ groups are phenyl; phenyl substituted by one or more radicals selected from chloro, bromo, iodo, fluoro, nitro, amino, (lower)alkyl, guanidino, (lower)alkylthio, cyano, (lower)alkoxy, sulfamyl, (lower)alkylamino, hydroxy, acetoxy, or trifluoromethyl; 2-thienyl; 3-thienyl; tetrazolyl; sydnone -3; sydnone -4; furyl; isothiazolyl; thiadiazolyl optionally substituted with phenyl; oxadiazolyl optionally substituted with phenyl; thiazolyl; imidazolyl; triazolyl; oxazolyl; pyridyl; furazan optionally substituted at the 3-position with methoxy; 4-isoxazolyl optionally substituted at the 5-position with methyl and at the 3-position with phenyl or halophenyl; 1,4-cyclohexadienyl; 1-cyclohexenyl and 1-aminocyclohexyl.

The most preferred acyl groups of this category are those in which n is 1. Examples of this category include phenylacetyl, halophenylacetyl, nitrophenylacetyl, aminophenylacetyl, β-(o-aminomethylphenyl)propionyl, (lower)alkanoyloxyphenylacetyl (e.g. p-acetoxyphenylacetyl), (lower)alkoxyphenylacetyl (e.g. methoxyphenylacetyl, ethoxyphenylacetyl), (lower)alkylphenylacetyl (e.g. methylphenylacetyl or ethylphenylacetyl), hydroxyphenylacetyl (e.g. o-hydroxyphenylacetyl), (lower)alkylaminophenylacetyl (e.g. o-, m- or p-aminomethylphenylacetyl), o- m- or p- guanidinophenylacetyl, o-carboxyphenylacetyl, N,N-bis-(2-chloroethyl)aminophenylpropionyl, thien-2 and 3-ylacetyl, 2- or 3- furylacetyl, 1,2,5-thiadiazole-3-acetyl, isothiazolyl-4-acetyl, 4-isoxazolylacetyl, 1-cyclohexenylacetyl, 2-aminomethyl-1-cyclohexenylacetyl, 1-aminocyclohexylacetyl, 1,4-cyclohexadienylacetyl, 2-aminomethyl-1,4-cyclohexadienylacetyl, pyridylacetyl, tetrazolylacetyl (other heterocyclic groups of this type are disclosed in U.S. Pat. Nos. 3,819,623 and 3,516,997) or a sydnoneacetyl group as disclosed in U.S. Pat. Nos. 3,681,328, 3,530,123 and 3,563,983. Other groups of this type include 3-phenyl-5-chlorophenyl-5-methylisoxazol-4-ylacetyl and 3-(2,6-dichlorophenyl)-5-methylisoxazol-4-ylacetyl or a group in which isoxazolyl is replaced by isothiazole as disclosed in U.S. Pat. No. 3,551,440. Still other examples are o-, m- and p-(2'-aminoethoxy)phenylacetyl (as disclosed in U.S. Pat. No. 3,759,905), 4,5-dimethoxycarbonyl-1,2,3-triazol-1-ylacetyl or 4-cyano-1,2,3-triazol-1-yl-acetyl (as disclosed in U.S. Pat. No. 3,821,206) and imidazol-(1)-acetyl (as disclosed in U.S. Pat. No. 3,632,810);

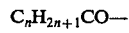 (ii)

where n is an integer from 1-7. The alkyl group may be straight or branched and, if desired, may be interrupted by an oxygen or sulphur atom or substituted by, e.g., a cyano group. Examples of this group include cyanoacetyl, valeryl, hexanoyl, heptanoyl, ethoxycarbonyl, octanoyl and butylthioacetyl. A preferred acyl group is cyanoacetyl;

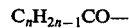 (iii)

where n is an integer from 2-7. The alkenyl group may be straight or branched and, if desired, may be interrupted by an oxygen or sulphur atom. An example of this group is allylthioacetyl;

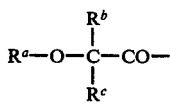 (iv)

where $R^a$ is as defined under (i) and in addition may be benzyl, $C_1-C_6$ alkyl or (lower)alkoxycarbonyl and $R^b$ and $R^c$ which may be the same or different each represent hydrogen, phenyl, benzyl, phenethyl or $C_1-C_6$ alkyl. The preferred $R^a$ substituents in this category are benzyl, $C_1-C_6$ alkyl, (lower)alkoxycarbonyl and those mentioned under (i) as being preferred aryl, substituted aryl, cycloalkyl (and substituted cycloalkyl) and cycloalkenyl (and substituted cycloalkenyl) groups. The most preferred $R^a$ group is phenyl. Examples of this group include phenoxyacetyl, 2-phenoxy-2-phenylacetyl, 2-phenoxypropionyl, 2-phenoxybutyryl, benzyloxyacetyl, 2-methyl-2-phenoxypropionyl, p-cresoxyacetyl, p-methylthiophenoxyacetyl and ethoxycarbonylacetyl;

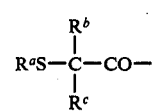 (v)

where $R^a$ is as defined under (i) and in addition may be benzyl or $C_1-C_6$ alkyl and $R^b$ and $R^c$ have the meanings defined under (iv). The preferred $R^a$ substituents in this category are benzyl, $C_1-C_6$ alkyl and those mentioned under (i) as being preferred aryl, substituted aryl, cycloalkyl (and substituted cycloalkyl) and cycloalkenyl (and substituted cycloalkenyl) groups. The most preferred aryl groups of this type are those in which $R^b$ and $R^c$ are hydrogen and $R^a$ is phenyl; phenyl substituted with one or more radicals selected from chloro, bromo, iodo, fluoro, nitro, amino, (lower)alkyl, (lower)alkylthio, cyano, (lower)alkoxy, (lower)alkylamino, hydroxy, acetoxy or trifluoromethyl; 3-pyridyl; or 4-pyridyl;

 (vi)

where $R^a$ is as defined under (i) and in addition may be benzyl, X is oxygen or sulphur and m is an integer from 2-5. The preferred $R^a$ groups are benzyl and those mentioned under (i) as being preferred aryl, substituted aryl, cycloalkyl (and substituted cycloalkyl) and cycloalkenyl (and substituted cycloalkenyl) groups. An example of this group is S-benzylthiopropionyl.

 (vii)

where $R^a$ is as defined under (i). The preferred $R^a$ groups are those mentioned under (i) as being preferred aryl, substituted aryl, cycloalkyl (and substituted cycloalkyl) and cycloalkenyl (and substituted cycloalkenyl) groups. The most preferred aryl groups of this category are those in which $R^a$ is phenyl; phenyl substituted with one or more radicals selected from chloro, bromo, iodo, fluoro, nitro, amino, (lower)alkyl, (lower)alkylthio, cyano, (lower)alkoxy, (lower)alkylamino, di(lower)alkylamino, hydroxy, acetoxy or trifluoromethyl, and most preferably phenyl substituted at the 2-position by carboxy or phenyl or at the 2- and 6-positions by methoxy; 2-ethoxynaphthoyl; 3-phenyl-5-methylisoxazol-4-yl; 3-o-chlorophenyl-5-methylisoxazol-4-yl; 3-(2,6-dichlorophenyl)-5-methylisoxazol-4-yl and 1-aminocyclohexyl. Examples of this group include 2,6-dimethoxybenzoyl, benzoyl, 2-biphenylcarbonyl, 2-aminomethylbenzoyl, 2-carboxybenzoyl-2-phenylbenzoyl, 2-thienylcarbonyl, 3-thienylcarbonyl and 2-chlorobenzoyl;

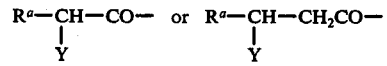 (viii)

where $R^a$ is as defined under (i) and Y is hydrazino, guanidino, ureido, thioureido and substituted thioureido (as disclosed in U.S. Pat. No. 3,741,962), allophanamido (as described in U.S. Pat. No. 3,483,188), 3-guanyl-1-ureido (as in U.S. Pat. No. 3,796,709), 3-(2-furoyl-)ureido, cyanamino (as in U.S. Pat. No. 3,796,709), 3-(benzoyl)ureido, azido, amino, acylamino (e.g. carbobenzoxyamino), a group obtained by reacting the amino group of the 7-side chain with an aldehyde or ketone (e.g. acetone, formaldehyde, acetaldehyde, butyraldehyde, acetylacetone, methyl acetoacetate, benzaldehyde, salicylaldehyde, methyl ethyl ketone or ethyl acetoacetate), hydroxy, etherified hydroxy, esterified hydroxy, carboxy, esterified carboxy (as disclosed for example in U.S. Pat. Nos. 3,282,926, 3,819,601 and 3,635,961 and including especially

), triazolyl, tetrazolyl, cyano, halogeno, acyloxy (e.g. formyloxy or (lower)alkanoyloxy), sulfo, sulfoamino or esterified sulfo. The preferred $R^a$ substituents are those mentioned under (i) as being preferred aryl, substituted aryl, cycloalkyl (and substituted cycloalkyl) and cycloalkenyl (and substituted cycloalkenyl) groups. Preferred Y substituents are hydrazino; guanidino; ureido; substituted thioureido of the formula

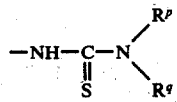

in which $R^p$ is hydrogen or $C_1$–$C_8$ alkyl and $R^q$ is hydrogen, $C_1$–$C_8$ alkyl, $C_2$–$C_8$ alkenyl, phenyl, benzoyl, $C_1$–$C_8$ alkoxy- $C_1$–$C_8$ alkyl, (carbo-$C_1$–$C_8$ alkoxy) $C_1$–$C_8$ alkyl; allophanamido; 3-guanyl-1-ureido; 3-(2-furoyl)ureido; 3-(benzoyl)ureido; azido; amino; a group obtained by reacting the amino group Y with acetone, formaldehyde, acetaldehyde, butyraldehyde, acetylacetone, methyl acetoacetate, benzaldehyde, salicylaldehyde, methyl ethyl ketone or ethyl acetoacetate; hydroxy; etherified hydroxy including especially (lower)alkoxy; carboxy; esterified carboxy including especially 5-indanyloxycarbonyl; triazolyl; tetrazolyl; cyano; cyanamino; halogeno; formyloxy; (lower)alkanoyloxy; sulfo; or sulfoamino. Examples of this group include α-aminophenylacetyl; α-carboxyphenylacetyl; 2,2-dimethyl-5-oxo-4-phenyl-1-imidazolyl; α-amino-p-hydroxyphenylacetyl; α-hydroxyphenylacetyl; α-formyloxyphenylacetyl and other aryl groups of this type disclosed in U.S. Pat. Nos. 3,812,116 and 3,821,017; α-amino-α-2- or 3-thienylacetyl; α-amino-α-(3-chloro-4-hydroxy)phenylacetyl; α-amino-α-(1,4-cyclohexadienyl)acetyl; α-azidophenylacetyl; α-amino-α-(1-cyclohexenyl)acetyl; 2-carboxy-α-3-thienylacetyl; α-amino-α-(3,5-dichloro-4-hydroxyphenyl)acetyl; α-amino-α-3- or 4- or 5-isothiazolylacetyl (as in U.S. Pat. No. 3,579,506) and other α-amino and α-hydroxy-heterocyclylacetyl groups as disclosed for example in U.S. Pat. No. 3,821,207;

 (ix)

where $R^d$, $R^e$ and $R^f$ which may be the same or different may each represent $C_1$–$C_6$ alkyl, phenyl or substituted phenyl. The preferred phenyl substituents are one or more radicals selected from chloro, bromo, iodo, fluoro, trifluoromethyl, nitro, amino, cyano, (lower)alkanoyloxy, (lower)alkanoyl, (lower)alkoxyamino, (lower)alkoxy, (lower)alkyl, (lower)alkylamino, hydroxy, (lower)alkylthio, carboxy, di(lower)alkylamino or sulfamyl. An example of this group is triphenylmethylcarbonyl.

 (x)

where $R^a$ is as defined under (i) and in addition may be hydrogen, $C_1$–$C_6$ alkyl, halogen substituted $C_1$–$C_6$ alkyl, phenethyl, phenoxymethyl; benzyl or

and X is oxygen or sulphur. An example of such a group is $Cl(CH_2)_2NHCO$;

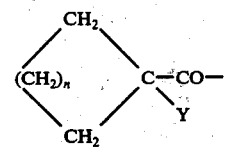

where Y is as defined under (viii) and n is an integer of 1–4. A most preferred Y substituent is amino. An example of this group is 1-aminocyclohexanecarbonyl.

xii. Aminoacyl, for example

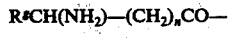

where n is an integer of 1–10, or

where m is zero or an integer from 1–10, and n is 0, 1, or 2; $R^g$ is hydrogen or an alkyl, aryl, aralkyl or carboxy group or a group as defined under $R^a$ in (i) above; and Ar is an arylene group, e.g. p-phenylene or 1,4-naphthylene. Preferred aryl groups of the above formulae are those in which $R^g$ is hydrogen, (lower)alkyl, phenyl, benzyl or carboxy and Ar is p-phenylene or 1,4-naphthylene. Examples of such groups are disclosed in U.K. Pat. No. 1,054,806. Examples of groups of this type include p-aminophenylacetyl and δ-aminoadipoyl derived from naturally occurring amino acids and derivatives thereof, e.g. N-benzoyl-δ-aminoadipoyl;

xiii. Substituted glyoxylyl groups of the formula

where $R^h$ is an aliphatic, araliphatic or aromatic group. The preferred $R^h$ groups are 2-thienyl; 3-thienyl; α-naphthyl; 2-phenanthryl or a mono-, di- or tri-substituted phenyl group, the substituents being selected from chloro, bromo, iodo, fluoro, amino, di(lower)alkylamino, (lower)alkyl, (lower)alkoxy, nitro or (lower)alkanoylamino. Examples of this category are disclosed in U.S. Pat. Nos. 3,546,219 and 3,573,294. Included in this group are also the α-carbonyl derivatives of the above substituted glyoxylyl groups formed for example with hydroxylamine, semicarbazide, thiosemicarbazide, isoniazide or hydrazine;

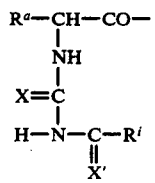  (xiv)

where R$^a$ has the meaning defined under (i), X is oxygen or sulphur, X' is oxygen or imino and R$^i$ represents (lower)alkyl, cycloalkyl having 4,5,6 or 7 carbon atoms, monohalo(lower)alkyl, dichloromethyl, trichloromethyl, (lower)alkenyl of 2–6 carbon atoms,

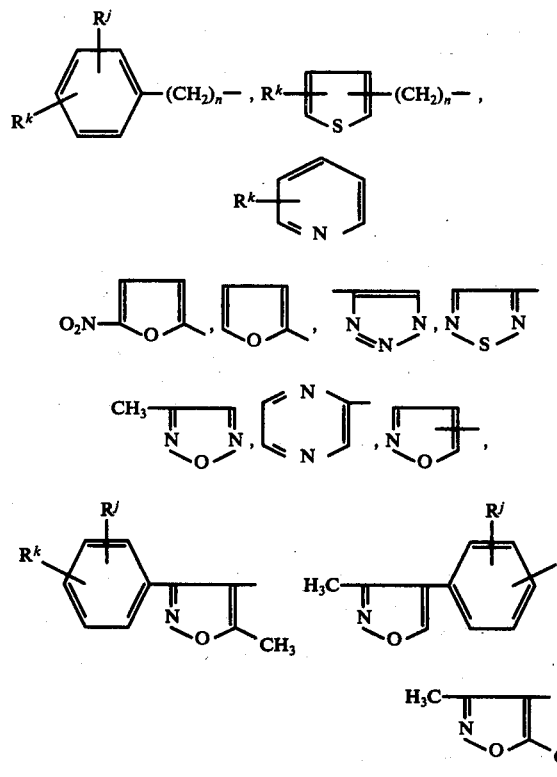

n is an integer from 0 to 3 inclusive and each of R$^k$ and R$^j$ is hydrogen, nitro, di(lower)alkylamino, (lower)alkanoylamino, (lower)alkanoyloxy, C$_1$–C$_6$ alkyl, C$_1$–C$_6$ alkoxy, sulfamyl, chloro, bromo, iodo, fluoro or trifluoromethyl. The preferred R$^a$ substituents are those mentioned under (i) as being preferred aryl, substituted aryl, cycloalkyl (and substituted cycloalkyl) and cycloalkenyl (and substituted cycloalkenyl) groups. Preferred acyl groups of this type are those in which R$^a$ is 2-thienyl; 3-thienyl; phenyl; or phenyl substituted by one or more radicals selected from nitro, di(lower)alkylamino, (lower)alkanoylamino, amino, hydroxy, (lower)alkanoyloxy, C$_1$–C$_6$ alkyl, C$_1$–C$_6$ alkoxy, sulfamyl, chloro, bromo, iodo, fluoro or trifluoromethyl; X is oxygen; X' is oxygen or imino and R$^i$ is (lower)alkyl, phenyl, 2-thienyl, 3-thienyl, 2-furyl or 5-nitro-2-furyl. The most preferred groups are those of the above formula where R$^a$ is phenyl, p-hydroxyphenyl, 2-thienyl or 3-thienyl; X is oxygen; X' is oxygen, and R$^i$ is phenyl or 2-furyl. Examples are disclosed in U.S. Pat. Nos. 3,687,949 and 3,646,024;

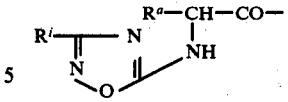  (xv)

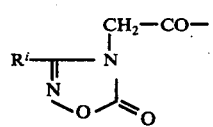

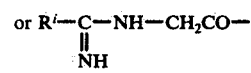

where R$^a$ has the meaning defined in (i) and R$^i$ has the meaning defined in (xiv). The preferred R$^a$ substituents are those mentioned under (i) as being preferred aryl, substituted aryl, cycloalkyl (and substituted cycloalkyl) and cycloalkenyl (and substituted cycloalkenyl) groups. Preferred R$^i$ substituents include (lower)alkyl, dichloromethyl, C$_4$–C$_7$ cycloalkyl, 2-thienyl, 3-thienyl, phenyl, benzyl, halobenzyl,

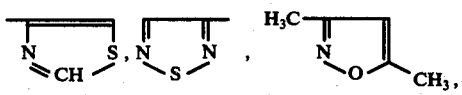

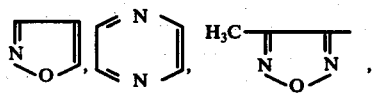

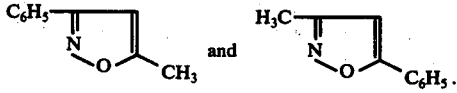

Examples of this group are disclosed in U.S. Pat. Nos. 3,626,024 and 3,692,779;

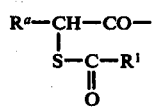

where R$^a$ has the meaning defined in (i) and R$^l$ is (lower)alkyl, C$_3$–C$_{12}$ cycloalkyl, aryl (especially phenyl), a monocyclic heterocyclic radical having 5 or 6 atoms exclusive of hydrogen which are C, S, N or O, no more than 2 atoms being other than C, or a substituted monocyclic heterocyclic radical as defined above having one or more substituents selected from halo, (lower)alkyl, (lower)alkoxy or phenyl. Examples of this group are disclosed in U.S. Pat. No. 3,778,436. Most preferred R$^l$ groups are (lower)alkyl, phenyl, thienyl or furyl.

A preferred class of acyl groups are those of the formula

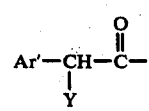

wherein Ar' is a radical of the formula

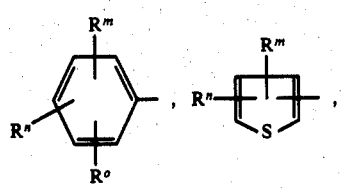 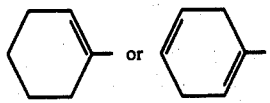

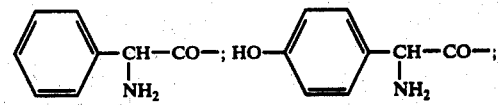

in which $R^m$, $R^n$ and $R^o$ are alike or different and each is hydrogen, hydroxy, (lower)alkyl, cyano, (lower)alkoxy, chloro, bromo, iodo, fluoro, trifluoromethyl, nitro, amino, (lower)alkylamino, di(lower)alkylamino, (lower)alkanoyl, (lower)alkanoyloxy such as p-acetoxy or phenyl and Y is amino or a group obtained by reacting the amino group with acetaldehyde, formaldehyde or acetone, fluoro, chloro, bromo, iodo, hydroxy, (lower)alkanoyloxy, carboxy, guanidino, 3-guanyl-1-ureido, 3-(2-furoyl)ureido, 3-benzoylureido, sulfo, sulfoamino, ureido, thioureido, (lower)alkoxy, cyano, cyanamino or indanyloxycarbonyl. Particularly preferred Ar radicals are phenyl, p-hydroxyphenyl, 4-hydroxy-3,5-dichlorophenyl, 3-chloro-4-hydroxyphenyl, o-, m- or p- aminomethylphenyl, 2-thienyl, 3-thienyl, 1-cyclohexenyl and 1,4cyclohexadienyl. Particularly preferred Y groups are amino, hydroxy and carboxy. Set forth below are formulae of the most preferred acyl groups of this class:

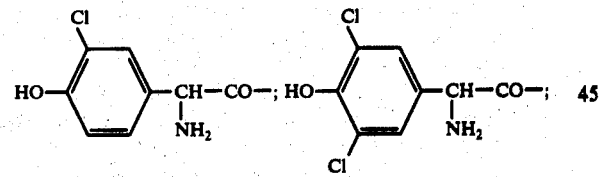

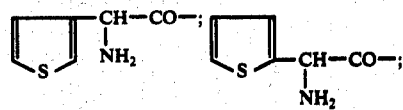

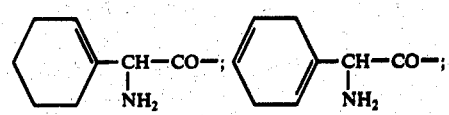

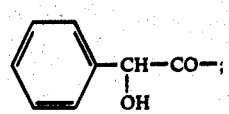

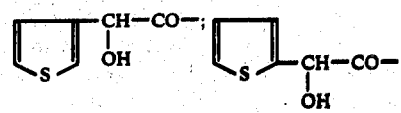

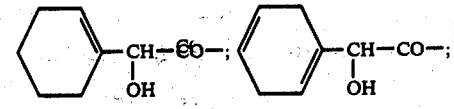

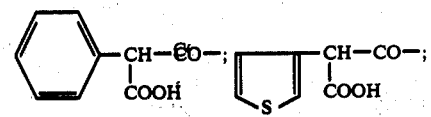

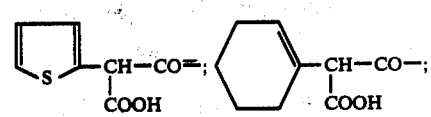

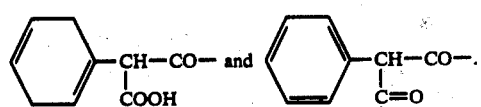

Of most interest are the acyl groups of the above class where the acid ArCH(X)COOH is of the D-series.

Other particularly preferred acyl groups for the compounds of formula I are

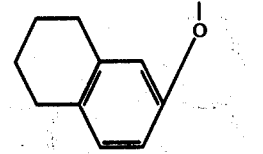

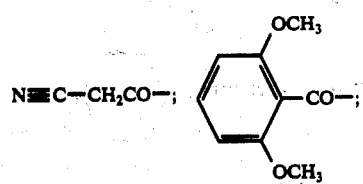

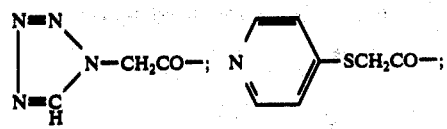

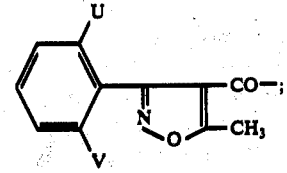

where U and V are alike or different and each is hydrogen, chloro or fluoro;

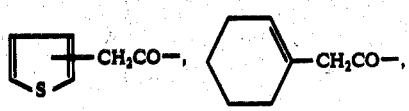

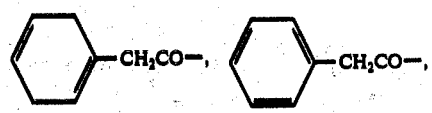

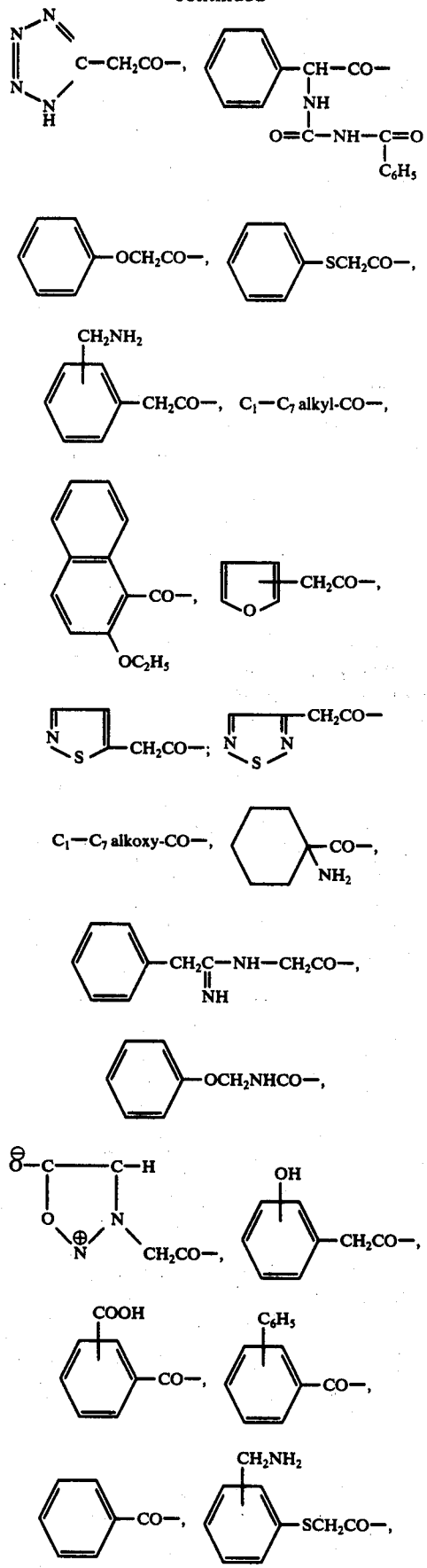

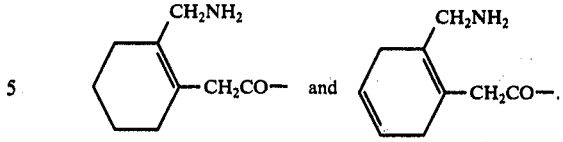

The term "(lower)alkyl" as used herein means both straight and branched chain aliphatic hydrocarbon radicals having from one to ten carbon atoms such as methyl, ethyl, propyl, isopropyl, butyl, isobutyl, t-butyl, amyl, hexyl, 2-ethylhexyl, heptyl, decyl, etc. Similarly, where the term "(lower)" is used as part of the description of another group, e.g. "(lower)-alkoxy", it refers to the alkyl portion of such group which is therefore described above in connection with "(lower)alkyl".

The pharmaceutically acceptable salts referred to above include the nontoxic carboxylic acid salts, e.g. nontoxic metallic salts such as sodium, potassium, calcium and aluminum, the ammonium salt and salts with nontoxic amines, e.g. trialkylamines, procaine, dibenzylamine, N-benzyl-β-phenethylamine, 1-ephenamine, N,N'-dibenzylethylenediamine, N-alkylpiperidine and other amines which have been used to form salts of penicillins and cephalosporins. When a basic group is present, as when it occurs in the 7-acyl group, the present invention also includes the pharmaceutically acceptable acid addition salts, e.g. salts with mineral acids such as hydrochloric, hydrobromic, hydroiodic, phosphoric, sulfuric and salts with organic acids such as maleic, acetic, citric, oxalic, succinic, benzoic, tartaric, fumaric, mandelic, ascorbic and malic. The term "pharmaceutically acceptable salts" is also meant to include nontoxic acid addition salts of the easily cleavable esters referred to above. The compounds which contain a basic group in radical R may also be present in the form of an internal salt, i.e. in the form of the zwitterion.

The easily cleavable esters referred to above include ester groups which are removable by methods, e.g. chemical or enzymatic hydrolysis, treatment with chemical reducing agents under mild conditions, irradiation with ultraviolet light or catalytic hydrogenation, which do not result in any appreciable destruction of the remaining portion of the molecule. Examples of suitable esters include those disclosed in U.S. Pat. Nos. 3,284,451 and 3,249,622 and U.K. Pat. Nos. 1,229,453 and 1,073,530. Esters which have been used previously in penicillin and cephalosporin chemistry include for example benzhydryl, p-nitrobenzyl, benzyl, trichloroethyl, silyl such as trimethylsilyl, phenacyl, p-methoxybenzyl, acetonyl, phthalidyl, indanyl and (lower)alkyl such as methyl, ethyl and t-butyl. Particularly preferred easily cleavable esters are those which are hydrolyzed under physiological conditions such as pivaloyloxymethyl, acetoxymethyl, phthalidyl, indanyl and methoxymethyl.

As the 0-2-isocephem compounds of the present invention may possess one or more asymmetric carbon atoms, the invention includes all of the possible enantiomeric and diastereomeric forms of the compounds of the general formula I shown above. Resulting mixtures of isomers can be separated into the individual isomers according to methods which are known per se, e.g. fractional crystallization, adsorption chromatography or other suitable separation processes. Resulting racemates can be separated into the antipodes in the usual manner after introduction of suitable salt-forming groupings, e.g. by forming a mixture of diastereoisomeric salts with optically active salt-forming agents, separating the mixture into diastereoisomeric salts, and converting the separated salts into the free compounds, or by fractional crystallization from optically active solvents.

It will be appreciated that certain of the compounds of this invention exist in various states of solvation and the anhydrous as well as solvated forms are within the scope of the invention.

The free acid compounds of general formula I where R is acyl and physiologically hydrolyzed esters thereof together with the pharmaceutically acceptable salts of such free acids and esters are active antibacterial agents. The remaining compounds of the above general formula I including salts thereof are valuable intermediates which can be converted into the above-mentioned pharmacologically active compounds in a simple manner, for example, as described below.

Preferred embodiments of the present invention are the 0-2-isocephem compounds having the formula

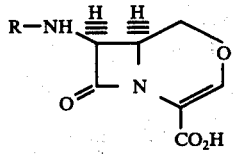

II wherein R represents an acyl group, and easily cleavable esters and pharmaceutically acceptable salts thereof.

Preferred acids, esters and salts of formula II are those in which acyl group R is selected from the acyl groups defined above under (i) to (xvi). The acyl groups mentioned as being preferred groups within categories (i) to (xvi) are also preferred in the compounds defined by general formula II.

More preferred acids, esters and salts of formula II are those in which acyl group R is

in which Ar' is a radical of the formula

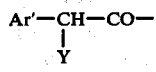

in which $R^m$, $R^n$ and $R^o$ are alike or different and each is hydrogen, hydroxy, (lower)alkyl, cyano, (lower)alkoxy, chloro, bromo, iodo, fluoro, trifluoromethyl, nitro, amino, (lower)alkylamino, di(lower)alkylamino, (lower)alkanoyl, (lower)alkanoyloxy such as p-acetoxy or phenyl and Y is amino or a group obtained by reacting the amino group with acetaldehyde, formaldehyde or acetone, fluoro, chloro, bromo, iodo, hydroxy, (lower)alkanoyloxy, carboxy, chloro, bromo, iodo, hydroxy, (lower)alkanoyloxy, carboxy, guanidino, 3-guanyl-1-ureido, 3-(2-furoyl)ureido, 3-benzoylureido, sulfo, sulfoamino, ureido, thioureido, (lower)alkoxy, cyano, cyanamino or indanyloxycarbonyl.

Other preferred acids, esters and salts of formula II are those in which R is

Ar'—CH—CO—
|
Y wherein Ar' is phenyl, p-hydroxyphenyl, 4-hydroxy-3,5-dichlorophenyl, 3-chloro-4-hydroxyphenyl, o-, m- or p-aminomethylphenyl, 2-thienyl, 3-thienyl, 1-cyclohexenyl or 1,4-cyclohexadienyl and Y is amino, carboxy or hydroxy.

Other preferred compounds of formula II are those wherein R is an acyl group of the formula

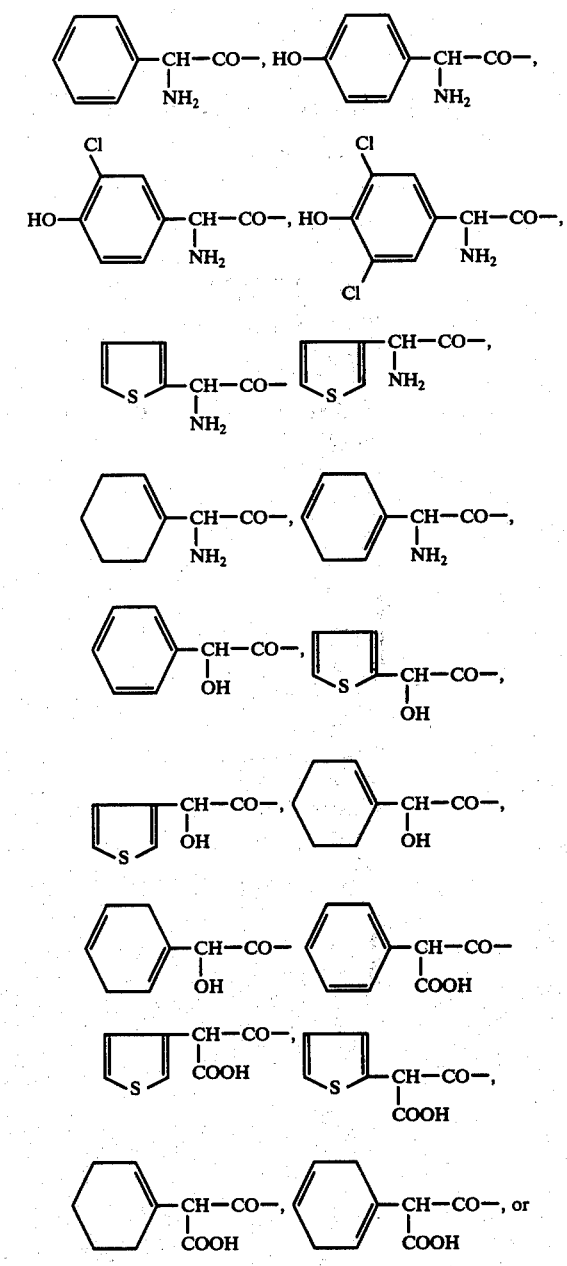

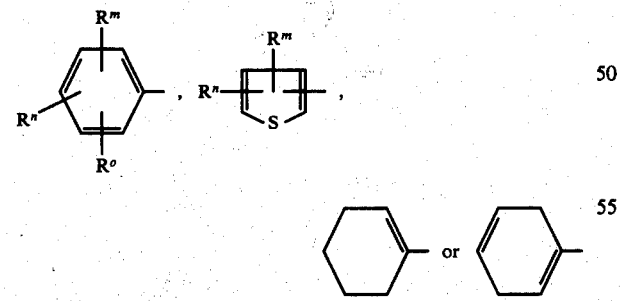

Other preferred compounds of formula II are those wherein R is an acyl group of the formula wherein U and V are alike or different and each is hydrogen, chloro or fluoro;

A most preferred group of compounds are those acids defined by formula II wherein R is α-carboxyphenylacetyl, cyanoacetyl, α-amino-α-(p-hydroxyphenyl)acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)acetyl, α-amino-α-(1,4-cyclohexadienyl)acetyl, α-hydroxyacetyl, α-hydroxy-α-(2-thienyl)acetyl, α-hydroxy-α-(3-thienyl)acetyl, α-hydroxy-α-(1-cyclohexenyl)acetyl, α-hydroxy-α-(1,4-cyclohexadienyl)acetyl, α-carboxy-α-(2-thienyl)acetyl, α-carboxy-α-(3-thienyl)acetyl, α-carboxy-α-(1-cyclohexenyl)acetyl, α-carboxy-α-(1,4-cyclohexadienyl)-acetyl, α-indanyloxycarbonyl-α-phenylacetyl, 1-(1H)-tetrazolyl, 4-pyridylthioacetyl, 2-thienylacetyl, 3-thienylacetyl, 1-cyclohexenylacetyl, 1,4-cyclohexadienylacetyl, o-aminomethylphenylacetyl, 1-aminocyclohexylcarbonyl, 2,6-dimethoxybenzoyl, sydnoneacetyl or α-azidophenylacetyl, or a pharmaceutically acceptable salt thereof.

Another most preferred group of compounds are the D-isomers of those acids defined by formula II wherein R is α-amino-α-(p-hydroxyphenyl)acetyl, α-amino-α-(3-chloro-4-hydroxyphenyl)acetyl, α-amino-α-(3,5-dichloro-4-hydroxyphenyl)-acetyl, α-amino-α-(2-thienyl)acetyl, α-amino-α-(3-thienyl)-acetyl, α-amino-α-(1-cyclohexenyl)acetyl, α-amino-α-(1,4-cyclohexadienyl)acetyl, α-hydroxyacetyl, α-hydroxy-α-(2-thienyl)acetyl, α-hydroxy-α-(3-thienyl)acetyl, α-hydroxy-α-(1-cyclohexenyl)acetyl or α-hydroxy-α-(1,4-cyclohexadienyl)acetyl, or a pharmaceutically acceptable salt thereof.

A most preferred compound of formula II is the acid in which R is phenoxyacetyl, or a pharmaceutically acceptable salt thereof.

Another most preferred compound of formula II is the acid in which R is phenylacetyl, or a pharmaceutically acceptable salt thereof.

A still further most preferred compound of formula II is the acid in which R is α-aminophenylacetyl, or a pharmaceutically acceptable salt thereof. The isomer of this compound in which the α-carbon atom of the 7-acyl group is of the D-series is of particular importance due to its combination of good antibacterial activity and oral absorption.

Other preferred embodiments of the present invention are the 0-2-isocephem compounds having the general formula

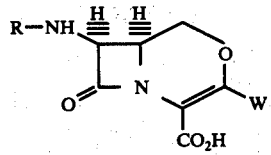

III wherein R represents an acyl group and W is alkyl or aralkyl, and easily cleavable esters and pharmaceutically acceptable salts thereof.

Preferred acids, esters and salts of formula III are those in which acyl group R is selected from the acyl groups defined above under (i) to (xvi). The acyl groups mentioned as being preferred groups within categories (i) to (xvi) are also preferred in the compounds defined by general formula III.

More preferred acids, esters and salts of formula III are those in which acyl group R is

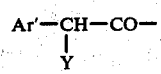

in which Ar' is a radical of the formula

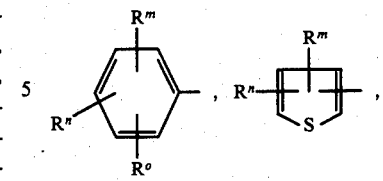

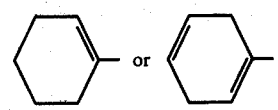

in which $R^m$, $R^n$ and $R^o$ are alike or different and each is hydrogen, hydroxy, (lower)alkyl, cyano, (lower)alkoxy, chloro, bromo, iodo, fluoro, trifluoromethyl, nitro, amino, (lower)alkylamino, di(lower)alkylamino, (lower)alkanoyl, (lower)alkanoyloxy such as p-acetoxy or phenyl and Y is amino or a group obtained by reacting the amino group with acetaldehyde, formaldehyde or acetone; fluoro; chloro; bromo; iodo; hydroxy; (lower)alkanoyloxy; carboxy; guanidino; 3-guanyl-1-ureido; 3-(2-furoyl)ureido; 3-benzoylureido; sulfo; sulfoamino; uriedo, thioureido; (lower)alkoxy; cyano; cyanamino; or indanyloxycarbonyl.

Other preferred acids, esters and salts of formula III are those in which R is

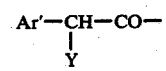

wherein Ar' is phenyl, p-hydroxyphenyl, 4-hydroxy-3,5-dichlorophenyl, 3-chloro-4-hydroxyphenyl, o-, m- or p-aminomethylphenyl, 2-thienyl, 3-thienyl, 1-cyclohexenyl or 1,4-cyclohexadienyl and Y is amino, carboxy or hydroxy.

Other preferred compounds of formula III are those wherein R is an acyl group of the formula

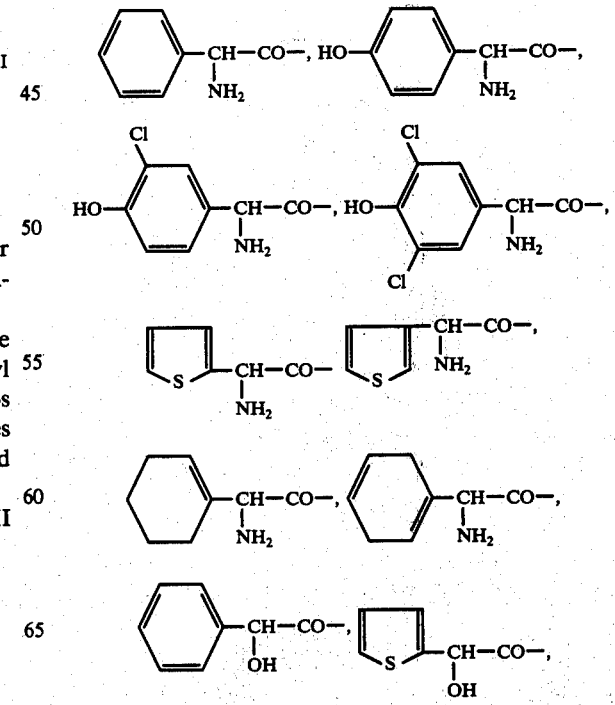

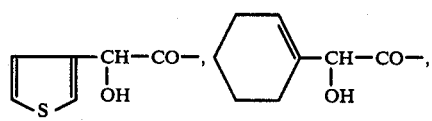
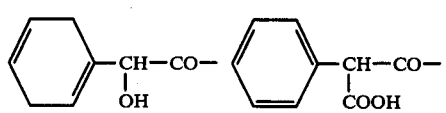
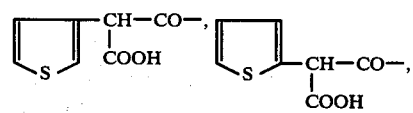
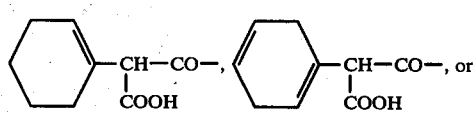
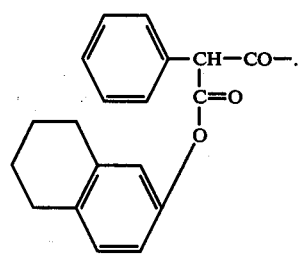
Other preferred compounds of formula III are those wherein R is an acyl group of the formula
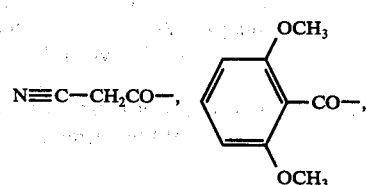
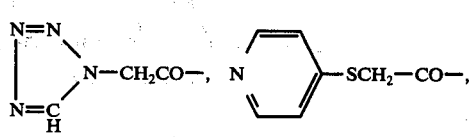
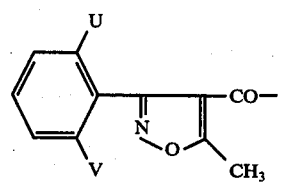
wherein U and V are alike or different and each is hydrogen, chloro or fluoro;
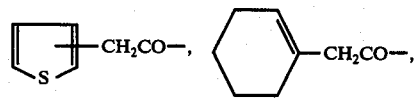
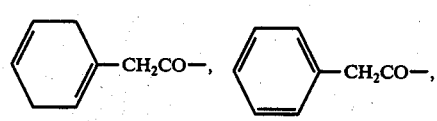
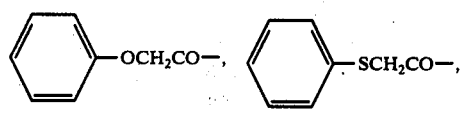
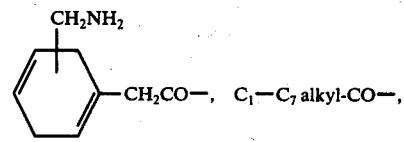
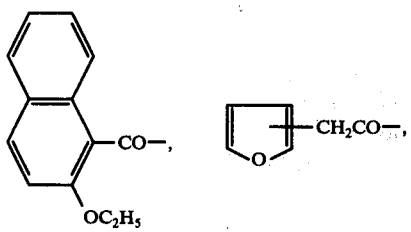
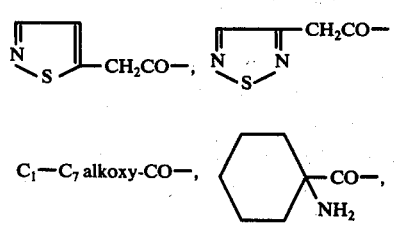
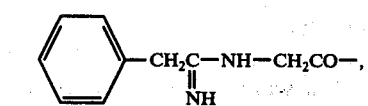
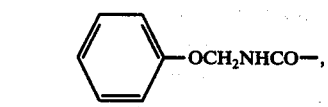
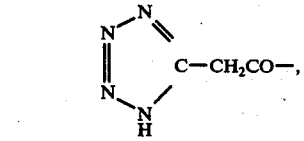
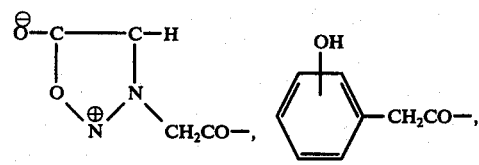
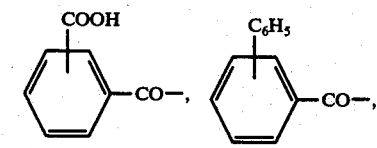
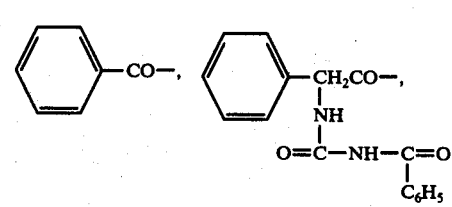

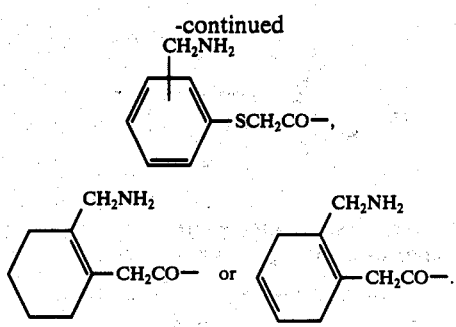

A most preferred group of compounds are those acids defined by formula III wherein R is α-carboxyphenylacetyl, cyanoacetyl, α-amino-α-(p-hydroxyphenyl)-acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)acetyl, α-amino-α-(1,4-cyclohexadienyl)acetyl, α-hydroxyacetyl, α-hydroxy-α-(2-thienyl)acetyl, α-hydroxy-α-(3-thienyl)acetyl, α-hydroxy-α-(1-cyclohexenyl)acetyl, α-hydroxy-α-(1,4-cyclohexadienyl)acetyl, α-carboxy-α-(2-thienyl)acetyl, α-carboxy-α-(3-thienyl)acetyl, α-carboxy-α-(1-cyclohexenyl)acetyl, α-carboxy-α-(1,4-cyclohexadienyl)-acetyl, α-indanyloxycarbonyl-α-phenylacetyl, 1-(1H)-tetrazolyl, 4-pyridylthioacetyl, 2-thienylacetyl, 3-thienylacetyl, 1-cyclohexenylacetyl, 1,4-cyclohexadienylacetyl, o-aminomethylphenylacetyl, 1-aminocyclohexylcarbonyl, 2,6-dimethoxybenzoyl, sydnoneacetyl or α-azidophenylacetyl, or a pharmaceutically acceptable salt thereof.

Another most preferred group of compounds are the D-isomers of those acids defined by formula III wherein R is α-amino-α-(p-hydroxyphenyl)acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)-acetyl, α-amino-α-(1,4-cyclohexadienyl)acetyl, α-hydroxyacetyl, α-hydroxy-α-(2-thienyl)acetyl, α-hydroxy-α-(3-thienyl)acetyl, α-hydroxy-α-(1-cyclohexenyl)acetyl or α-hydroxy-α-(1,4-cyclohexadienyl)acetyl, or a pharmaceutically acceptable salt thereof.

A most preferred group of compounds of formula III are the acids in which R is phenoxyacetyl, or a pharmaceutically acceptable salt thereof.

Another most preferred group of compounds of formula III are the acids in which R is phenylacetyl, or a pharmaceutically acceptable salt thereof.

A still further most preferred group of compounds of formula III are the acids in which R is α-aminophenylacetyl, or a pharmaceutically acceptable salt thereof. The isomers of these compounds in which the α-carbon atom of the 7-acyl group is of the D-series are of particular importance due to their combination of good antibacterial activity and oral absorption.

Substituent W in the compounds of formula III above may be any alkyl or aralkyl radical. Thus, the alkyl radical may be any saturated straight, branched or cyclic monovalent hydrocarbon radical but is preferably a hydrocarbon radical having from 1 to 10 carbon atoms. The aralkyl substituent may be any substituent in which a mono-, bi- or polycyclic aromatic radical, said radical being either carbocyclic or heterocyclic and being optionally mono-, di- or polysubstituted, is substituted for a hydrogen atom of an alkyl radical, said alkyl radical preferably being a saturated straight, branched or cyclic monovalent hydrocarbon radical having from 1 to 10 carbon atoms.

The most preferred compounds of general formula III are those in which W is methyl, benzyl or phenethyl.

A most preferred series of compounds of the present invention are the 0-2-isocephem compounds having the general formula

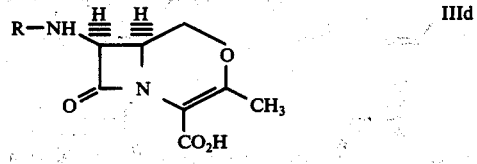

wherein R represents an acyl group, and easily cleavable esters and pharmaceutically acceptable salts thereof.

Preferred acids, esters and salts of formula IIId are those in which acyl group R is selected from the acyl groups defined above under (i) to (xvi). The acyl groups mentioned as being preferred groups within categories (i) to (xvi) are also preferred in the compounds defined by general formula IIId.

More preferred acids, esters and salts of formula IIId are those in which acyl group R is

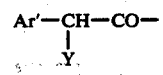

in which Ar' is a radical of the formula

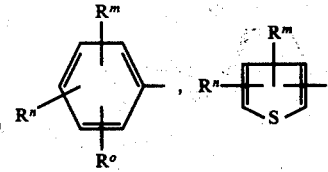

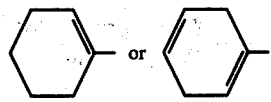

in which $R^m$, $R^n$ and $R^o$ are alike or different and each is hydrogen, hydroxyl, (lower)alkyl, cyano, (lower)alkoxy, chloro, bromo, iodo, fluoro, trifluoromethyl, nitro, amino, (lower)alkylamino, di(lower)alkylamino, (lower)alkanoyl, (lower)alkanoyloxy such as p-acetoxy or phenyl and Y is amino or a group obtained by reacting the amino group with acetaldehyde, formaldehyde or acetone; fluoro; chloro; bromo; iodo; hydroxy; (lower)alkanoyloxy; carboxy; guanidino; 3-guanyl-1-ureido; 3-(2-furoyl)ureido; 3-benzoylureido; sulfo; sulfoamino; ureido; thioureido; (lower)-alkoxy; cyano; cyanamino; or indanyloxycarbonyl.

Other preferred acids, esters and salts of formula IIId are those in which R is

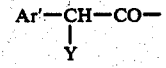

wherein Ar' is phenyl, p-hydroxyphenyl, 4-hydroxy-3,5-dichlorophenyl, 3-chloro-4-hydroxyphenyl, o-, m- or p-aminomethylphenyl, 2-thienyl, 3-thienyl, 1-cyclohexenyl or 1,4-cyclohexadienyl and Y is amino, carboxy or hydroxy.

Other preferred compounds of formula IIId are those wherein R is an acyl group of the formula

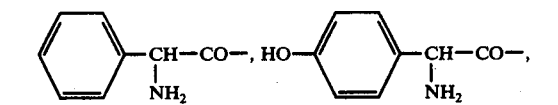
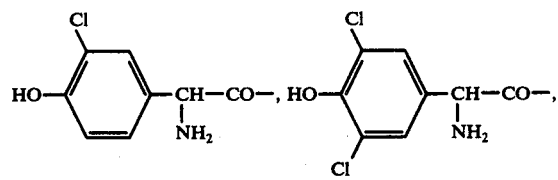
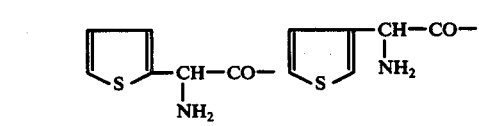
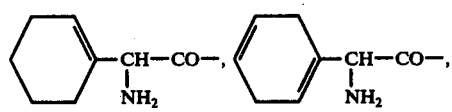
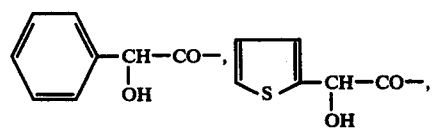
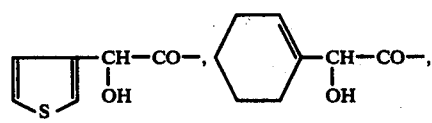
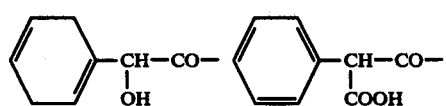
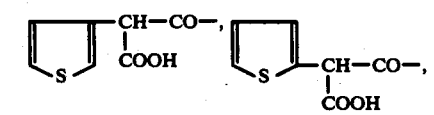
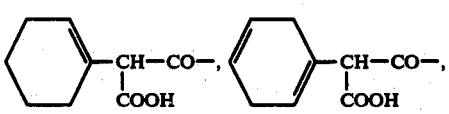
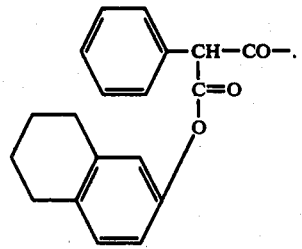

Other preferred compounds of formula IIId are those wherein R is an acyl group of the formula

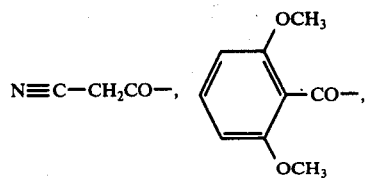
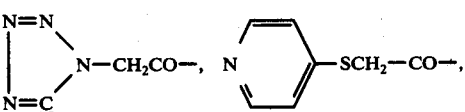
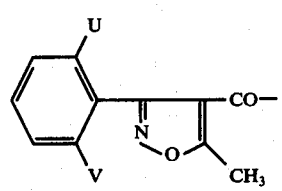

wherein U and V are alike or different and each is hydrogen, chloro or fluoro;

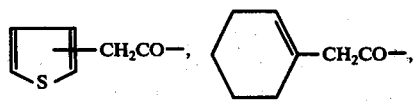
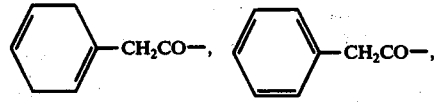
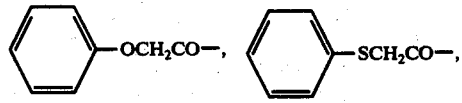
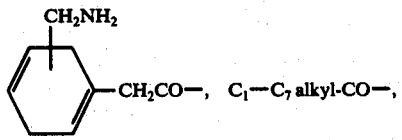
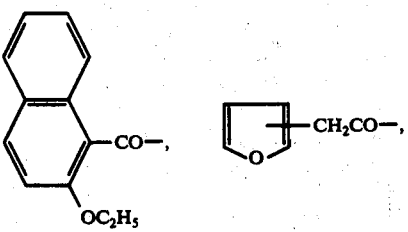
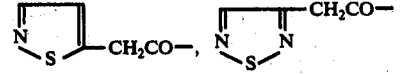
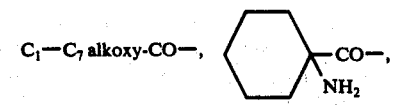
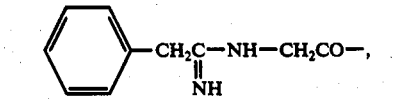

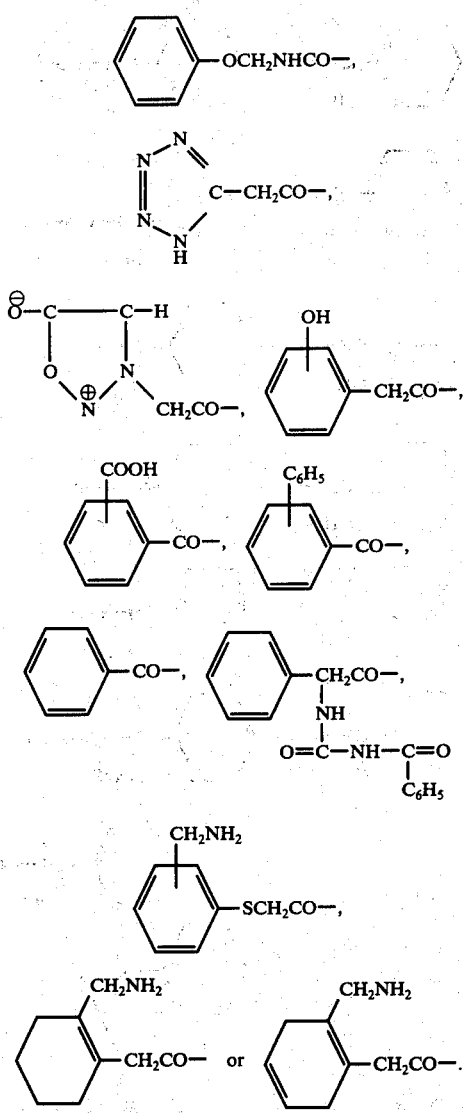

A most preferred group of compounds are those acids defined by formulae IIId wherein R is α-carboxyphenylacetyl, cyanoacetyl, α-amino-α-(p-hydroxyphenyl)-acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)acetyl, α-amino-α-(1,4-cyclohexadienyl)acetyl, α-hydroxyacetyl, α-hydroxy-α-(2-thienyl)acetyl, α-hydroxy-α-(3-thienyl)acetyl, α-hydroxy-α-(1-cyclohexenyl)acetyl, α-hydroxy-α-(1,4-cyclohexadienyl)acetyl, α-carboxy-α-(2-thienyl)acetyl, α-carboxy-α-(3-thienyl)acetyl, α-carboxy-α-(1-cyclohexenyl)acetyl, α-carboxy-α-(1,4-cyclohexadienyl)-acetyl, α-indanyloxycarbonyl-α-phenylacetyl, 1-(1H)-tetrazolyl, 4-pyridylthioacetyl, 2-thienylacetyl, 3-thienylacetyl, 1-cyclohexenylacetyl, 1,4-cyclohexadienylacetyl, o-aminomethylphenylacetyl, 1-aminocyclohexylcarbonyl, 2,6-dimethoxybenzoyl, sydnoneacetyl or α-azidophenylacetyl, or a pharmaceutically acceptable salt thereof. The most preferred easily cleavable esters of this group are the pivaloyloxymethyl, methoxymethyl, indanyl, phthalidyl and acetoxymethyl esters and pharmaceutically acceptable salts thereof.

Another most preferred group of compounds are the D-isomers of those acids defined by formula IIId wherein R is α-amino-α-(p-hydroxyphenyl)acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)acetyl, α-amino-α-(1,4-cyclohexadienyl)acetyl, α-hydroxyacetyl, α-hydroxy-α-(2-thienyl)acetyl, α-hydroxy-α-(3-thienyl)acetyl, α-hydroxy-α-(1-cyclohexenyl)acetyl or α-hydroxy-α-(1,4-cyclohexadienyl)acetyl, or a pharmaceutically acceptable salt thereof. The most preferred easily cleavable esters of this group are the pivaloyloxymethyl, methoxymethyl, indanyl, phthalidyl and acetoxymethyl esters and pharmaceutically acceptable salts thereof.

A most preferred acid of formula IIId is that in which R is phenoxyacetyl, or a pharmaceutically acceptable salt thereof.

A most preferred acid of formula IIId is that in which R is phenylacetyl, or a pharmaceutically acceptable salt thereof.

A most preferred acid of formula IIId is that in which R is α-aminophenylacetyl, or a pharmaceutically acceptable salt thereof.

A most preferred compound of formula IIId is the pivaloyloxymethyl, acetoxymethyl, indanyl, phthalidyl or methoxymethyl ester of the acid in which R is α-aminophenylacetyl, or a pharmaceutically acceptable salt thereof.

A still more preferred compound of formula IIId is the D-isomer of an acid of formula IIId in which R is α-aminophenylacetyl, or a pharmaceutically acceptable salt thereof. This compound is found to be especially valuable in view of its combination of good antibacterial activity and oral absorption. The pivaloyloxymethyl, acetoxymethyl, indanyl, phthalidyl and methoxymethyl esters of the above acid as well as pharmaceutically acceptable salts thereof are also preferred compounds of the present invention.

Other preferred embodiments of the present invention are the 0-2-isocephem compounds having the general formula

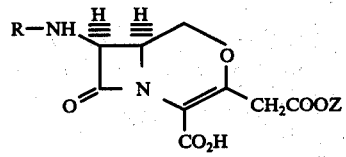

IV wherein R represents an acyl group and Z is hydrogen or the residue of an ester group, and easily cleavable esters and pharmaceutically acceptable salts thereof. The free carboxylic acids, physiologically hydrolyzed esters and pharmaceutically acceptable salts of such acids and esters are active antibacterial agents.

Preferred acids, esters and salts of formula IV are those in which Z is $C_1$–$C_6$ alkyl and acyl group R is selected from the acyl groups defined above under (i) to (xvi). The acyl groups mentioned as being preferred groups within categories (i) to (xvi) are also preferred in the compounds defined by general formula IV.

More preferred acids, esters and salts of formula IV are those in which Z is $C_1$–$C_6$ alkyl and acyl group R is

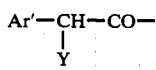

in which Ar' is a radical of the formula

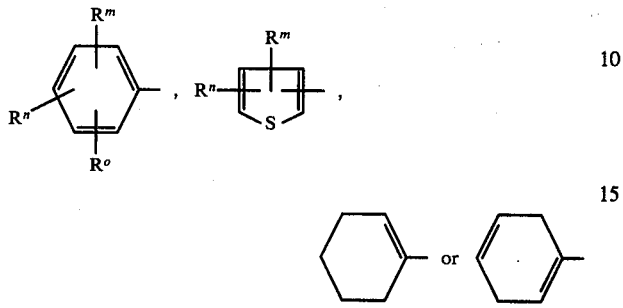

in which $R^m$, $R^n$ and $R^o$ are alike or different and each is hydrogen, hydroxy, (lower)alkyl, cyano, (lower)alkoxy, chloro, bromo, iodo, fluoro, trifluoromethyl, nitro, amino, (lower)alkylamino, di(lower)alkylamino, (lower)-alkylamino, (lower)alkylamino, (lower)alkanoyl, (lower)alkanoyloxy such as p-acetoxy or phenyl and Y is amino or a group obtained by reacting the amino group with acetaldehyde, formaldehyde or acetone; fluoro; chloro; bromo; iodo; hydroxy; (lower)alkanoyloxy; carboxy; guanidino; 3-guanyl-1-ureido; 3-(2-furoyl)ureido; 3-benzoylureido; sulfo; sulfoamino; ureido; thioureido; (lower)alkoxy; cyano; cyanamino; or indanyloxycarbonyl.

Other preferred acids, esters and salts of formula IV are those in which Z is $C_1$–$C_6$ alkyl and R is

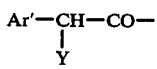

wherein Ar' is phenyl, p-hydroxyphenyl, 4-hydroxy-3,5-dichlorophenyl, 3-chloro-4-hydroxyphenyl o-, m- or p-aminomethylphenyl, 2-thienyl, 3-thienyl, 1-cyclohexenyl or 1,4-cyclohexadienyl and Y is amino, carboxy or hydroxy.

Other preferred compounds of formula IV are those wherein Z is $C_1$–$C_6$ alkyl and R is an acyl group of the formula

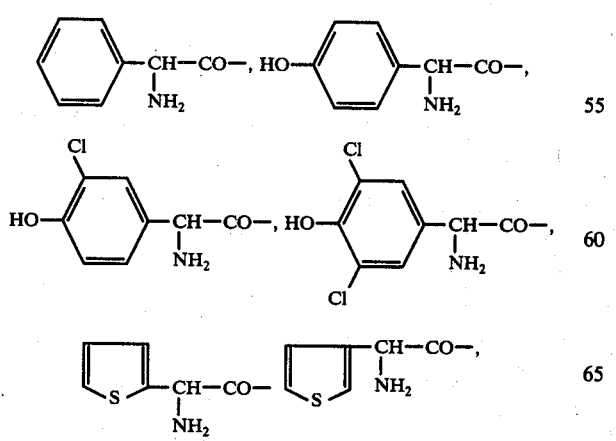

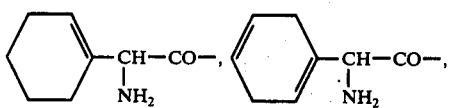

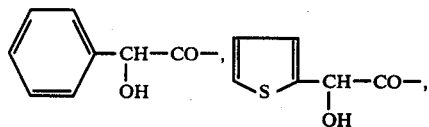

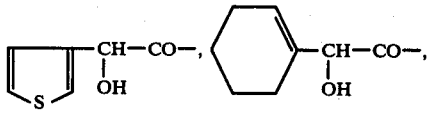

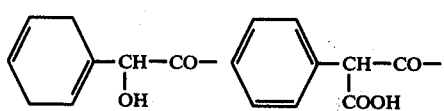

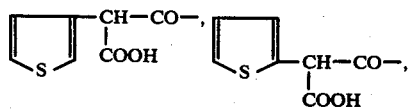

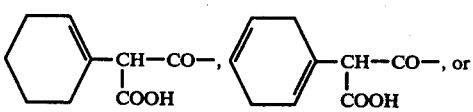

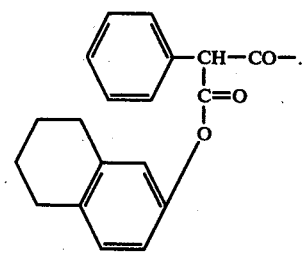

Other preferred compounds of formula IV are those wherein Z is $C_1$–$C_6$ alkyl and R is an acyl group of the formula

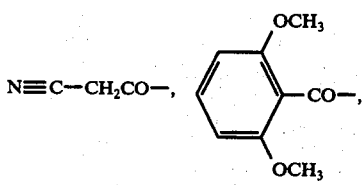

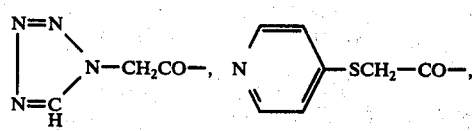

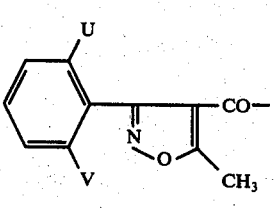

wherein U and V are alike or different and each is hydrogen, chloro or fluoro;

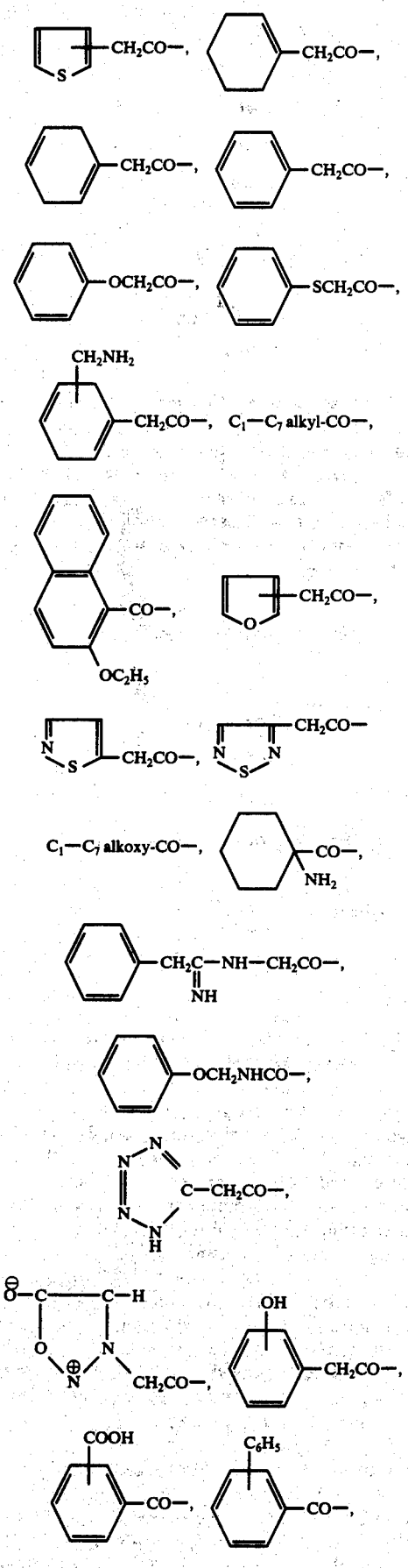
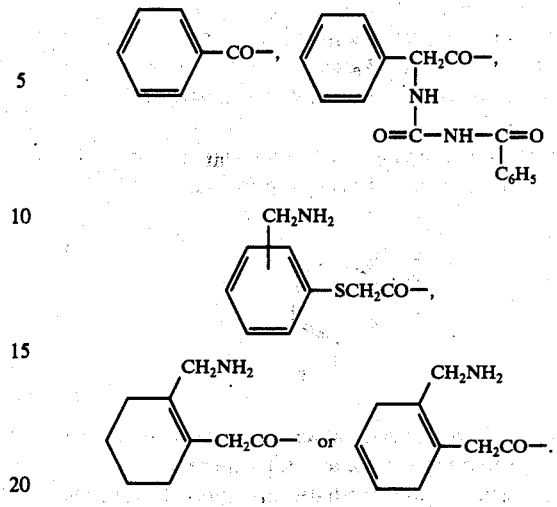

A most preferred group of compounds are those acids defined by formula IV wherein Z is $C_1$–$C_6$ alkyl and R is α-carboxyphenylacetyl, cyanoacetyl, α-amino-α-(p-hydroxyphenyl)acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)acetyl, α-amino-α-(1,4-cyclohexadienyl)-acetyl, α-hydroxyacetyl, α-hydroxy-α-(2-thienyl)acetyl, α-hydroxy-α-(3-thienyl)acetyl, α-hydroxy-α-(1-cyclohexenyl)acetyl, α-hydroxy-α-(1,4-cyclohexadienyl)acetyl, α-carboxy-α-(2-thienyl)acetyl, α-carboxy-α-(3-thienyl)-acetyl, α-carboxy-α-(1-cyclohexenyl)acetyl, α-carboxy-α-(1,4-cyclohexadienyl)acetyl, α-indanyloxycarbonyl-α-phenylacetyl, 1-(1H)tetrazolyl, 4-pyridylthioacetyl, 2-thienylacetyl, 3-thienylacetyl, 1-cyclohexenylacetyl, 1,4-cyclohexadienylacetyl, o-aminomethylphenylacetyl, 1-aminocyclohexylcarbonyl, 2,6-dimethoxybenzoyl, sydnoneacetyl or α-azidophenylacetyl, or a pharmaceutically acceptable salt thereof.

Another most preferred group of compounds are the D-isomers of those acids defined by formula IV wherein Z is $C_1$–$C_6$ alkyl and R is α-amino-α-(p-hydroxyphenyl)-acetyl, α-amino-α-(3-chloro-4-hydroxyphenyl)acetyl, α-amino-α-(3,5-dichloro-4-hydroxyphenylacetyl, α-amino-α-(2-thienyl)acetyl, α-amino-α-(3-thienyl)acetyl, α-amino-α-(1,-cyclohexenyl)acetyl, α-amino-α-(1,4-cyclohexadienyl)acetyl, α-hydroxyacetyl, α-hydroxy-α-(2-thienyl)-acetyl, α-hydroxy-α-(3-thienyl)acetyl, α-hydroxy-α-(1-cyclohexenyl)acetyl or α-hydroxy-α-(1,4-cyclohexadienyl)-acetyl, or a pharmaceutically acceptable salt thereof.

A most preferred group of compounds of formuls IV are the acids in which Z is $C_1$–$C_6$ alkyl and R is phenoxyacetyl, or a pharmaceutically acceptable salt thereof.

Another most preferred group of compounds of formula IV are the acids in which Z is $C_1$–$C_6$ alkyl and R is phenyl acetyl, or a pharmaceutically acceptable salt thereof.

A still further most preferred group of compounds of formula IV are the acids in which Z is $C_1$–$C_6$ alkyl and R is α-aminophenylacetyl, or a pharmaceutically acceptable salt thereof. The isomers of these compounds in which the α-carbon atom of the 7-acyl group is of the D-series are of particular importance due to their combination of good antibacterial activity and oral absorption.

The most preferred compounds of formula IV are those acids, esters and salts where Z is methyl.

The present invention further provides various novel intermediates useful in the synthesis of the pharmacologically active 0-2-isocephem antibacterial agents described above.

Preferred embodiments of the present invention are the novel intermediates having the formula

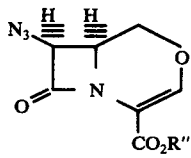 V wherein R" is hydrogen or an easily cleavable ester carboxyl-protecting group, and salts thereof.

Other preferred intermediates are those having the formula

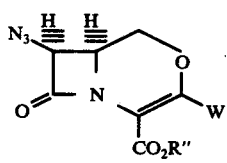 VI wherein W is alkyl, especially methyl, or aralkyl, especially benzyl or phenethyl, and R" is hydrogen or an easily cleavable ester carboxyl-protecting group, and salts thereof.

The most preferred intermediates of formula VI are those in which W is methyl.

Other preferred intermediates are the compounds having the formula

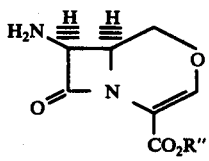 VII wherein R" is hydrogen or an easily cleavable ester carboxyl-protecting group, and salts thereof.

Other preferred intermediates are the compounds having the formula

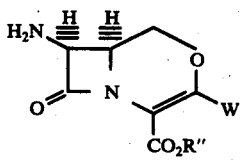 VIII where W is alkyl, especially methyl, or aralkyl, especially benzyl or phenethyl, and R" is hydrogen or an easily cleavable ester carboxyl-protecting group, and salts thereof. The most preferred intermediates of formula VIII are those in which W is methyl.

Still other preferred embodiments of the present invention are the novel intermediates having the formula

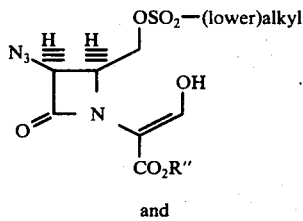 IX and

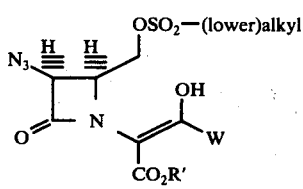 X wherein W is alkyl, preferably methyl, or aralkyl, preferably benzyl or phenethyl, and R' is an easily cleavable ester carboxyl-protecting group, and salts thereof. The (lower)alkyl substituent is preferably methyl. Formulae IX and X are condensed structural formulae and compounds IX and X as well as the other compounds of this invention may also be represented by structural formulae of the type, e.g.

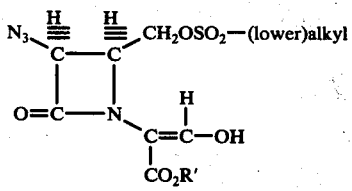 IX and

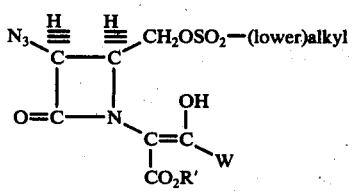 X

The intermediates of formulae V to X may be in the form of the free carboxylic acid or a salt thereof or in the form where the carboxyl group is protected in a conventional manner such as preferably by esterification. The protecting group is selected so that it may be removed by methods which do not result in any appreciable destruction of the remaining portion of the molecule. Preferred carboxyl protecting groups are the easily cleavable esters as defined above including in particular benzhydryl, p-nitrobenzyl, trichloroethyl, silyl including especially trimethylsilyl, phenacyl, p-methoxybenzyl, acetonyl, (lower)-alkyl such as methyl, t-butyl or ethyl, benzyl, triphenylmethyl, phthalidyl, indanyl, methoxymethyl, acetoxymethyl and pivaloyloxymethyl. The most preferred esters of formulae V to X are the pivaloyloxymethyl, methoxymethyl, phthalidyl, indanyl and acetoxymethyl esters, and salts thereof. The carboxyl-protecting group may be split off when desired by methods known per se, e.g. by mild acid or base hydrolysis, catalytic hydrogenation, irradiation with ultraviolet light, or reduction with chemical reducing agents. It will be appreciated that esterification is only a preferred method for blocking the carboxyl group and that other carboxyl-protected forms of the above intermediates, e.g. easily cleavable amides or anhydrides, are also intended to be included within the scope of the invention.

According to the present invention there is also provided a process for preparing 0-2-isocephem compounds of the formula

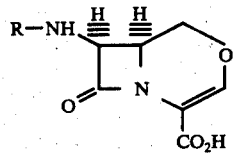

wherein R represents an acyl group, and easily cleavable esters and pharmaceutically acceptable salts thereof; which process comprises the consecutive steps of 1. reacting an ester of the formula

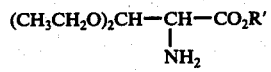

wherein R' is an easily cleavable ester carboxyl-protecting group with cinnamaldehyde in an inert organic solvent in the presence of a drying agent or with azeotropic removal of water to produce an imine of the formula

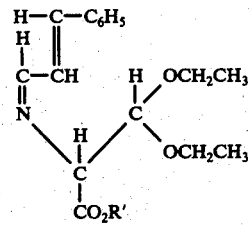

wherein R' is as defined above;

2. reacting said imine of formula XII with an azidoacetyl halide or an azidoacetic mixed anhydride in the presence of an organic base to produce a cis-β-lactam compound of the formula

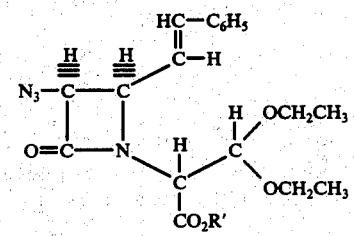

wherein R' is as defined above;

3. subjecting said β-lactam compound of formula IV to ozonolysis to produce an aldehyde of the formula

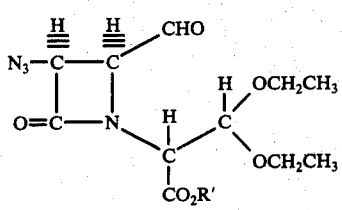

wherein R' is as defined above;

4. selectively reducing said aldehyde of formula XXVIII to the corresponding alcohol of the formula

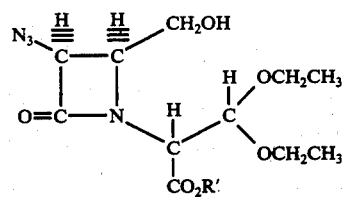

wherein R' is as defined above;

5. reacting the alcohol of formula XIII with an acid anhydride, preferably acetic anhydride or trifluoroacetic anhydride, in the presence of a Lewis acid to produce a compound of the formula

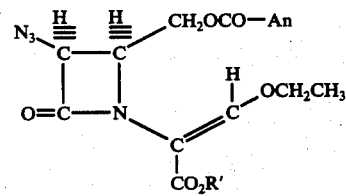

wherein R' is as defined above and An represents the residue of the acid anhydride;

6. subjecting the compound of formula XIV to acid hydrolysis to produce a compound of the formula

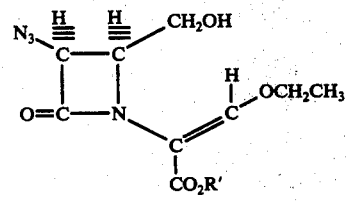

wherein R' is as defined above;

7. reacting the compound of formula XV with an amine, preferably a saturated cyclic secondary amine, to produce an enamine compound of the formula

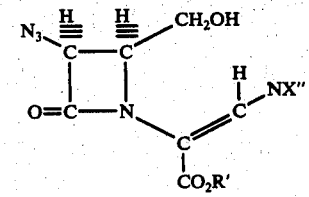

wherein R' is as defined above and X" is the residue of the amine;

8. reacting the enamine of formula XVI with a (lower)alkylsulfonating agent in the presence of an acid acceptor to produce a derivative of the formula

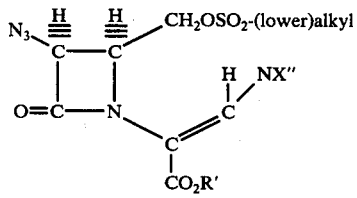

wherein R' and X" are as defined above;

9. subjecting said derivative of formula XVII to acid hydrolysis to produce an enol intermediate of the formula

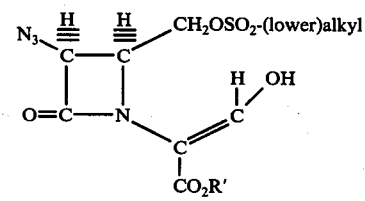

wherein R' is as defined above;

10. cyclizing said enol intermediates by treatment with base to produce an azido 0-2-isocephem intermediates of the formula

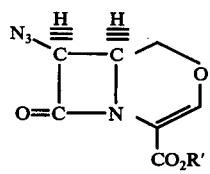

wherein R' is as defined above;

11. selectively reducing said azido intermediate of formula Va to produce a 7-amino 0-2-isocephem intermediate of the formula

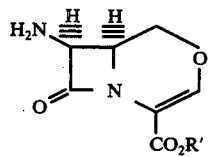

wherein R' is as defined above; and

12. N-acylating said 7-amino intermediate of formula VIIa or a salt thereof with an acylating acid of the formula

R—COOH wherein R is as defined above, or with its functional equivalent as an acylating agent for a primary amine, to produce a 7-acylamido 0-2-isocephem-4-carboxylic acid derivative of the formula

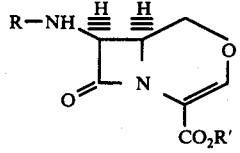

wherein R and R' are as defined above, or a pharmaceutically acceptable salt thereof and, if desired, performing one or more of the additional steps of 13. removing by methods known per se the carboxyl-protecting group R' to produce the corresponding free acid compound of formula II;

14. converting the free acid compound of formula II to a physiologically hydrolyzed ester thereof by methods known per se; or 15. converting the free acid compound of formula II or a physiologically hydrolyzed ester thereof to a pharmaceutically acceptable salt thereof by methods known per se.

A variation of the above-described process for preparing the 0-2-isocephem antibacterial agents of formula II and easily cleavable esters and pharmaceutically acceptable salts thereof involves reacting the alcohol of formula XIII with a (lower)alkylsulfonating agent in the presence of an acid acceptor to produce a derivative of the formula

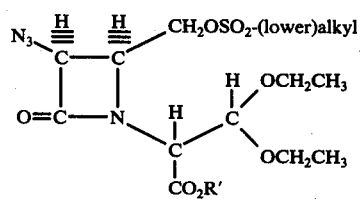

wherein R' is an easily cleavable ester carboxyl-protecting group. Compound XVIII is then reacted with an acid anhydride in the presence of a Lewis acid to produce a compound of the formula

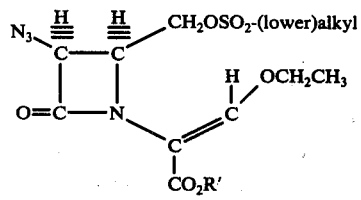

wherein R' is as defined above. Compound XIX is then subjected to base hydrolysis to form an enolate of the formula

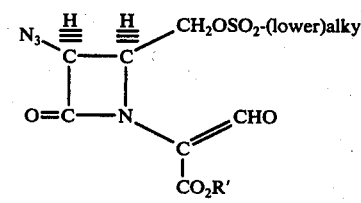

wherein R' is as defined above. Enolate XX then cyclizes on removal of water and exposure to a dipolar aprotic solvent such as dimethylsulfoxide to form the 7-azido 0-2-isocephem intermediate of formula Va which is subsequently reduced, N-acylated and optionally de-blocked according to the process described above to produce the desired compound of formula II or an easily cleavable ester or pharmaceutically acceptable salt thereof.

A still further alternative process for preparing compounds of formula II involves reacting the compound of the formula

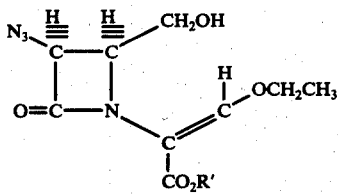   XV wherein R' is an easily cleavable ester carboxyl-protecting group with a (lower)alkylsulfonating agent in the presence of an acid acceptor to produce a derivative of the formula

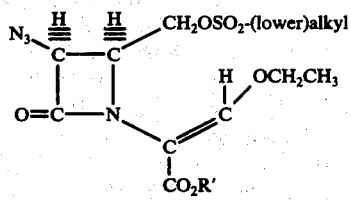   XIX wherein R' is as defined above. Compound XIX is then treated with base to produce an enolate of formula XX which cyclizes to the 7-azido 0-2-isocephem intermediate Va which is reacted as described above to produce the desired compound of formula II or an easily cleavable ester or pharmaceutically acceptable salt thereof.

A preferred embodiment of the present invention is the process of preparing a 7-acylamido 0-2-isocephem-4-carboxylic acid compound having the formula

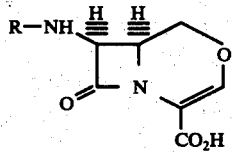   II wherein R represents an acyl group, and easily cleavable esters and pharmaceutically acceptable salts thereof; which process comprises N-acylating a 7-amino 0-2-isocephem intermediate of the formula

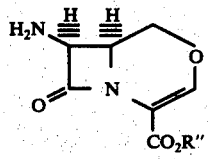   VII wherein R" is hydrogen or an easily cleavable ester carboxyl-protecting group R', or a salt thereof, with an acylating acid of the formula

R—COOH wherein R is as defined above, or with its functional equivalent as an acylating agent for a primary amine, to produce a 7-acylamido 0-2-isocephem-4-carboxylic acid derivative of the formula

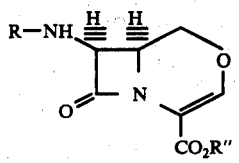   IIb wherein R and R" are as defined above, or a pharmaceutically acceptable salt thereof and, if desired, performing one or more additional steps of
1. removing by methods known per se the carboxyl-protecting group R' to produce the corresponding free acid compound of formula II;
2. converting the free acid compound of formula II to a physiologically hydrolyzed ester thereof by methods known per se; or
3. converting the free acid compound of formula II or a physiologically hydrolyzed ester thereof to a pharmaceutically acceptable salt thereof by methods known per se.

Another preferred embodiment of the present invention is the process of preparing a 7-amino 0-2-isocephem intermediate of the formula

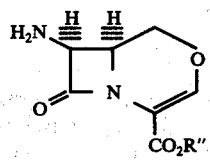   VII wherein R" is hydrogen or an easily cleavable ester carboxyl-protecting group, or a salt thereof; which process comprises selectively reducing a 7-azido intermediate of the formula

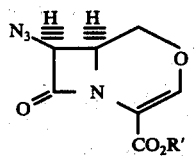   Va wherein R' is an easily cleavable ester carboxyl-protecting group and, if desired, removing protecting group R' by methods known per se to produce the corresponding free acid intermediate of formula VII and, if desired, converting the free acid form of intermediate VII to a salt thereof by methods known per se.

Another preferred embodiment of the present invention is the process of preparing a 7-azido 0-2-isocephem intermediate of the formula

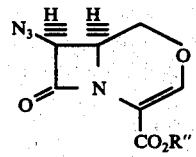   V wherein R" is hydrogen or an easily cleavably ester carboxyl-protecting group, or a salt thereof; which process comprises cyclizing by treatment with base an enol intermediate of the formula

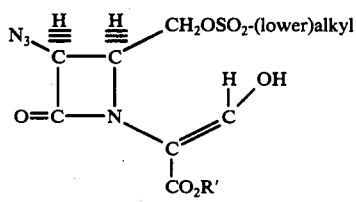

IX wherein R' is an easily cleavable ester carboxyl-protecting group and, if desired, removing protecting group R' by methods known per se to produce the corresponding free acid intermediate of formula V and, if desired, converting the free acid to a salt thereof by methods known per se.

Still another preferred embodiment of the present invention is the process of preparing a 7-azido 0-2-isocephem intermediate of the formula V wherein R" is hydrogen or an easily cleavable ester carboxyl-protecting group, or a salt thereof; which process comprises subjecting a compound of the formula

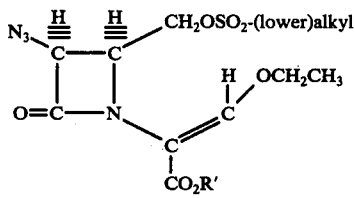

XIX wherein R' is an easily cleavable ester carboxyl-protecting group to base hydrolysis and cyclization to produce the desired carboxyl-protected intermediate of formula V and, if desired, removing protecting group R' by methods known per se to produce the corresponding free acid intermediate of formula V and, if desired, converting the free acid to a salt thereof by methods known per se.

A further preferred embodiment of the present invention is a process for the preparation of an enol intermediate of the formula

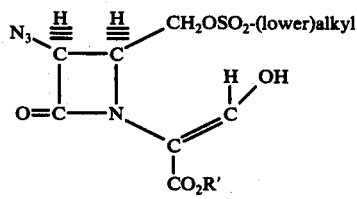

IX wherein R' is an easily cleavable ester carboxyl-protecting group; which process comprises subjecting to acid hydrolysis a derivative of the formula

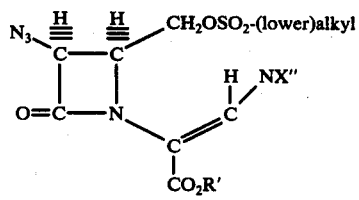

XVII wherein R' is as defined above and X" is the residue of an amine.

The ester starting material of formula XI may be prepared by the general method as illustrated in more detail in the disclosure and examples below for the case in which R' is ethyl. The ethyl ester of formula XI may be prepared by the following reaction sequence:

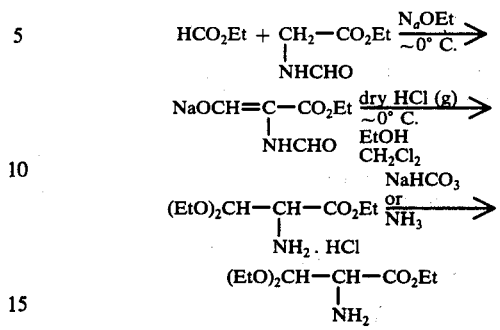

By replacing the ethyl glycinate in the above process with other desired easily cleavable esters, starting materials having other suitable carboxyl-protecting groups may be prepared.

Conversion of ester XI to the Schiff base XII may be effected by condensing the ester with cinnamaldehyde in an inert organic solvent. The Schiff base usually forms quite readily at room temperature but catalysis with the HCl salt of the amine may be used, if desired, to accelerate the reaction. The condensation reaction is carried out in a suitable inert organic solvent, e.g. benzene, ether or methylene chloride, in the presence of a drying agent, e.g. $Na_2SO_4$, $MgSO_4$, molecular sieves, etc., or, alternatively, by removing water azeotropically as with benzene.

The imine of formula XII is then condensed with an azidoacetyl halide, preferably azidoacetyl chloride, or an azioacetyl mixed anhydride in the presence of an organic base, preferably a tertiary amine such as a trialkylamine or pyridine. The reaction may be conducted in an inert organic solvent which may advantageously be a hydrocarbon or halogenated hydrocarbon solvent. A most preferred solvent for this step is methylene chloride. Best results are obtained when the reaction mixture is cooled to about 0°-5° C. At the conclusion of the reaction, the Schiff base solution is dried as with $Na_2SO_4$ and preferably evaporated to dryness. Compound IV is obtained as a mixture of diastereoisomers having the formulae

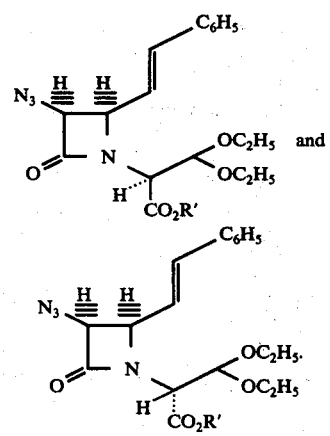

The stereochemistry of the azido and stryrryl substituents of compound IV has been shown by NMR to be exclusively cis. The diastereoisomers of IV need not be separated for use in the next step of the reaction sequence.

After formation of the cis β-lactam compound IV, the ester protecting group R' may, if desired, be removed, e.g. by saponification, and the corresponding free acid esterified to incorporate into compound IV another ester moiety R'. This optional transesterification step may conveniently be used to convert an ester such as a (lower)alkyl ester of IV to a more labile and easily removable ester such as a benzyl ester. Preferably, however, the desired easily removable ester group is incorporated into starting material XI so as to avoid the necessity of a later transesterification step.

The cis β-lactam ester of formula IV is subjected to ozonolysis in the next step of the process to produce the aldehyde of formula XVIII. Ozonolysis is conveniently conducted in an inert organic solvent, e.g. methylene chloride, with cooling, e.g. −50° to −80° C. Following ozonolysis a reagent such as dimethylsulfide, dimethylsulfoxide or triethylamine is preferably added to the reaction mixture to decompose the ozonide formed initially in the reaction.

Aldehyde XVIII is next selectively reduced to form the alcohol compound XIII. Convenient reducing agents for this step include diborane or metal hydrides such as sodium borohydride, lithium borohydride or zinc borohydride. The reduction is conducted in an inert organic solvent which most advantageously is a (lower)alkanol such as ethanol or methanol or tetrahydrofuran and preably with cooling to a temperature of about 0° to −10° C.

According to one reaction route, alcohol XIII is next converted to compound XIV by treatment with an acid anhydride, preferably acetic anhydride or trifluoroacetic anhydride, in the presence of a Lewis acid, preferably an acid selected from zinc chloride, trityl fluoroborate, triethyl oxonium fluoroborate, titanium tetrachloride, boron trifluoride or stannous chloride. The three reactants in this step are preferably used in equimolar amounts and the reaction may conveniently be performed at room temperature.

Compound XIV is hydrolyzed to alcohol XV by treatment with acid, conveniently an aqueous solution of a mineral acid, e.g. hydrochloric acid. The hydrolysis is advantageously conducted at reflux temperatures.

In the next step of this reaction route, alcohol XV is reacted with an amine, preferably a saturated cyclic secondary amine such as morpholine, piperidine or pyrrolidine, to produce the anamine compound of formula XVI. This step is conveniently effected by refluxing the alcohol and amine in an inert organic solvent, e.g. benzene, in the presence of an organic acid, e.g. acetic acid.

Enamine XVI is then reacted with a (lower)alkylsulfonating agent, preferably a methanesulfonating agent such as methanesulfonic anhydride or methanesulfonyl chloride, in the presence of an acid acceptor, preferably a tertiary amine such as a trialkylamine, e.g. triethylamine, or pyridine to produce a derivative of formula XVII. The reaction may be conducted in an inert organic solvent, e.g. methylene chloride and is conveniently carried out at room temperature.

The derivative of formula XVII is next hydrolyzed by treatment with acid to the enol intermediate of formula IX. Advantageously the hydrolysis is carried out by refluxing an aqueous solution of a mineral acid such as hydrochloric acid with compound XVII.

Enol intermediate IX is cyclized to the azido O-2-isocephem intermediate Va by treatment with a base. Examples of suitable bases for this step include an alkali metal hydride, most preferably NaH, in a suitable organic solvent, e.g. dimethylsulfoxide or dimethylformamide, triethylamine in an inert organic solvent such as methylene chloride, chloroform or (lower)alkanols, e.g. methanol or ethanol and sodium or potassium acetate in a suitable solvent such as dimethylformamide. Generally it is preferred to employ the azido 0-2-isocephem in its carboxyl-protected form in preparing the active 0-2-isocephem antibacterial agents of formula II. If desired, however, the ester group of intermediate Va may be removed by methods known per se to produce the free acid form of compound Va. The ester or free acid forms of the azido-isocephem intermediate may also be optionally converted by known methods to salts thereof.

In an alternative reaction route, alcohol XIII is reacted with a (lower)alkylsulfonating agent, preferably a methanesulfonating agent such as methanesulfonic anhydride or methanesulfonyl chloride, in the presence of an acid acceptor, preferably a tertiary amine such as a trialkylamine, e.g. triethylamine, or pyridine, to form the derivative XVIII. The reaction may be conducted in an inert organic solvent, e.g. methylene chloride, and is conveniently carries out at room temperature. Compound XVIII is then converted by treatment with an acid anhydride, preferably acetic anhydride or trifluoroacetic anhydride, in the presence of a Lewis acid, preferably an acid selected from zinc chloride, trityl fluoroborate, triethyl oxonium fluoroborate, titanium tetrachloride, boron trifluoride or stannous chloride, to compound XIX which may then be subjected to base hydrolysis to form the enolate intermediate XX. While the nature of the base is not critical in the hydrolysis step, advantageously the base is an alkali metal hydroxide such as sodium or potassium hydroxide. Enolate intermediate XX then cyclizes on removal of water and exposure to a dipolar aprotic solvent such as dimethylsulfoxide to form the 7-azido 0-2-isocephem intermediate Va.

In still another alternative reaction route, alcohol XV is converted to a (lower)alkylsulfonyl derivative XIX by reaction with a (lower)alkylsulfonating agent, preferably a methanesulfonating agent such as methanesulfonic anhydride or methanesulfonyl chloride, in the presence of an acid acceptor, preferably a tertiary amine base such as a trialkylamine, e.g. triethylamine, or pyridine, in an inert organic solvent, e.g. methylene chloride, and preferably at about room temperature. Compound XIX is subjected to base hydrolysis to form enolate XX which may be cyclized as described above to form the 7-azido 0-2-isocephem intermediate Va.

Azido-isocephem intermediate Va prepared according to any of the above procedures is selectively reduced to the 7-amino 0-2-isocephem intermediate VIIa. Preferred reducing agents for this step include chemical reducing agents selected from zinc and ammonium chloride in an inert organic solvent, e.g. methanol, and hydrogen sulfide and triethylamine in an inert oranic solvent, e.g. methylene chloride. Catalytic hydrogenation may also be employed with such selective hydrogenation catalysts as noble metals (most preferably palladium or platinum), noble metal oxides (most preferably palladium oxide or platinum oxide), or aluminum amalgam or Raney nickel, said catalysts being optionally supported on a conventional carrier such as carbon, diatomaceous earth, etc. Preferred solvents for catalytic hydrogenation are non-reducible inert solvents such as methanol, ethanol and ethyl acetate. Hydrogenation is preferably conducted at room temperature and at atmospheric or slightly elevated pressure. As in the case of the 7-azido 0-2-isocephem intermediate discussed above, compound VIIa may, if desired, be converted by methods known per se to the corresponding free carboxylic acid form or to a salt of either the esterified or free acid form. As an alternative to the stepwise reduction of the azido group and removal of the ester carboxyl-protecting group, it is also possible by choice of proper reduction conditions and protecting groups to simultaneously reduce the azido group and ester protecting group. Thus if a mild hydrogenation catalyst is used such as 10% Pd-on-charcoal or a mild chemical reducing agent such as $H_2S$ and triethylamine, the azido group is reduced to an amine but a benzyl protecting group is untouched. If a more active catalyst, however, such as 30% Pd-on-diatomaceous earth is employed, both azido and benzyl groups are reduced.

Compound VIIa or an easily cleavable ester or salt thereof is of use primarily as an intermediate in preparing the active N-acyl derivatives of formula II. Compound VIIa upon conversion to the free carboxylic acid (or a physiologically hydrolyzed ester of pharmaceutically acceptable salt of said acid or ester) also possesses antibacterial activity per se against Gram-positive and Gram-negative bacteria.

The 7-acylamido 0-2-isocephem compounds of general formula II may be prepared by N-acylation according to methods known per se of the 7-amino group of intermediate VIIa or VII. The preferred methods for preparing the active end-products of formula II will be discussed in more detail below.

According to another aspect of the present invention, there is provided a process for preparing 0-2-isocephem compounds of the formula

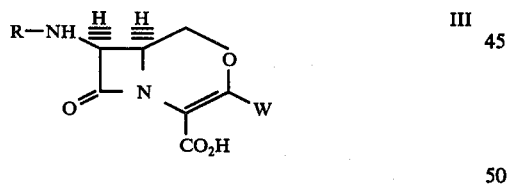

wherein R represents an acyl group and W is alkyl, preferably methyl, or aralkyl, preferably benzyl or phenethyl, and easily cleavable esters and pharmaceutically acceptable salts thereof; which process comprises the consecutive steps of 1. reacting a ketal amine of the formula

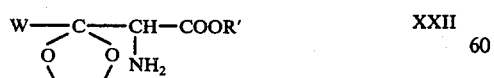

wherein R' represents an easily cleavable ester carboxyl-protecting group and W is alkyl or aralkyl with cinnamaldehyde in an inert organic solvent in the presence of a drying agent or with azeotropic removal of water to produce an imine of the formula

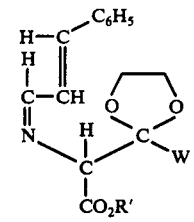

wherein R' and W are as defined above;

2. reacting said imine with an azidoacetyl halide or an azidoacetic mixed anhydride in the presence of a base to produce a cis-β-lactam compound of the formula

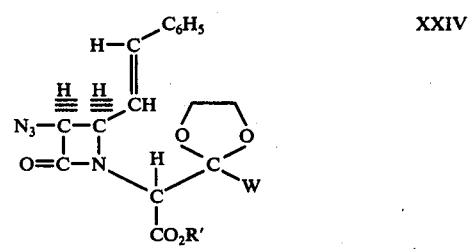

wherein R' and W are as defined above;

3. subjecting said 62-lactam compound of formula XXIV to ozonolysis to produce an aldehyde of the formula

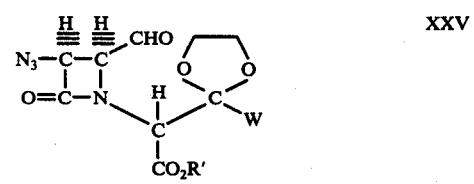

wherein R' and W are as defined above;

4. selectively reducing the aldehyde of forumula XXV to the corresponding alcohol of the formula

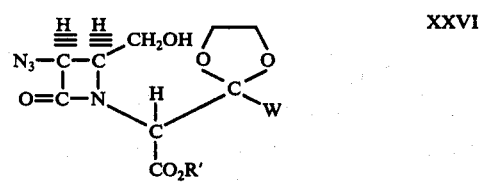

wherein R' and W are as defined above;

5. reacting said alcohol with a (lower)alkylsulfonating agent in the presence of an acid acceptor to produce a derivative of the formula

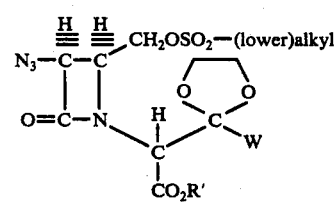

wherein R' and W are as defined above;

6. subjecting said derivative of formula XXVII to acid hydrolysis to form an enol of the forula

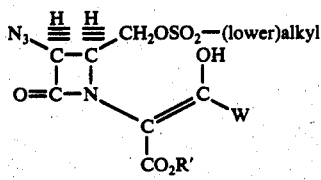

wherein R' and W are as defined above;

7. cyclizing the enol of formula X by treatment with base to produce an azido 0-2-isocephem intermediate of the formula

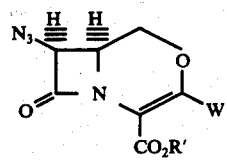

wherein R' and W are as defined above:

8. selectively reducing the azido 0-2-isocephem intermediate of formula VIa to produce a 7-amino 0-2-isocephem intermediate of the formula

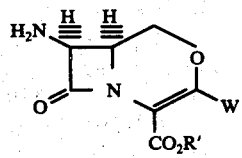

wherein R' and W are as defined above; and

9. N-acylating said 7-amino intermediate of formula VIIIa or a salt thereof with an acylating acid of the formula

wherein R represents an acyl group, or with its functional equivalent as an acylating agent for a primary amine, to produce a 7-acylamido 0-2-isocephem-4-carboxylic acid derivative of the formula

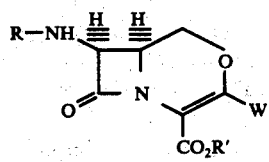

wherein R, W and R' are as defined above, or a pharmaceutically acceptable salt thereof and, if desired, performing one or more of the additional steps of 10. removing by methods known per se the carboxyl-protecting group R' to produce the corresponding free acid compound of formula III;
11. converting the free acid compound of formula III to a physiologically hydrolyzed ester thereof by methods known per se; or
12. converting the free acid compound of formula III or a physiologically hydrolyzed ester thereof to a pharmaceutically acceptable salt thereof by methods known per se.

A preferred embodiment of the present invention is the process of preparing a 7-acylamido 0-2-isocephem compound having the formula

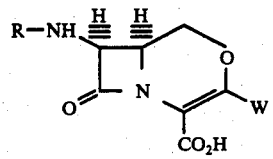

wherein R represents an acyl group and W is alkyl, preferably methyl, or aralkyl, preferably benzyl or phenethyl, and easily cleavable esters and pharmaceutically acceptable salts thereof; which process comprises N-acylating a 7-amino 0-2-isocephem intermediate of the formula

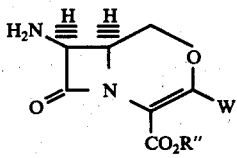

wherein R'' is hydrogen or an easily cleavable ester carboxylprotecting group R' and W is as defined above, or a salt thereof, with an acylating acid of the formula

wherein R is as defined above, or with its functional equivalent as an acylating agent for a primary amine, to produce a 7-acylamido 0-2-isocephem-4-carboxylic acid derivative of the formula

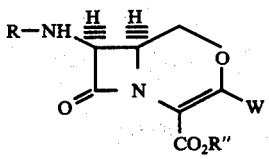

wherein R, R'' and W are as defined above, or a pharmaceutically acceptable salt thereof and, if desired, performing one or more of the additional steps of 1. removing by methods known per se the carboxyl-protecting group R' to produce the corresponding free acid compound of formula III;
2. converting the free acid compound of formula III or a physiologically hydrolyzed ester thereof by methods known per se; or
3. converting the free acid compound of formula III or a physiologically hydrolyzed ester thereof to a pharmaceutically acceptable salt thereof by methods known per se.

Another preferred embodiment of the present invention is the process of preparing a 7-amino O-2-isocephem intermediate of the formula

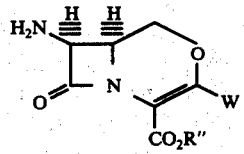

wherein W is alkyl, preferably methyl, or aralkyl, preferably benzyl or phenethyl, and R" is hydrogen or an easily cleavable ester carboxyl-protecting group, or a salt thereof; which process comprises selectively reducing a 7-azido intermediate of the formula

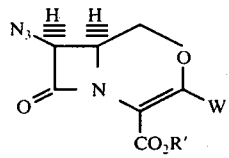
VIa wherein R' is an easily cleavable ester carboxylprotecting group and W is as defined above, or a salt thereof and, if desired, removing protecting group R' by methods known per se to produce the corresponding free acid intermediate of formula VIII and, if desired, converting the free acid to a salt thereof by methods known per se.

Another preferred embodiment of the present invention is the process of preparing a 7-azido O-2-isocephem intermediate of the formula

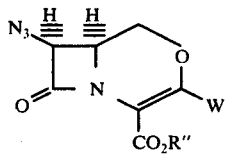
VI wherein W is alkyl, preferably methyl, or aralkyl, preferably benzyl or phenethyl, and R" is hydrogen or an easily cleavable ester carboxyl-protecting group, or a salt thereof; which process comprises cyclizing by treatment with base an enol intermediate of the formula

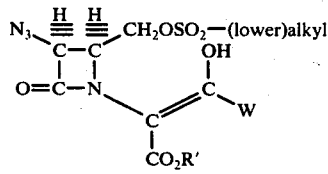
X wherein W is as defined above and R' is an easily cleavable ester carboxyl-protecting group and, if desired, removing protecting group R' by methods known per se to produce the corresponding free acid intermediate of formula VI and, if desired, converting the free acid intermediate to a salt thereof by methods known per se.

A further preferred embodiment of the present invention is a process for the preparation of an enol intermediate of the formula

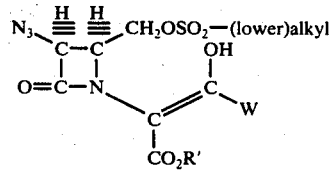
X wherein W is alkyl, preferably methyl, or aralkyl, preferably benzyl or phenethyl, and R' is an easily cleavable ester carboxyl-protecting group; which process comprises subjecting to acid hydrolysis a derivative of the formula

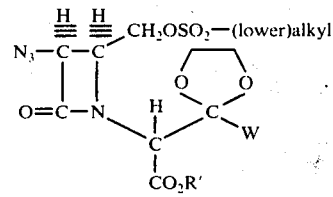

wherein R' and W are as defined above

The ketal amine starting material of formula XXII may be prepared by the following reaction sequence:

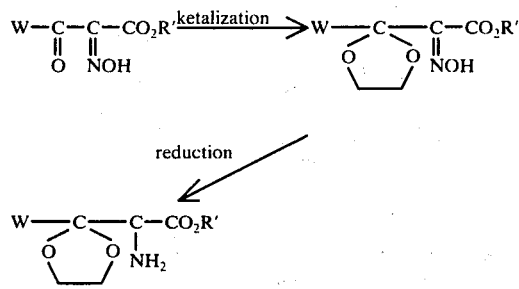

The ester oxime may be prepared according to the general method described by H. Adkins and J. Reeve, J.A.C.S., 60, 1328 (1939). The carbonyl group of the ester oxime is protected by ketalization with ethylene glycol in the presence of acid, e.g. p-toluenesulfonic acid. The ketal oxime is then selectively reduced as with aluminum amalgam by the procedure described by D. J. Drinkwater and P. W. G. Smith in J. Chem. Soc. (C), 1305, (1971). The product may be recovered as an acid addition salt, e.g. HCl salt, which may be basified to give ketal amine starting material XXII.

An alternative procedure for preparing ketal amine starting materials of formula XXII having less labile ester groups, e.g. (lower)alkyl esters such as ethyl or methyl, comprises selectively reducing the oxime group of an ester oxime of the formula

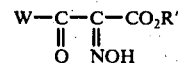

and subsequently protecting the carbonyl group by ketalization. The reduction step may be conveniently accomplished by catalytic hydrogenation and the ketalization step is carried out as described above and in the examples which follow.

Conversion of the ketal amine XXII to alcohol XXVI is effected as described above in connection with the process for preparing compounds of formula II. Compound XXIV is obtained as a mixture of diastereoisomers having the formulae

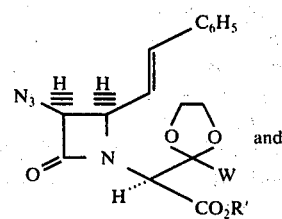
and

-continued

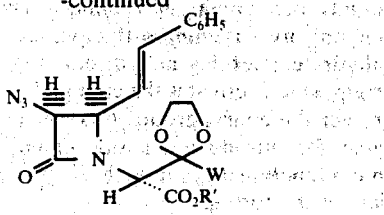

The stereochemistry of the azido and stryrryl substituents of compound XXIV has been shown by NMR to be exclusively cis. The diastereoisomers of XXIV need not be separated for use in the ozonolysis step of the reaction sequence.

Alcohol XXVI is reacted with a (lower)alkylsulfonating agent, preferably a methanesulfonating agent such as methanesulfonic anhydride or methansulfonyl chloride, in the presence of an acid acceptor, preferably a tertiary amine, e.g. triethylamine, or pyridine, to produce the derivative of formula XXVII.

The reactiom may be conducted in an inert organic solvent, e.g. methylene chloride, and is conveniently carried out at room temperature.

Enol intermediate X is produced by hydrolyzing compound XXVII under acidic conditions. Examples of suitable reagents for the ketal hydrolysis step are trifluoroacetic acid, a solution of $BF_3$ etherate and 50% perchloric acid in acetone.

Following the hydrolysis step, the enol intermediate X is cyclized by treatment with base to produce the azido O-2-isocephem intermediate VIa. Examples of suitable bases for the cyclization step include an alkali metal hydride, e.g. NaH, in a suitable organic solvent, e.g. dimethylsulfoxide or dimethylformamide, triethylamine in an inert organic solvent such as methylene chloride, chloroform or a (lower)alkanol, e.g. methanol or ethanol, and sodium or potassium acetate in a suitable solvent such as dimethylformamide. Generally it is preferred to employ the azido O-2-isocephem in the carbonyl-protected form in preparing the active O-2-isocephem antibacterial agents of formula III. If desired, however, the ester protecting group of intermediate VIa may be cleaved by methods known per se to produce the free carboxylic acid form of compound VIa. The ester or free acid forms of the azido isocephem intermediate may also be optionally converted by known methods to salts thereof.

Azido-isocephem intermediate VIa is next selectively reduced to the 7-amino O-2-isocephem intermediate VIIa by catalytic hydrogenation with such selective hydrogenation catalysts as Raney nickel, aluminum amalgam, noble metals such as preferably platinum or palladium (optionally on a carrier such as carbon), or noble metal oxides such as preferably platinum oxide or palladium oxide or by the use of chemical reducing agents such as most preferably zinc and ammonium chloride in an inert organic solvent, e.g. methanol, or hydrogen sulfide and triethylamine in an inert organic solvent, e.g. methylene chloride. Preferred solvents for catalytic hydrogenation are such nonreducible inert solvents as methanol, ethanol and ethyl acetate. Hydrogenation is preferably conducted at room temperature and at atmospheric or slightly elevated pressure. As in the case of the 7-azido O-2isocephem intermediate VIa discussed above, compound VIIIa may, if desired, be converted by methods known per se to the corresponding free carboxylic acid form or to a salt of either the esterified or free acid form.

The compounds of formula VIIIa or easily cleavable esters or salts thereof are of use primarily as intermediates in preparing the active N-acyl derivatives of formula III. Compounds of formula VIIIa, however, upon conversion to the free carboxylic acid (or a physiologically hydrolyzed ester or pharmaceutically acceptable salt of said acid or ester) also posses antibacterial activity per se against a variety of Gram-positive and Gram-negative bacteria.

The 7-acylamido O-2-isocephem compounds of formulae II and III are prepared by N-acylation according to known methods of the 7-amino group of intermediate VIIa or VIIIa with an acylating acid of the formula

R-COOH wherein R is an acyl group, or with its functional equivalent as an acylating agent for a primary amino group. The acylating agents for preparing the products of formula II and III are known, readily preparable by known methods or described herein.

Intermediates VIIa and VIIIa may be acylated either in the form of the free carboxylic acid (or salt thereof) or as an easily cleavable ester (or acid addition salt thereof). The procedures for preparing esters of carboxylic acids are disclosed in the literature and are well-known to those skilled in the art of penicilln and cephalosporin chemistry. Methods for preparing certain of the more preferred easily cleavable esters, i.e. the pivaloyloxymethyl, acetoxymethyl, methoxymethyl, acetonyl and phenacyl esters, are disclosed in U.S. Pat. No. 3,284,451 and U.K. Pat. No. 1,229,453. Preparation of the phthalidyl ester is described in South African Application 72/3799. The free acid form of intermediate VIIa and VIIIa may also be converted to a silyl ester, e.g. trimethylsilyl ester, as by the methods described in the literature, e.g. U.S. Pat. No. 3,249,622. The silyl ester carboxyl-protecting group may be easily removed following the acylation reaction by hydrolysis or alcoholysis.

Prior to the acylation reaction, any reactive substituents on the acylating acid or derivative thereof, e.g. hydroxy, carboxyl or mercapto, may be protected by use of suitable protecting or blocking groups which are well-known to those skilled in the art of β-lactam chemistry, e.g. as by acylation or silylation. When the acylating agent contains an amino functional group in the acyl moiety, the amino group is protected by a conventional amino-blocking group which may be readily removed at the conclusion of the reaction. Examples of suitable amino-protecting or blocking groups include t-butoxycarbonyl, carbobenzyloxy, 2-hydroxy-1-naphthcarbonyl, trichloroethoxycarbonyl, 2-ethoxycarbony-1-methylvinyl and 2-methoxycarbonyl-1-methylvinyl. A particularly valuable blocking group is a proton, as in the acylating agent of the formula

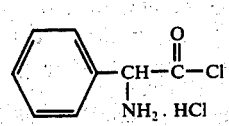

Preferred amino-protecting groups are t-butoxycarbonyl, carboboenzyloxy, the proton and a β-diketone or β-ketoester as in U.K. Pat. No. 1,123,333 or U.S. Pat.

Nos. 3,325,479 and 3,316,247, e.g. methyl acetoacetate, or a β-ketoamide as in Japan 71/24714. When the t-butoxycarbonyl, carbobenzyloxy, β-ketoester, β-diketone or β-ketoamide protecting groups are employed, it is preferred to convert the acylating acid containing the blocked amino group to a mixed anhydride, e.g. with ethyl or isobutyl chloroformate, before reaction with compounds VIIa or VIIIa or an ester or salt thereof. After the acylation coupling reaction, the amino-protecting group and any other protecting group used may be removed by methods known per se to form the desired product of formulae II or III. Thus, for example, with respect to amino-protecting groups, the t-butoxycarbonyl group may be removed by use of formic acid, the carbobenzyloxy group by catalytic hydrogenation, the 2-hydroxy-1-naphthcarbonyl group by acid hydrolysis, the trichloroethoxycarbonyl group by treatment with zinc dust in glacial acetic acid, the proton by neutralization, etc.

Acylation of a free amino group of a cephalosporin or penicillin nucleus is a well-known reaction, and any of the functional equivalents of the carboxylic acid RCOOH commonly used in penicillin or cephalosporin chemistry as acylating agents for primary amino groups may be employed in acylating intermediate VIIa or VIIIa. Examples of suitable acylating derivatives of the free acid include the corresponding acid anhydrides, mixed anhydrides, e.g. alkoxyformic anhyrides, acid halides, acid azides, active esters and active thioesters. The free acid may be coupled with compound VIIa or VIIIa after first reacting said free acid with N,N'-dimethylchloroformiminium chloride [cf. Great Britain 1,008,170 and Novak and Weichet, Experientia XXI, 6, 360(1965)] or by the use of enzymes or of an N,N'-carbonyldiimidazole or an N,N'-carbonyl ditriazole [cf. South African Specification 63/2684] or a carbodiimide reagent [especially N,N'-diisopropylcarbodiimide or N-cyclohexyl-N'-(2-morpholinoethyl)carbodiimide: cf. Sheehan and Hess, J.A.C.S., 77, 1967 (1955) ], or of alkylylamine reagent ]cf. R. Buijle and H. G. Viehe, Angew. Chem. International Edition, 3, 582, (1964) ] or of an isoxasolium salt reagent [cf. R. B. Woodward, R. A. Olofson and H. Mayer, J. Amer. Chem. Soc., 83, 1010 (1961)], or of a ketenimine reagent [cf. C. L. Stevens and M. E. Munk, J. Amer. Chem. Soc., 80, 4065 (1958)] or of hexachlorocyclotriphosphatriazine or hexabromocyclotriphosphatriazine (U.S. Pat. No. 3,651,050) or of diphenylphosphoryl azide [DPPA; J. Amer. Chem. Soc., 94, 6203-6105 (1972)] or of diethylphosphoryl cyanide [DEPC; Tetrahedron Letters No. 18, pp. 1595-1598 (1973)] or of diphenyl phosphite [Tetrahderon Letters No. 49, pp. 5047-5050 (1972)]. Another equivalent of the acid chloride is a corresponding azolide, i.e., an amide of the corresponding acid whose amide nitrogen is a member of quasiaromatic five membered ring containing at least two nitrogen atoms, i.e, imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantiative yield with liberation of carbon dioxide and one mole of imidazole. Dicarboxylic acids yield dimidazolide. The by-product, imidazole, precipitates and may be separated and the imidazolide isolated, but this is not essential. A preferred acylating agent for preparing 7-acylamido compounds containing an α-amino substitutent, e.g. α-aminophenyl, α-amino-α-thienyl, etc. is the N-carboxy anhydride (Leuch's anhydride). In this structure the group which activates the carboxyl group also serves to protect the amino group. Another preferred acylating agent for introducing a side chain containing an α-amino functional group is the acid chloride hydrochloride, of the formula

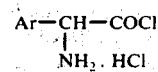

which also serves a dual function of carboxyl activation and amino protection. Mention was made above of the use of enzymes to couple the free acid with compound VIIa and VIIIa. Included in the scope of the such processes are the use of an ester, e.g. the methyl ester, of that free acid with enzymes provided by various microorganisms, e.g. those described by T. Takahashi et al., J.A.C.S., 94(11), 4035-4037 (1972) and by T. Nara et al., J. Antibiotics (Japan) 24(5), 321-323 (1971) and in U.S. Pat. No. 3,682,777. A particularly preferred coupling agent for coupling the acylating acid with compound VIIa or VIIIa (or a salt or ester thereof) is N-ethoxycarbonyl-2-ethoxy-1,2-dihydroquinoline (EEDQ) as described in J.A.C.S., 90, 823-824 and 1652-1653 (1968) and U.S. Pat. No. 3,455,929.

The particular process conditions, e.g. temperature, solvent, reaction time, etc. selected for the coupling reaction are determined by the nature of the reactants and acylation method used and are known to those skilled in the art.

The acylating agents which may be used to form the N-acyl active compounds of formulae II and III are known in the literature along with methods for their synthesis. In those cases where the acylating agent contains one or more asymmetric carbon atoms and thus exists in optically active forms, the compounds obtained using such an acylating agent are ordinarily obtained in racemic form. When the separate optical isomers are desired, the acylating agent can be resolved in a conventional manner such as by reacting the free acid with cinchonine, strychnine, brucine or the like, fractionally crystallizing to separate the diastereoisomeric salts and separately acidifying the solid phase and the liquid phase to liberate the optical isomers.

The componds of the present invention may be isolated in any of the ways customarily employed for the isolation of corresponding cephalosporin compounds. Formation of the desired pharmaceutically acceptable carboxylic acid or acid addition salt is carried out by known methods, e.g. reaction of the acid (or ester in the case of acid addition salts) with an appropriate base or acid.

At the conclusion of the acylation reaction, the product obtained may be converted (before or after removal of any protecting groups) by methods known per se to another desired product of formula II or III. Thus, the compound of formula Ii of formula III in the form of the free acid or a salt thereof may be converted by known methods to the corresponding physiologically hydrolyzed ester or pharmaceutically acceptable salt thereof. Similarly, the product of formula II or formula III in the form of an easily cleavable ester or salt thereof may be converted to the free acid product or pharmaceutically acceptable salt thereof by removal of the esterifying group, e.g. by aqueous or enzymatic hydrolysis (as with human or animal serum) or acidic or alkaline hydrolysis or by catalytic hydrogenation or by treatment with sodium thiophenoxide as taught in U.S. Pat. No. 3,284,451.

The easily cleavable esters of the compounds of formulae II and III are useful as intermediates in the production of the free acid product. The pivaloyloxymethyl, acetoxymethyl, phthalidyl, indanyl and methoxymethyl esters are also useful as active antibacterial agents since on oral administration they are rapidly hydrolyzed to the active metabolite. These esters are of particular interest because they provide on oral administration different rates and amounts of absorption and give differing concentrations of the active antibacterial agent in blood and tissues. In still another aspect of the present invention, there is provided a process for the preparation of an 0-2-isocephem-3-carboxymethylene derivative of the formula

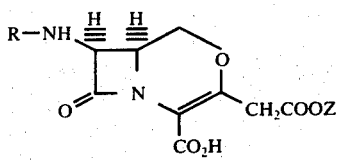

IV wherein R represents an acyl group and Z is hydrogen or the residue of an ester group and easily cleavable esters and pharmaceutically acceptable salts thereof; which process comprises 1. reacting an 0-2-isocephem compound of the formula

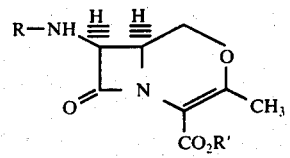

IIIb wherein R represents an acyl group and R' is an easily cleavable ester carboxyl-protecting group with carbon dioxide in the presence of a base in an inert organic solvent at a temperature in the range of about 0° C. to −80° C. to produce an acidification the compound of the formula

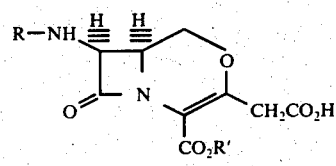

XXII wherein R and R' are as defined above, or a pharmaceutically acceptable salt thereof and optionally performing one or more of the additional steps of a. removing by methods known per se the protecting group R' to produce the corresponding 4-carboxylic acid compound of formula XXII;
b. converting the 4-carboxylic acid compound of formula XXII to a physiologically hydrolyzed ester thereof by methods known per se; or
c. converting by methods known per se the 4-carboxylic acid compound of formula XXII or a physiologically hydrolyzed ester thereof to a pharmaceutically acceptable salt thereof; and, when it is desired to produce a compound of formula IV where Z is the residue of an ester group, 2. esterifying the free carboxyl group at the 3-position of compound XXII by methods known per se to produce a compound of the formula

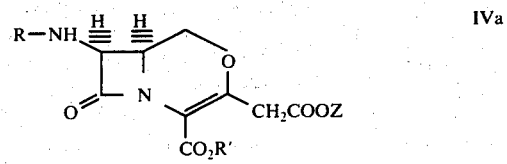

IVa wherein Z is the residue of an ester group and R and R' are as defined above, or a pharmaceutically acceptable salt thereof and, if desired, performing one or more of the additional steps of d. selectively removing by methods known per se the protecting group R' to produce the desired 4-carboxylic acid compound of formula IV wherein Z is the residue of an ester group;
e. converting the 4-carboxylic acid compound of step (d) to a physiologically hydrolyzed ester thereof by methods known per se; or
f. converting by methods known per se the 4-carboxylic acid compound of step (d) or a physiologically hydrolyzed ester thereof to a pharmaceutically acceptable salt thereof.

Acyl group R in starting material IIIb may be any organic acyl radical but is preferably selected from those acyl groups described above as preferred in connection with the compounds of general formula III. Carboxylprotecting group R' may be any easily cleavable ester group conveniently used to block a free carboxylic acid functional group. The term "easily cleavable" has the same meaning as described previously, i.e. removable by methods which do not result in any appreciable destruction of the remaining portion of the molecule. Preferred protecting groups are benzhydryl, benzyl, p-nitrobenzyl, trichloroethyl, silyl including especially trimethylsilyl, phenacyl, p-methoxybenzyl, acetonyl, (lower)alkyl including particularly methyl, ethyl and t-butyl, triphenylmethyl, methoxymethyl, acetoxymethyl, phthalidyl, indanyl and pivaloyloxymethyl.

The carboxylation reaction is carries out by reacting the carboxyl-protected compound IIIb with gaseous carbon dioxide in the presence of a base. Suitable bases for this step include sodium hydride, n-butyl lithium, t-butyl lithium, lithium dicyclohexylamine, lithium 2,2,5,6-tetramethylpiperidine and lithium diisopropylamine. The preferred bases are n-butyl lithium and t-butyl lithium. The ester IIIb is dissolved in a dry inert organic solvent, e.g. tetrahydrofuran, and dry gaseous $CO_2$ introduced into the mixture of base and IIIb solution. The reaction mixture is cooled before introduction of the $CO_2$ to a temperature in the range of 0° to −80° C. and then allowed to warm to room temperature with continued addition of carbon dioxide. Upon acidification, e.g. with a mineral acid such as aqueous HCl, compound XXII may be recovered.

Upon cleavage of carboxyl-protecting group R' to form a free 4-carboxyl group, e.g. by hydrolysis, chemical reduction or catalytic hydrogenation, the 3-carboxymethyl acids prepared by the carboxylation step or physiologically hydrolyzed esters or pharmaceutically acceptable salts of said acids or esters may be used as active antibacterial agents.

Compound XXII may also be esterified by known methods to form the desired carboxyl-protected compound of formula IVa where Z is the residue of an ester group, most preferably $C_1$-$C_6$ alkyl, e.g. methyl, ethyl, n-propyl, isopropyl, n-butyl, isobutyl, sec-butyl, t-butyl, n-pentyl, n-heptyl, etc. The ester group Z should be one which is resistant to conditions required for removal of blocking group R', e.g. resistant to hydrogenolysis. The most preferred ester, the methyl ester, may be prepared for example by reaction of compound XXII with diazomethane. The preferred lower alkyl esters may also be formed by use of the mixed anhydride reaction or by the use of dimethylformamide acetals as described in Helv. Chim. Acta., 48, 1746 (1965). Upon selective cleavage of blocking group R' by known methods, e.g. acid labile blocking groups such as t-butyl, p-methoxybenzyl or tetrahydropyranyl may be selectively removed by mild acid treatment and groups such as benzyl or p-nitrobenzyl may be selectively removed by hydrogenolysis, the intermediates of formula IVa where R' is not physiologically hydrolyzed may be converted to 4-carboxylic acid active antibacterial agents. The free acid products may optionally be converted according to known methods to physiologically hydrolyzed esters or pharmaceutically acceptable salts thereof.

The compounds and pharmaceutically acceptable salts of formuls XXII wherein R' is a physiologically hydrolyzed ester group or the de-blocked compounds of formula XXII or physiologically hydrolyzed esters or pharmaceutically acceptable salts of said acids or esters are as mentioned above active antibacterial agents. These compounds and salts have approximately the same degree of activity as the acids, physiologically hydrolyzed esters and pharmaceutically acceptable salts of formula IV, but are more difficult to isolate from the reaction mixture because of the presence of the free carboxyl group on the 3-position. For this reason, the preferred compounds and salts of formula IV are those having the esterified carboxymethylene 3-substituent, most preferably those having a $C_1$-$C_6$ alkyl radical for the Z substituent.

The pharmaceutically active compounds of the present invention are potent antibacterial agents useful in the treatment of infectious diseases in poultry and animals, including man, caused by many Gram-positive and Gram-negative bacteria. The active compounds are also of value as nutritional supplements in animal feeds and as agents for the treatment of mastitis in cattle.

The novel medicaments provided by the present invention may be formulated as pharmaceutical compositions comprising, in addition to the active ingredient, a pharmaceutically acceptable carrier or diluent. The compounds may be administered both orally and parenterally. The pharmaceutical preparations may be in solid form such as capsules, tablets or dragees, or in liquid form such as solutions, suspensions or emulsions. In the treatment of bacterial infections in man, the active compounds of this invention may be administered parenterally or orally in an amount of from about 5 to 200 mg/Kg./day and preferably about 5 to 20 mg./Kg./day in divided dosage, e.g. three or four times a day. They are administered in dosage units containing, for example, 125, 250 or 500 mg. of active ingredient with suitable physiologically acceptable carriers or excipients.

Illustrative examples of the preparation of compounds of the present invention follow. These examples are given in illustration of, but not in limitation of, the present invention. All temperatures are in degrees Centigrade. AR indicates Analytical Reagent grade. Other abbreviations include TEA for triethylamine, THF for tetrahydrofuran, mm for millimole, TLC for thin layer chromatography and EEDQ is the amide bond forming reagent having the structure

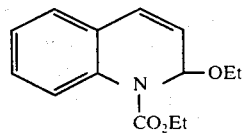

The 7-acylamido compounds prepared in the examples which follow all have the hydrogen atoms at carbons 6 and 7 cis with respect to each other and, unless indicated, the products are racemic mixtures in the sense that they are composed of equal parts of the two isomers having the following structures:

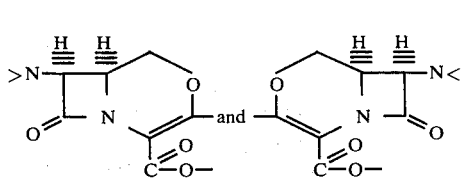

DESCRIPTION OF THE PREFERRED EMBODIMENTS

EXAMPLE 1

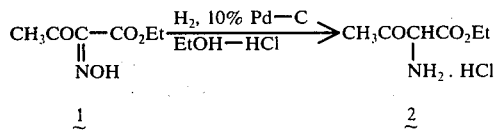

Ethyl α-oximinoacetoacetate 1 (80 g.) [Prepared according to the method of H. Adkins and J. Reeve, JACS, 60, 1328 (1939)] was dissolved in a mixture of ethanol (EtOH; 200 ml. USP) and ethanolic HCl (70 ml. of 9.28 N HCl-EtOH; 1.25 equiv.). [Amounts of HCl greater and smaller than 1.25 equivalents were found to give lower yields of 2.] 10% Palladium on carbon (8 g.) was added carefully and the mixture was hydrogenated in a Parr hydrogenation apparatus starting at 60 psig. After absorption of the theoretical amount of hydrogen (1 – 2 hr.) the catalyst was filtered off and washed with EtOH. The EtOH was removed in vacuo at 40 – 50° leaving a thick red-brown oil. The oil was diluted with 8 vols. of acetone (AR) with vigorous stirring. Yellow crystals of the amine hydrochloride 2 separated out on cooling, 49 g. (55%), m.p. 122°–123° (cor.) [lit m.p. = 114°–116° uncor.; (W. G. Laver et al., J. Chem. Soc., (1959), 1474.] [Yields ranged from 45 – 70% according to the scale of the reaction.] This material was used without further purification.

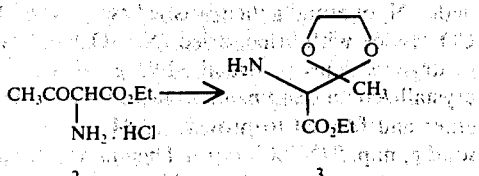

To a mixture of ethylene glycol (1.75 kg., 28.2 mole) and p-toluenesulfonic acid monohydrate (210 g.; 1.95 mole) which had been warmed to 90°, amine hydrochloride 2 (460 g.; 2.54 mole) was added with vigorous mechanical stirring. The mixture was stirred for 40 min. at 90°*. The mixture was then poured into a mixture of water (2 l), conc. NH₄OH (650 ml.), and ice (1 l), and extracted four times with 500 ml. CH₂Cl₂. The combined CH₂Cl₂ extracts were washed with brine, dried (Na₂SO₄), and evaporated to give 491 g. of a dark red oil. The oil was diluted to 1.8 l with Et₂O (USP), cooled in an ice bath, and EtOH sat'd with HCl gas was added until the pH reached 2-3. The resulting solid was collected by filtration and washed with Et₂O to yield 398 g. 3 hydrochloride as a light yellowish solid (70%) m.p. 153°-6° (cor.). An analytical sample of 3 hydrochloride was recrystallized from 2-propanol-Et₂O, white crystals, m.p. 158°-160° (cor.).

* Reaction times shorter and longer than 40 min. at 90° were examined and found to give poorer results.

Anal. Calc'd for $C_8H_{15}NO_4 \cdot HCl$: C, 42.58; H, 7.15; N, 6.21. Found: C, 42.40; H, 7.24; N, 6.37.

The free base of 3 is conveniently prepared from its hydrochloride by basification with conc. NH₄OH and extraction with CH₂Cl₂.

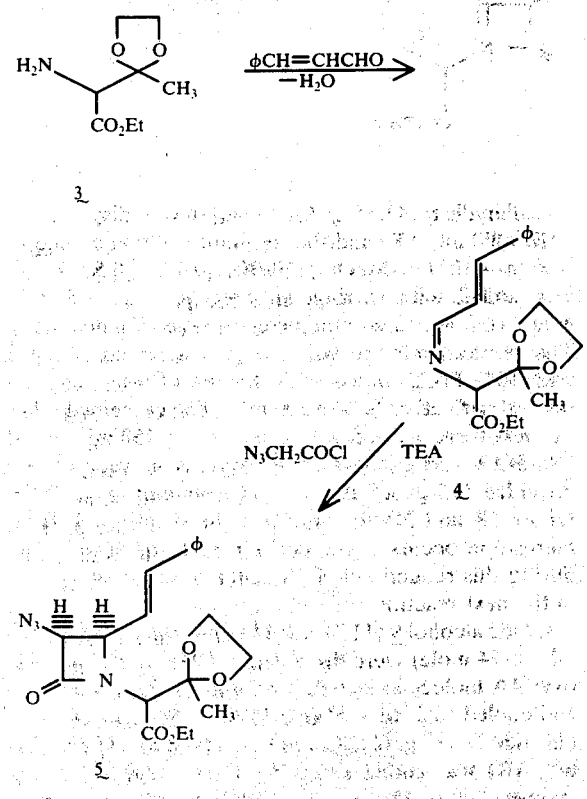

A mixture of ketal amine 3 (123 g.; 0.65 mole), cinnamaldehyde (85.9 g.; 0.65 mole), and CH₂Cl₂ (3.6 l; AR dried over 4A molecular sieve) was refluxed through a Soxhlet apparatus containing 200 g. of 4A molecular sieve for 2 hr. The CH₂Cl₂ was then removed on a rotary evaporator at 40° with the final traces of CH₂Cl₂ being removed by pumping down to 0.5 mm. at 25° for 20 minutes. NMR indicated complete formation of imine 4 which was used directly in the next step.

Crude imine 4 (ca. 0.65 mole) was dissolved in CH₂Cl₂ (3 l; AR dried over 4A molecular sieve), TEA (99.65 ml. 1.1 equiv.) was added, and the solution was placed under N₂ and cooled to 3°-4° with an ice bath. A solution of azidoacetyl chloride (85.19 g, 1.1 equiv.) in CH₂Cl₂ (500 ml.) was added with stirring over 4 hr. The reaction mixture was stirred overnight at 25° and then refluxed for 1 hr. The reaction mixture was cooled, washed with 10% HCl, then with brine, and dried over Na₂SO₄ to give 267 g. of a dark oil which NMR indicated contained 96 weight % of 5, (245 g.; 98%). Anal. sample was recrystallized from methanol, white solid, m.p. 81.5° - 82.5° (cor.)

Anal. Calc'd for $C_{19}H_{22}N_4O_5$: C, 59.06; H, 5.94: N, 14.50. Found: C, 59.08; H, 5.73; N, 14.58.

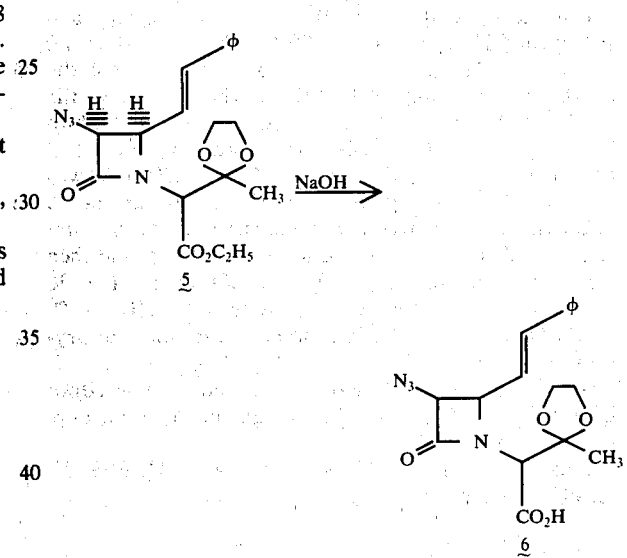

Ethyl ester 5 (64.31 g; 0.168 moles) was dissolved in 700 ml. THF in a 2 l. 3 necked RB flask equipped with magnetic stirring, a thermometer, an addition funnel and a reflux condenser. There was added 670 ml. of 0.25 N NaOH solution (0.168 moles) at such a rate as to hold the temperature around 25° (took 1 hr.). Stirred at 25° until TLC showed that 5 had completely reacted (0.75 - 1.25 hr.). The reaction mixture was carefully acidified to pH 3 with conc. HCl, sat'd with salt, and extracted with CH₂Cl₂ (3 times). The CH₂Cl₂ extracts were washed with brine, dried (Na₂SO₄) and evaporated in vacuo. The residue was dissolved in Et₂O and extracted with 10% NaHCO₃ solution until the extracts were colorless. The combined basic extracts were washed twice with Et₂O, then carefully acidified to pH 3 with conc. HCl, sat'd with salt and extracted with CH₂Cl₂. The CH₂Cl₂ extract was washed with brine, dried (Na₂SO₄) and evaporated to dryness in vacuo to give 51.86 g. (86%) of 6 as a brown solid. Recrystallization from benzene provided an anal. sample as white needles, m.p. 131-1.5° dec. (cor.).

Anal. Calc'd for $C_{17}H_{18}N_4O_5$: C, 56.98; H, 5.06; N, 15.64. Found: C, 57.06; H, 5.13; N, 15.78.

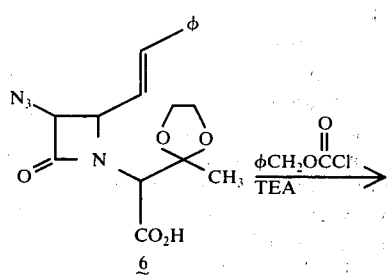

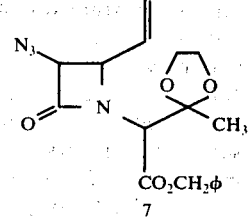

Carboxylic acid 6 (128.01 g; 0.358 mole) was dissolved in CH$_2$Cl$_2$ (1 l.) and TEA (39.8 g; 0.394 mole) was added [The carboxylic acid 6 referred to was the crystalline solid, m.p. 131°-131.5°, which is one of the isomers.]. The mixture was cooled in an icesalt bath to 3° and then a mixture of benzyl chloroformate (67.5 g. of 88.6 weight %; 0.394 mole) and CH$_2$Cl$_2$ (200 ml.) was slowly added keeping the reaction temperature at 3°. After the addition was complete, the reaction mixture was stirred at ambient temperature for 30 min. and then refluxed gently until evolution of CO$_2$ ceased (ca. 30 min.). Worked up by washing with 10% HCl, 10% NaHCO$_3$, brine, dried (Na$_2$SO$_4$) and evaporated to dryness in vacuo to yield 161.10 g. (100%) of crude 7. Crystallized from benzene-petroleum ether (30 - 60) to give 143.60 g. (99%) of 7 as a light beige solid, m.p. 65.5° - 66.5° (cor.).

Anal. Calc'd for C$_{24}$H$_{24}$N$_4$O$_5$: C, 64.27; H, 5.39; N, 12.49. Found: C, 64.13; H, 5.36; N, 12.48.

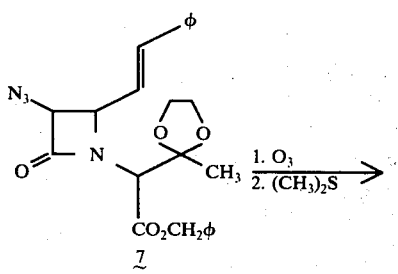

Styryl β-lactam 7 (36.36 g; 81.24 mm) [The styryl β-lactam 7 used in this experiment was principally one of the possible isomers.] was dissolved in CH$_2$Cl$_2$ (300 ml.), cooled to −50° to −60° in a dry ice-acetone bath, and ozonized until a faint blue color appeared. The solution was then flushed with O$_2$ until the blue color faded. (CH$_3$)$_2$S (31.87 ml; 5 equiv.) was added to the −50° solution, which was then allowed to slowly reach 25° as the cooling bath gradually melted. Kept at 25° under N$_2$ overnight then washed twice with 1% NaHCO$_3$, twice with brine, dried (Na$_2$SO$_4$) and evaporated to dryness. This provided 32.92 g. of 8 an oil which crystallized on standing. This material was slurried with ether and filtered to provide 18.84 g. (69%) off-white solid 8, m.p. 97°-100° (cor.). The analytical sample was recrystallized from ether, white crystals, m.p. 101°-2° (cor.).

Anal. Calc'd for C$_{17}$H$_{18}$N$_4$O$_6$: C, 54.54; H, 4.84; N, 14.96. Found: C, 54.75; H, 4.87; N, 14.89.

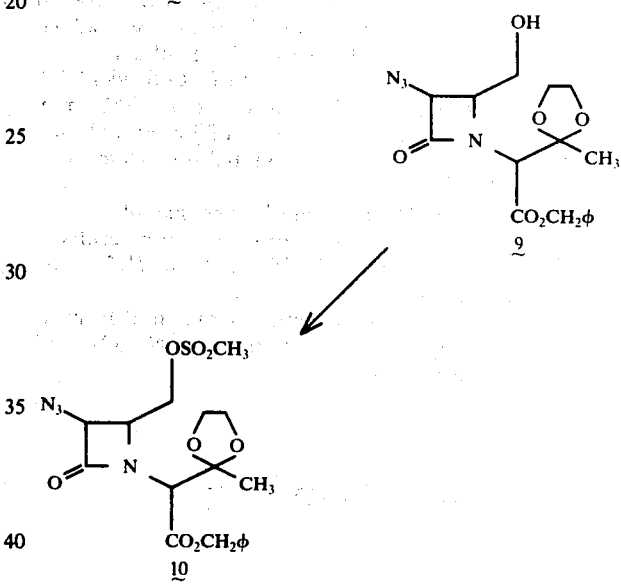

Aldehyde 8 (43.15 g; 0.115 mole) was dissolved in THF (400 ml; AR) and the resultant solution cooled to −5° to −10° (ice-MeOH). NaBH$_4$ (2.192 g; 0.576 mole) was added, with stirring, in three portions. After 25 min., TLC indicated complete reaction of aldehyde 8. The reaction mixture was carefully acidified to pH 3 with 10% HCl, diluted with 100 ml. of brine, and extracted with ether (4 ×'s 200 ml.). The combined ether extracts were washed with brine (2 ×'s 150 ml.), dried (Na$_2$SO$_4$), and evaporated to dryness in vacuo. This provided 48.7 g. of 9 as a red oil (containing some THF) whose IR and NMR confirmed the structure 9; [Epimerization occurs at the position α to the ester group during this reduction.]. This material was used as such in the next reaction.

Crude alcohol 9 (42.37 g; 0.113 mole) and TEA (17.07 ml.; 0.124 mole) were dissolved in CH$_2$Cl$_2$ (400 ml. AR over 4A molecular sieve), placed under N$_2$ atmosphere and cooled to 0° to −5° (ice-MeOH). Methanesulfonyl chloride (14.15 g, 0.124 mole) dissolved in CH$_2$Cl$_2$ (100 ml, AR) was added over 15 minutes. After 1 hr. at ambient temp. the reaction was ca. 80% complete (TLC). After 3 hours, the reaction mixture was washed with water and then with brine, dried over Na$_2$SO$_4$ and evaporated to provide 56.1 g. of brown oil. This oil was dissolved in the minimum amount of benzene and chromatographed over 700 g. of activated alumina using EtOAc-Et₂O (1:3) as eluting solvent. 30 g. of pure crystalline mesylate 10 was obtained from the first liter of eluent. 4.2 g. of slightly impure mesylate was obtained as a forerun. Total yield = 66% from 8. Anal. sample was crystallized from benzene-ether, white crystals, m.p. 97°–9° (cor.).

Anal. Calc'd for C₁₈H₂₂N₄O₈S: C, 47.61; H, 4.88; N, 12.34. Found: C, 47.56; H, 4.93; N, 12.43.

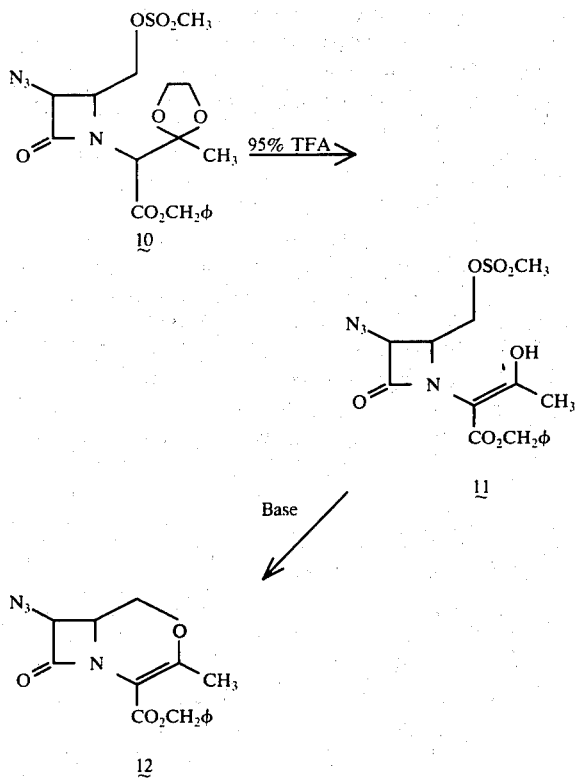

Ketal 10 (3.19 g; 6.43 mm) was placed in a 100 ml. three-necked round bottom flask equipped with magnetic stirring. 95% TFA (30 ml.) [95% TFA was prepared by adding 5 ml. of water to a 100 ml. graduated cylinder and diluting to 100 ml. with glacial TFA.] was added and the solution was stirred at ambient temp. (ca. 25°) for 2 hr. At this point NMR examination of an aliquot from the reaction mixture showed complete reaction. The mixture was diluted with 10 vols. of brine and extracted 3 times with 100 ml. (each) of CH₂Cl₂. The combined extracts were dried (Na₂SO₄) and evaporated to dryness in vacuo leaving 3.17 g. of 11 as a heavy brown oil.

NMR confirmed the pressure of enol 11.

This material was used as such in the next reaction.

Crude enol 11 (described above) (12.02 g; ca. 29.44 mm) was dissolved in CH₂Cl₂ (100 ml.) and TFA (4.1 ml; 29.44 mm) added. The mixture was refluxed under a CaCl₂ drying tube for 2 hr, then washed with 10% HCl, brine and dried (NaSO₄). Evaporation left 8.56 g. of 12 as a light brown oil. This material was taken up in CH₂Cl₂ and filtered through ca. 100 g. of silicic acid powder. Evaporation of the filtrate and Et₂O washings gave 6.58 g. of 12 (80.5% from 11) as a light beige solid. An analytical sample was recrystallized once from ether to give white crystals, m.p. 87°–88° (cor.).

Anal. Calc'd for C₁₅H₁₄N₄O₄: C, 57.32; H, 4.49; N, 17.83. Found: C, 57.31; H, 4.58; N, 17.67.

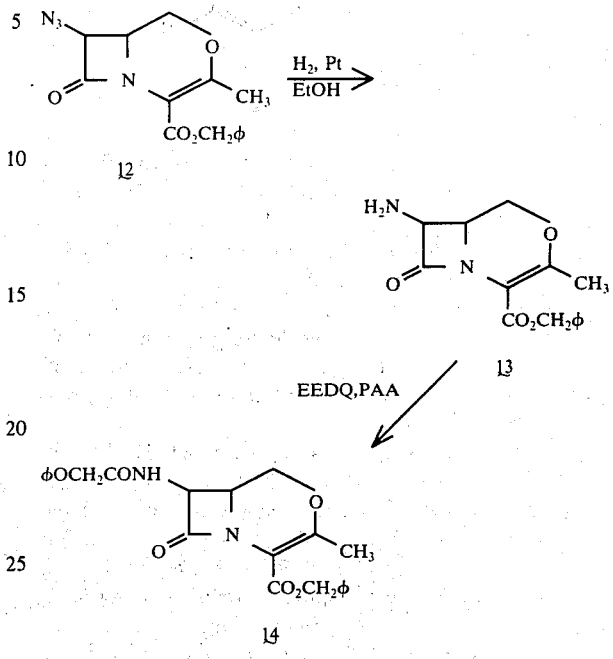

Azido O-2-isocephem 12 (201 mg; 0.64 mm) was dissolved in absolute EtOH (35 ml.), 87% PtO₂ (100 mg.) was added and the mixture was hydrogenated at atmospheric pressure. The theoretical amount of hydrogen (for PtO₂ reduction) was absorbed in 7 min. and the reaction was stopped to avoid hydrogenolysis of the benzyl ester. The catalyst was filtered off and washed with 2 vol. of EtOH. Evaporation of the EtOH provided 0.19 g. of 13 as a yellowish oil. TLC showed no 12. This oil was used immediately in the next step.

Crude amine 13 (0.19 g; 0.64 mm) was dissolved in CH₂Cl₂ (20 ml.) and phenoxyacetic acid (PAA) (97.4 mg; 0.64 mm) and EEDQ (158 mg; 0.64 mm) were added. The reaction mixture was allowed to stir at 25° for 1 hr. and then it was washed 2 times with 1% NaHCO₃, 2 times with 10% HCl, once with 3 vols. of brine, dried (Na₂SO₄) and evaporated to dryness in vacuo. This provided 0.18 g. of 14 as a yellowish gum which was triturated with dry Et₂O. The Et₂O triturant was cooled at 0° overnight. The resultant crystals were collected by filtration and washed once with petroleum ether (30°–60°) to give white crystals of 14, m.p. 133°–135° dec. (cor.).

Anal Calc'd for C₂₃H₂₂N₂O₆: C, 65.39; H, 5.25; N, 6.63. Found: C, 65.22; H, 5.31; N, 6.86.

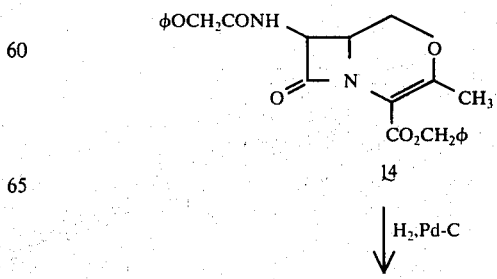

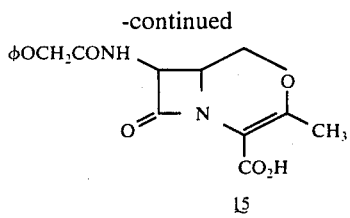

15

Benzyl ester 14 (100 mg; 0.237 mm) was dissolved in a mixture of absolute EtOH (10 ml.) and THF (7 ml.). 10% Pd-C (100 mg.) was carefully added and the mixture was hydrogenated at atmospheric pressure. Hydrogen uptake was complete after ca. 7 min. The catalyst was filtered off and washed once with EtOH. The EtOH was removed in vacuo leaving 90 mg. of partly crystalline residue. The residue as crystallized from acetone-ether to provide off-white crystals of 15, m.p. 171°–172° dec. (cor.).

Anal. Calc'd for $C_{16}H_{16}N_2O_6$: C, 57.83; H, 4.85; N, 8.43. Found: C, 57.67; H, 4.97; N, 8.34.

A sample of compound 15 prepared above which can be named 7β-phenoxyacetamido-3-methyl-O-2-isocephem-4-carboxylic acid (called BC-L8) after solution in water and dilution with Nutrient Broth was found to exhibit the following Minimum Inhibitory Concentrations (M.I.C.) in mcg./ml. versus the indicated microorganisms as determined by overnight incubation at 37° C. by Tube dilution. One old, orally absorbed cephalosporin (cephalexin) was included.

Table 1

| | M.I.C. in mcg./ml. | |
|---|---|---|
| Organism | BC-L8 | Cephalexin |
| D. pneumoniae +5% serum* | A9585 | .5 | .6 |
| Str. Pyogenes +5% serum* | A9604 | .5 | .6 |
| S. aureus Smith++ | A9537 | .5 | 1.3 |
| S. aureus Smith++ +50% serum | A9537 | 2 | 2.5 |
| S. aureus BX1633-2 at 10⁻³ dil'n | A9606 | 2 | 1 |
| S. aureus BX1633-2 at 10³¹·² dil'n | A9606 | 32 | 2 |
| Sal. enteritidis++ | A9531 | 8 | 2 |
| E. coli Juhl++ | A15119 | 63 | 4 |
| E. coli++ | A9675 | 250 | 16 |
| K. pneumoniae++ | A9977 | 32 | 4 |
| K. pneumoniae++ | A15130 | 500 | 16 |
| Pr. mirabilis++ | A9900 | 16 | 4 |
| Pr. morganii++ | A15153 | 500 | >125 |
| Ps. aeruginosa++ | A9843A | 500 | >125 |
| Ser. marcescens++ | A20019 | 500 | >125 |
| Ent. cloacae | A9656 | 500 | >125 |
| Ent. cloacae | A9657 | 63 | 2 |
| Ent. cloacae | A9659 | 500 | 125 |
| S. aureus meth.- resist; at 10⁻³ dil'n | A15097 | 32 | 16 |

*50% Nutrient Broth - 45% Antibiotic Assay Broth
  at 10⁻⁴ dilution.

EXAMPLE 2

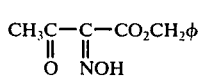

16

Benzyl Oximino-Acetoacetate

The procedure was essentially the same as that described for the corresponding ethyl ester by H. Adkins and J. Reeve, JACS 60, 1328 (1938).

In a three necked one liter flask, fitted with a thermometer, a dropping funnel and a magnetic stirrer were placed 173 g. (0.9 mole) of benzyl acetoacetate [The benzyl acetoacetate was prepared as described by Baker et al., J. Org. Chem. 17, 91 (1952)] and 130 ml. of glacial acetic acid. The contents were cooled in an ice-salt bath and a solution of 69 g. (1 mole) of sodium nitrite in 130 ml. of water was added over a period of half an hour; the temperature was kept at 0° to 10° C. After the reaction mixture was stirred for one hour at room temperature, 400 ml. of water was added and the stirring was continued for an additional two hours. The reaction mixture was extracted three times with 200 ml. portions of diethyl ether. The diethyl ether extracts were combined, washed once with water, three times with saturated sodium bicarbonate solution and once with brine. After drying over anhydrous sodium sulfate, the diethyl ether solution was evaporated leaving 16 as a clear oil which solidified upon trituration with petroleum ether (30°–60°) to give 186.5 g. (93.2%) of white solid. Its NMR spectrum was consistent with the assigned structure. Generally the product was used as such in subsequent reaction but it can be recrystallized from toluene, m.p. 81°–82° C.

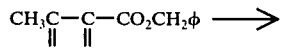

16

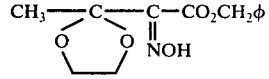

17

Benzyl Oximino-Acetoacetate Ethylene Ketal

In a two liter flask fitted with a Dean Stark water separator and a condenser were placed 186.5 g. (0.85 mole) of benzyl oximino-acetoacetate (17), 62 g. (1 mole) of ethylene glycol, 800 ml. of benzene (reagent grade) and 2 g. of toluenesulfonic acid. The reaction mixture was boiled at reflux until 15 ml. of water was removed (3 hours). The benzene solution was washed once with saturated sodium bicarbonate solution and once with brine. After drying over anhydrous sodium sulfate, the benzene solution was evaporated, leaving 212 g. (94%) of 17 as a light yellow oil. Its NMR spectrum was consistent with the assigned structure. Generally the compound was used as such in subsequent reaction but one of the isomers can be crystallized in 35% yield from toluene-petroleum ether, m.p. 52° C.

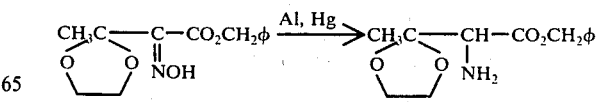

17  18

Benzyl Amino-Acetoacetate Ethylene Ketal (18)

[The procedure was essentially the same as that described for the reduction of unsaturated hydroxyimino ethyl esters by D. J. Drinkwater and P. W. G. Smith, J. Chem. Soc. (C), 1305 (1971).] [Aluminum amalgam as prepared essentially the same as that described in "Vogel" except the following modifications:

A. 5% NaOH was used.
B. The second washing with ethanol was omitted.
C. Dry diethyl ether was used for washing and most of the water must be drained.]

[Vogel "Practical Organic Chemistry" 3rd Edition. Longemans Green & Co., London (1957) p. 198.]

Aluminum amalgam (from 27 g. of aluminum foil) freshly prepared in a three-necked one liter flask was covered with 500 ml. of diethyl ether. The flask was fitted with a mechanical stirrer, a condenser, and a dropping funnel. 132.5 g. (0.5 mole) of benzyl oximino-acetoacetate ethylene ketal (17) in 300 ml. of wet diethyl ether was added dropwise at such a rate as to maintain boiling at reflux. After stirring for four hours, the reaction mixture was filtered through a Buchner funnel. The filtrate was evaporated leaving 110 g. of 18 as a yellowish oil. The oil was picked up in 800 ml. of dry diethyl ether and dry hydrogen chloride was passed in to give 108 g. of white hydrochloride salt of 18 which was collected, m.p. 157°–158° C.

To obtain the free base 18, the hydrochloride salt was suspended in 500 ml. of diethyl ether, concentrated ammonium hydroxide was added with shaking until most of the solid went into solution, then washed twice with brine. After drying over anhydrous magnesium or sodium sulfate, the solvent was evaporated leaving 90 g. of 18 as a colorless oil (71%). Its NMR spectrum was consistent with the assigned structure.

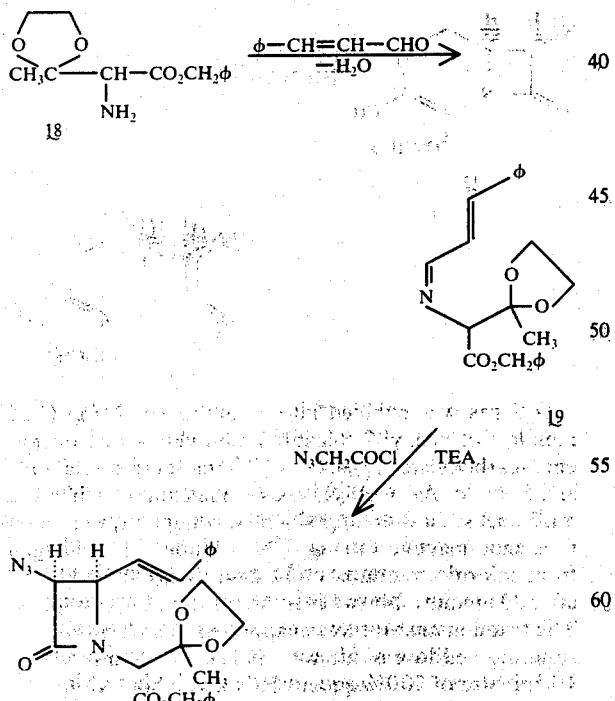

Schiff Base Formation: In a one liter flask fitted with a Dean Stark water separator and a condenser were placed 70.3 g. (0.28 mole) benzyl aminoacetoacetate ethylene ketal (18), 37 g. (0.28 mole) cinnamaldehyde and 750 ml. of methylene chloride. The mixture was boiled at reflux for half an hour and then 400 ml. of methylene chloride was distilled and removed through the Dean Stark water separator. The concentrated solution was first dried over anhydrous sodium sulfate and then evaporated completely on an evaporator to drive the reaction to completion.

The residual, oily 19 was checked by NMR to ensure complete Schiff base formation before continuing on the next step.

β-Lactam Formation: The freshly prepared Schiff base (19) was diluted with 600 ml. of methylene chloride and cooled to 0° C. (ice-salt bath). [All the methylene chloride used in the cyclo addition reaction was reagent grade which was first dried over molecular sieve (Type 4A) and then over anhydrous calcium chloride.] 31.1 g. (0.308 mole) of triethylamine was added and followed by a solution of 3.2 g. (0.308 mole) of azido-acetyl chloride in 362 ml. of methylene chloride adding dropwise at 0° C. over a period of one hour. The reaction mixture was stirred for an additional hour at room temperature and then evaporated on a flash evaporator at reduced pressure while being heated on a 35° C. water bath; this operation is necessary to ensure complete β-lactam formation. The residue was diluted with 500 ml. of diethyl ether and filtered. The filtrate was washed twice with brine and dried over anhydrous sodium sulfate. Evaporation of this solution yielded 117.5 g. (95%) of product 20. Its NMR and IR spectra were consistent with the assigned structure. Generally, the product was used as such in subsequent reaction but one of the isomers can be crystallized from diethyl ether.

Compound 20 is identical with compound 7 prepared in Example 1 and is reacted according to the procedures of Example 1 to produce benzyl 7β-amino-3-methyl-Δ³-O-2-isocephem-4-carboxylate having formula

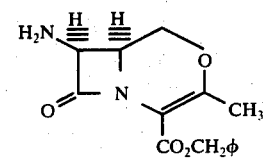

A mixture of amine 13 (430 mg.; 1.49 mmole), N-carbobenzoxy-D(−)-phenylglycine (422 mg.; 1.49 mmole), EEDQ (368 mg.; 1.49 mmole) and 30 ml. CH$_2$Cl$_2$ was stirred at 25° for 1 hour. It was then washed with 10% HCl, 1% NaHCO$_3$ and brine and dried over Na$_2$SO$_4$. Evaporation in vacuo gave 0.85 g. of a white foam which was crystallized from ether-pentane and then from MeOH.

Anal. Calc'd for C$_{31}$H$_{29}$N$_3$O$_7$·0.5 H$_2$O: C, 65.95; H, 5.36; N, 7.44. Found: C, 66.12; H, 5.30; N, 7.57.

The white foam was characterized by IR and NMR to be the N-protected compound of formula

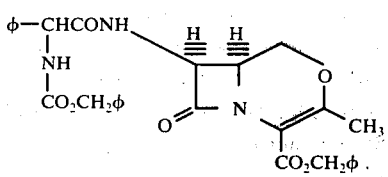

A mixture of the above N-protected intermediate (283 mg.), 600 mg. of 30% Pd-diatomaceous earth and 10 ml. of ethanol was hydrogenated at 25° at 50 psig in a Parr hydrogenator. After 0.5 hour, the catalyst was filtered off and the filtrate was evaporated to dryness in vacuo. The resultant residue was covered with $CHCl_3$ and then HCl gas was introduced. Addition of ether produced a precipitate which was filtered off and dried in vacuo. The product, a yellowish solid, decomposed at 177°–182° (corrected) and was characterized by IR and NMR as 7β-(D-α-aminophenylacetamido)-3-methyl-Δ³-O-2-isocephem-4-carboxylic acid hydrochloride (called BC-L9) of the formula

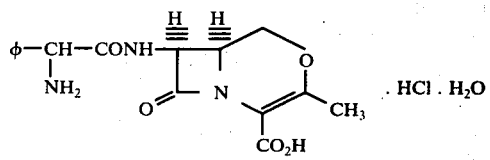

Anal Calc'd for $C_{16}H_{17}N_3O_5·HCl·H_2O$: C, 49.81; H, 5.22; N, 10.89. Found: C, 49.76; H, 5.21; N, 9.11.

A sample of BC-L9 after solution in water and dilution with Nutrient Broth was found to exhibit the following Minimum Inhibitory Concentrations (M.I.C.) in mcg./ml. versus the indicated microorganisms as determined by overnight incubation at 37° C. by tube dilution. One old, orally adsorbed cephalosporin (cephalexin) was included.

Table 2

| Organism | M.I.C in mcg./ml. | |
| --- | --- | --- |
| | BC-L9 | Cephalexin |
| D. pneumoniae +5% serum* | A9585 | .5 | .3 |
| Str. pyogenes +5% serum* | A9604 | .5 | .3 |
| S. aureus Smith++ | A9537 | 2 | 1.3 |
| S. aureus Smith++ +50% serum | A9537 | 16 | 2.5 |
| S. aureus BX1633-2 at $10^{-3}$ dil'n | A9606 | 8 | 1 |
| S. aureus BX1633-2 at $10^{-2}$ dil'n | A9606 | 32 | 2 |
| S. aureus meth.-resist; at $10^{-3}$ dil'n | A15097 | 32 | 16 |
| Sal. enteritidis++ | A9531 | 16 | 4 |
| E. coli Juhl++ | A15119 | 32 | 4 |
| E. coli++ | A9675 | 63 | 8 |
| K. pneumoniae++ | A9977 | 16 | 4 |
| K. pneumoniae++ | A15130 | 63 | 16 |
| Pr. mirabilis++ | A9900 | 63 | 8 |
| Pr. morganii++ | A15153 | 250 | >125 |
| Ps. aeruginosa++ | A9843A | >500 | >125 |
| Ser. marcescens++ | A20019 | 500 | >125 |
| Ent. cloacae | A9656 | 500 | >125 |
| Ent. cloacae | A9657 | 32 | 4 |
| Ent. cloacae | A9659 | 125 | >125 |

*50% Nutrient Broth - 45% Antibiotic Assay Broth
at $10^{-4}$ dilution.

EXAMPLE 3

7β-Amino-3-methyl-Δ³-O-2-isocephem-4-carboxylic acid

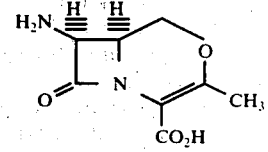

A mixture of benzyl 7β-azido-3-methyl-Δ³-O-2-isocephem-4-carboxylate (314 mg.; 1 mmole), 30% Pd-diatomaceous earth (274 mg.) and 25 ml. of absolute EtOH was hydrogenated at 25° and atmospheric pressure. Hydrogen uptake was complete after 20 minutes. The reaction mixture was then warmed to 40°, the catalyst was filtered off and washed with 1 volume of EtOH. The combined filtrate and washings were evaporated to dryness in vacuo to provide 140 mg. (71%) of white powdery residue which was identified by IR and NMR as the title product. Decomp. >ca. 209° (cor).

Anal. Calc'd for $C_8H_{10}N_2O_4·0.5H_2O$: C, 46.38; H, 5.35; N, 13.52. Found: C, 46.86; H, 5.35; N, 13.58.

A sample of the above compound (called BC-L61) was found to inhibit S. aureus A9537 at a concentration of >125 mcg./ml., E. coli A15119 at a concentration of >125 mcg./ml., D. pneumoniae A9585 at a concentration of >8 mcg./ml. and St. pyogenes at a concentration of >8 mcg./ml.

EXAMPLE 4

Benzyl 7β-Amino-3-methyl-Δ³-O-2-isocephem-4-carboxylate

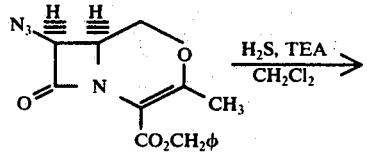

12

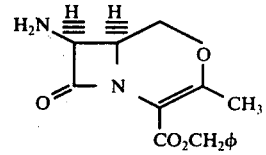

$H_2S$ gas was bubbled into a solution of 2.0 g. (6.35 mmoles) of benzyl-7-β-azido-3-methyl-Δ³-O-2-isocephem-4-carboxylate (12),4.2 ml. (30 mmole) triethylamine, and 50 ml. of AR methylene chloride contained in a 100 ml. 3 necked flask equipped with a condenser, a gas inlet tube and magnetic stirring. The solution color changed from colorless to orange and a gas ($N_2$) is evolved. TLC after 20 minutes showed that the reaction was complete. The reaction mixture was evaporated to dryness and the resulting yellow residue was shaken three times with a 1:1 mixture of 10% aqueous HCl and ether. Almost all of the residue goes into solution. The aqueous layer was separated and the ether layer (yellow colored) was washed with 10% aqueous HCl. The combined HCl phases were washed once with ether and then carefully alkalized with solid $NaHCO_3$. The alkalized aqueous phase was extracted twice with CH$_2$Cl$_2$. The CH$_2$Cl$_2$ extracts were combined, washed twice with saturated brine, dried (Na$_2$SO$_4$) and evaporated to dryness in vacuo. This provided 1.25 g. (68%) of a gummy residue (some black impurities) which crystallized upon standing overnite. NMR on this material indicates a purity of at least 95%. The solid could be recrystallized from ether to give a white solid, mp. 91°-92° (cor).

Anal. Calc'd for C$_{15}$H$_{16}$N$_2$O$_4$: C, 62.49; H, 5.59; N, 9.72. Found: C, 62.54; H, 5.51; N, 9.65.

EXAMPLE 5

7β-Phenoxyacetamido-3-benzyl-Δ$^3$-O-2-isocephem-4-carboxylic acid

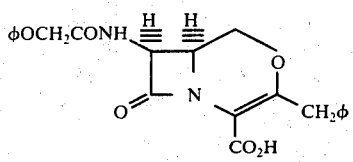

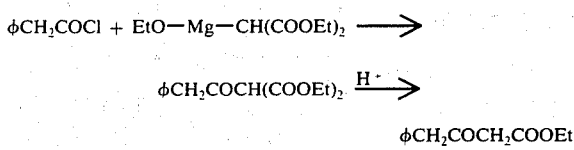

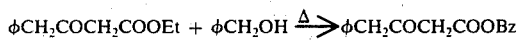

The ethyl γ-phenylacetoacetate was prepared after the procedure described[1] in 40% yield. B.P. 0.005 mm 103°-105°.

1. G. R. Ames and W. Davey. J. Chem. Soc. 1957, 3480-87.

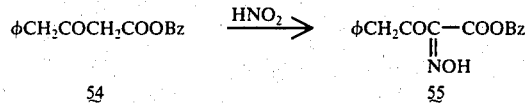

A mixture of ethyl γ-phenylacetoacetate (166 g.; 0.76 mole) and benzyl alcohol (100 g.; 0.92 mole) was immersed into an oil bath, preheated to 170°, and with stirring the ethyl alcohol produced was distilled off. With an aspirator, a forerun fraction (B.P. 100 mm 65°-80°) was removed and finally the residue was distilled at low pressure. B.P. 0.002 mm 155°-157°. By recycling the forerun, a further quantity of pure compound was obtained. Overall yield was 171 g. (84%).

φCH$_2$COCH$_2$COOBz $\xrightarrow{HNO_2}$ φCH$_2$COC—COOBz
$\qquad\qquad\qquad\qquad\qquad\qquad\quad$ ‖
$\qquad\qquad\qquad\qquad\qquad\qquad\quad$ NOH
54 $\qquad\qquad\qquad\qquad\qquad\qquad$ 55

A solution of benzyl γ-phenylacetoacetate 54 (85.5 g.; 0.32 mole) in glacial acetic acid (400 ml.) and water (150 ml.) was cooled to 5° in an ice bath and while stirring vigorously, to it was added dropwise in 4 minutes a solution of sodium nitrite (25.5 g.; 0.37 mole) in water (100 ml.). The reaction temperature rose to 16° C. and was stirred with cooling for 30 minutes more. The cooling bath was removed and stirring continued for 2 hours. 800 ml. of water was added and the solution was extracted with 3 × 100 ml. CH$_2$Cl$_2$. The combined extracts were washed with water and brine, dried over Na$_2$SO$_4$ and evaporated, leaving 92.50 g. oil. This was crystallized in 90 ml. CCl$_4$ to give light yellow crystals 52.80 g. (56%), m.p. 69°-70° C.

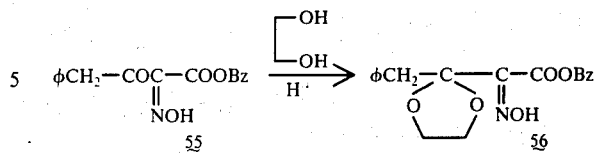

A mixture of oxime 55(5.94 g.; 20 mm), ethylene glycol (1.36 g.; 22 mm) and p-toluenesulfonic acid monohydrate (0.59 g.) in benzene (100 ml.; A.R.) was refluxed over a Dean-Stark water trap for 3½ hours. It was cooled, and poured into 100 ml. saturated NaHCO$_3$ and extracted with benzene. After the organic phase was washed with water, dried over Na$_2$SO$_4$ and evaporated, 6.70 g. of an oil was obtained. It was crystallized in 20 ml., CCl$_4$, and gave 4.0 g. (57%) light yellow solid, m.p. 90°-92° C.

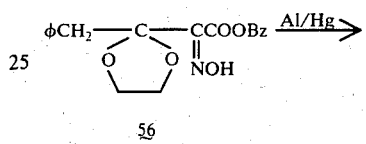

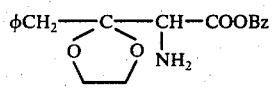

Aluminum foil (6.9 g.; 255 mm) cut into small strips and loosely folded, was covered with 5% NaOH and allowed to react for 2 minutes. It was decanted and washed successively with water and 95% EtOH, then covered with 2% mercuric chloride, and allowed to react for 2 minutes. After decanting, it was washed with water and ether, then covered with "wet ether". To this amalgam with stirring was added an ether solution of the "oximinioester", (29.5 g.; 85 mm) in ether (600 ml.). There was a mildly exothermic reaction and after the addition was complete, it was refluxed for 2 hours. It was cooled, filtered through celite and extracted with 4 × 100 ml. 10% HCl. White crystals separated from the aqueous phase and were filtered, washed with cold water and dried to give 29.0 g. solid, m.p. 181°-183° with decomposition. Recrystallized from EtOH/ether, m.p. 182°-184° with decomposition. The free base was obtained by suspending the hydrochloride in water and alkalizing with cold concentrated NH$_4$OH. Yield 100%.

Anal. Calc'd. for C$_{19}$H$_{22}$NO$_4$·HCl: C, 62.72; H, 6.09; N, 3,85. Found: C, 62.83; H, 6.14; N, 3.84.

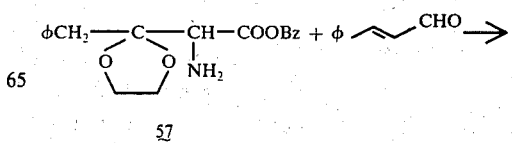

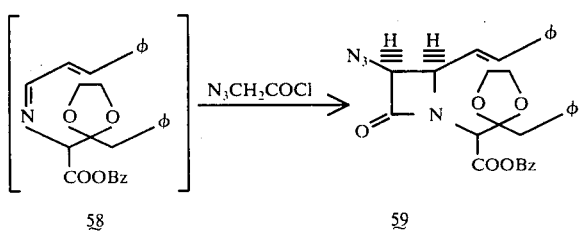

Ketal-amine 57(56.70 g.; 0.173 mole) was dissolved in dry CH$_2$Cl$_2$ (600 ml.) and to it was added cinnamaldehyde (23.0 g.; 0.173 mole). The solution was refluxed for 30 minutes and the solvent was removed on the aspirator. The residue was redissolved in CH$_2$Cl$_2$ (600 ml.), the flask was fitted with a Dean-Stark water trap, and the solvent refluxed while 300 ml. of CH$_2$Cl$_2$ was collected and continuously removed through the trap. The residue was dried over Na$_2$SO$_4$ and evaporated to dryness leaving 77.32 g. light yellow oil. This was redissolved in CH$_2$Cl$_2$ (300 ml.). Triethylamine (27 ml.; 0.19 mole) was added and while stirring and cooling at 3°–5° C. in an ice-bath there was added dropwise a solution of azidoacetyl chloride (22.8 g.; 0.19 mole) in CH$_2$Cl$_2$ (300 ml.), addition being done over 2 hours. It was kept at room temperature under nitrogen for 16 hours, and refluxed for 1 hour. The solution was cooled, washed with 10% HCl, then with brine, dried over Na$_2$SO$_4$ and evaporated to give 90.35 g. It was used as such with no further purification.

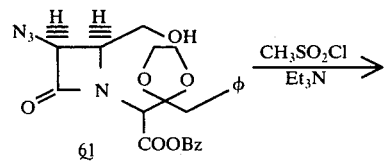

Styryl β-lactam 59 (11.0 g.; 21 mm) was dissolved in CH$_2$Cl$_2$ (150 ml.) and ozonized at −60° until a blue color appeared, then O$_2$ was used to flush away the excess ozone. To the solution was added 7.7 ml. (105 mmole) of dimethyl sulfide and the cooling bath was allowed to warm up to 25 ° C. spontaneously in 5 hours. The solution was kept at 25° for 16 hours then washed with 1% NaHCO$_3$ and brine, dried over Na$_2$SO$_4$ and evaporated to dryness. It was triturated with petroleum ether (30°–60°) and the residue kept at 0.05 mm/Hg and 45° C for 16 hours. This removed all the benzaldehyde, and left 8.07 g. oil. It was used as such without any further purification.

A solution of aldehyde 60 (2.1 g.; 5 mm) in THF (50 ml.; A.R.) was cooled to −5° in an ice-salt bath and while stirring, to it ws added sodium borohydride (0.1 g.; 2.9 mm), all at once. It was stirred at 0°–5° for 30 minutes, then the cooling bath was removed and stirring continued at room temperature for 30 minutes. It was carefully acidified with cold 10% HCl, saturated with sodium chloride and extracted with ether. The ether phase was washed with water, and brine, dried over Na$_2$SO$_4$ and evaporated to give 1.88 g. oil. It was purified by chromatography on silica gel III, eluting with ether/petroleum ether 2:1.

A mixture of alcohol 61 (1.10 g.; 2.6 mm) and triethylamine (0.29 g.; 2.85 mm) in CH$_2$Cl$_2$ (25 ml.) was cooled to 0° C. and with stirring under nitrogen to it was added dropwise a solution of methanesulfonyl chloride (0.33 g.; 2.85 mm) in CH$_2$Cl$_2$ (10 ml.). It was stirred at 0° for 15 minutes, then at room temperature for 1 hour. It was washed with water then with brine, dried over Na$_2$SO$_4$ and evaporated to give 1.36 g. oil. It was used as such with no further purification.

The ketal-mesylate 62(1.36 g.; 2.5 mm) was dissolved in 95% trifluoroacetic acid (15 ml.) and stirred at 50°–55° for 2 hours on an oil bath. It was poured into brine and extracted with CH$_2$Cl$_2$. After washing the organic extracts with water and drying over Na$_2$SO$_4$, the solvent was removed on the aspirator and left 1.20 g. red oil. No further purification was attempted.

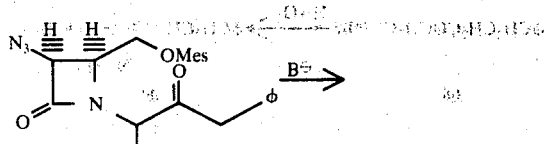

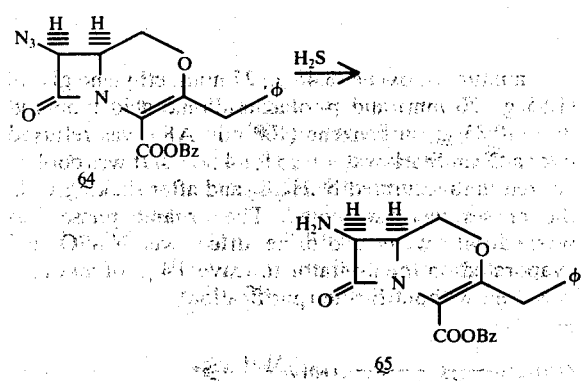

A mixture of curde enol-mesylate 63 (5.4 g.) and triethylamine (2 ml.) in dry CH$_2$Cl$_2$ (100 ml.) was refluxed for 5 hours. It was cooled, washed with 10% HCl and water, dried over Na$_2$SO$_4$ and evaporated on the aspirator to give 4.24 g. oil. This was purified by chromatography on 200 g. of silica gel III, eluting with ether/petroleum ether 2:1. The pure compound 64 crystallized, m.p. 117°–118°.

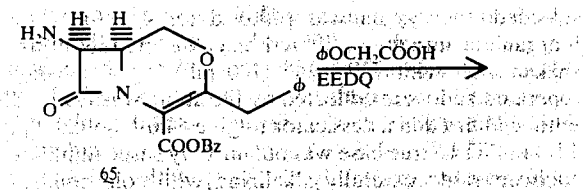

A mixture of "azido-isocephem" 64 (0.49 g.; 1.25mm) and triethylamine (0.9 ml.; 6.5 mm) in CH$_2$Cl$_2$ (50 ml.) was cooled in an ice bath and while being stirred, was saturated with H$_2$S. The cooling bath was removed and there was gas evolution which subsided in 10 minutes. At this point, T.L.C. showed no starting material remained. Attempts to extract the amine from the solution as its hydrochloride failed as it is more soluble in CH$_2$Cl$_2$ than in water. The CH$_2$Cl$_2$ solution of the free base was dried over Na$_2$SO$_4$ and evaporated on the aspirator to leave 0.40 g. of a semi-solid. It was used as such with no further purification.

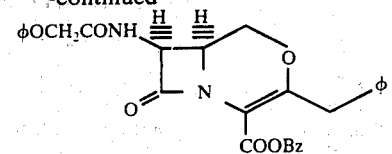

A solution of "amine-isocephem" 65 (0.48 g.; 1.25 mm), phenoxyacetic acid (0.19; 1.25 mm) and EEDQ (0.31 g.; 1.25 mm) in CH$_2$Cl$_2$ (100 ml.) was stirred at room temperature for 16 hours. It was washed with 1% NaHCO$_3$ solution, then with brine, dried over Na$_2$SO$_4$ and evaporated on the aspirator to leave 0.56 g. of a slightly yellow gum. It was used with no further purification.

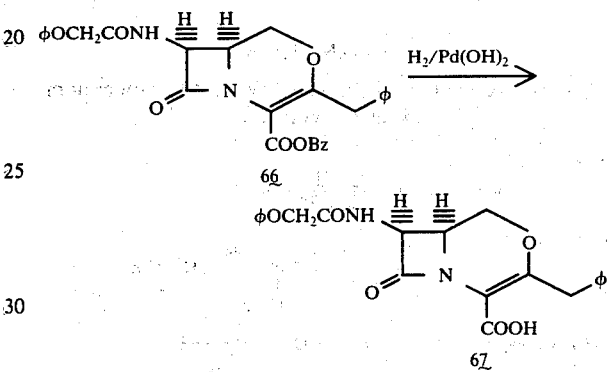

The "isocephem compound" 66 (0.49 g.; 1 mm) was dissolved in ethyl acetate (100 ml.) and glacial acetic acid (10 ml.), 20% Pd(OH)$_2$ on carbon (0.50 g.) was added and the mixture was agitated on a Paar apparatus at 60 psi of H$_2$ for 2 hours. The solid was filtered off on celite and the filtrate evaporated to dryness. The residue was extracted with saturated NaHCO$_3$, the aqueous phase was acidified with 10% HCl and extracted with CH$_2$Cl$_2$. This was then washed with water, dried over Na$_2$SO$_4$ and evaporated to dryness. The resulting solid was recrystallized from benzene and gave white crystals, m.p. 123°–125° with decomposition.

Anal. Calc'd. for C$_{22}$H$_{20}$N$_2$O$_6$: C, 64.70; H, 4.94; N, 6.86. Found: C, 64.78; H, 4.87; N, 6.80.

A sample of compound 67 prepared above which can be named 7β-phenoxyacetamido-3-benzyl-Δ$^3$-O-2-isocephem-4-carboxylic acid (also called BC-L17) after solution in water and dilution with Nutrient Broth was found to exhibit the following Minimum Inhibitory Concentrations (M.I.C.) in mcg./ml. versus the indicated microorganisms as determined by overnight incubation at 37° C. by tube dilution. Cephalexin was included as a comparison compound.

Table 3

| Organism | | M.I.C. in mcg./ml. | |
|---|---|---|---|
| | | BC-L17 | Cephalexin |
| D. pneumoniae +5% serum* | A9585 | .25 | .16 |
| Str. pyogenes +5% serum* | A9604 | .25 | .16 |
| S. aureus Smith | A9537 | .25 | .6 |
| S. aureus Smith +50% serum | A9537 | 1 | 1.3 |
| S. aureus BX1633-2 at 10$^{-3}$ dil'n | A9606 | 8 | 1 |
| S. aureus BX1633-2 | A9606 | >125 | 2 |

Table 3-continued

| Organism | | M.I.C. in mcg./ml. BC-L17 | Cephalexin |
|---|---|---|---|
| at 10$^{-2}$ dil'n | | | |
| S. aureus meth.-resist; at 10$^{-3}$ dil'n | A15097 | 125 | 16 |
| Sal. enteritidis [*][*] | A9531 | 32 | 2 |
| E. coli Juhl [*][*] | A15119 | >125 | 8 |
| E. coli [*][+] | A9675 | >125 | 16 |
| K. pneumoniae[+][+] | A9977 | >125 | 4 |
| K. pneumoniae[+][+] | A15130 | >125 | 16 |
| Pr. mirabilis[+][*] | A9900 | >125 | 4 |
| Pr. morganii[+][+] | A15153 | >125 | >125 |
| Ps. aeruginosa[+][+] | A9843A | >125 | >125 |
| Ser. marcescens[+][+] | A20019 | >125 | >125 |
| Ent. cloacae | A9656 | >125 | >125 |
| Ent. cloacae | A9657 | >125 | 4 |
| Ent. cloacae | A9659 | >125 | >125 |

*50% Nutrient Broth - 45% Antibiotic Assay Broth
**at 10$^{-4}$ dilution.

EXAMPLE 6

7β-Phenoxyacetamido-3-phenethyl-Δ$^3$-O-2-isocephem-4-carboxylic acid

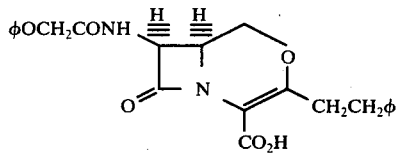

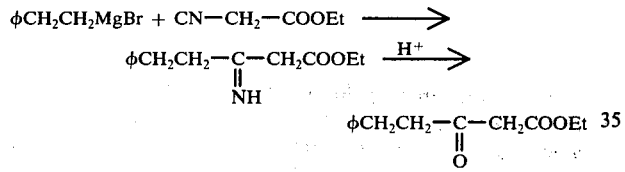

Phenylmagnesium bromide was prepared[1] in the usual way from magnesium (24.30 g.; 1 mole), phenethylbromide (204 g.; 1.1 mole) and a trace of iodine in ether (250 ml.; AR). While maintaining the reaction temperature at 25°-30° C., to it was added ethylcyanoacetate (45.2 g.; 0.25 mole) and the resulting solution was stirred at room temperature for 24 hours. It was decomposed with saturated ammonium chloride, 10% HCl and water and the phases separated. The organic extract was treated with 10% HCl (250 ml.) and stirred vigorously for 3 hours. The organic phase was washed with brine, dried over Na$_2$SO$_4$ and evaporated on the aspirator to give 83.5 g. oil. Fractional distillation gave 12.67 g. (21%) pure product. B.P. 0.1 millimeter 114°-122° C.

1. G. W. Anderson et al, J.A.C.S. 67, 2197-2200 (1945).

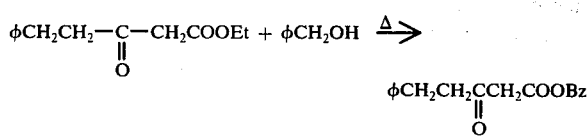

A mixture of ethyl γ-benzylacetoacetate (12.56 g.; 50 mm) and benzyl alcohol (8.1 g.; 75 mm) was immersed into an oil bath preheated to 170° C. and stirred. After ethanol had been distilled off, the excess benzyl alcohol was removed on the aspirator and finally the residue was distilled. B.P. 0.01 millimeter, 160°-163°. 6.15 g. pure product was obtained.

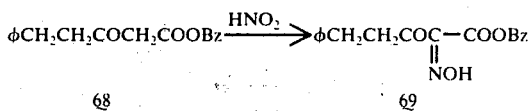

To a solution of benzyl γ-benzylacetoacetate (37.0 g.; 0.13 mole) in glacial acetic acid (50 ml.) was added dropwise in 1 hour a solution of sodium nitrite (10 g.; 0.143 mole) in water (50 ml.). The reaction temperature was kept at 24°-30° C. It was stirred an additional hour after the addition then diluted with water (100 ml.), and extracted with ether. The organic extract was washed with water and with 1% NaHCO$_3$ until the washings were basic, then with brine. It was then dried over Na$_2$SO$_4$ and evaporated on the aspirator to leave 40.1 g. of a light yellow oil. It was used as such with no further purification.

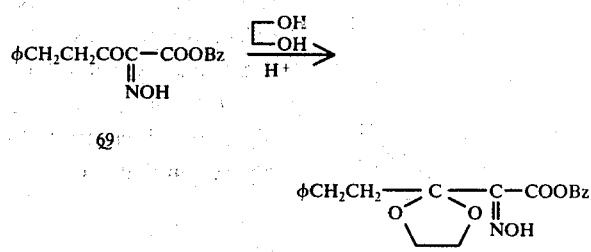

A mixture of oxime (8.48 g.; 27 mm), ethylene glycol (1.85 g.; 30 mm) and p-toluenesulfonic acid monohydrate (0.85 g.) in benzene (100 ml.; AR) was refluxed over a Dean-Stark water trap for 4 hours. It was cooled, poured onto saturated NaHCO$_3$ and after shaking well, the phases were separated. The organic phase was washed with water and brine, dried over Na$_2$SO$_4$ and evaporated on the aspirator to leave 9.4 g. of an oil. It was used without further purification.

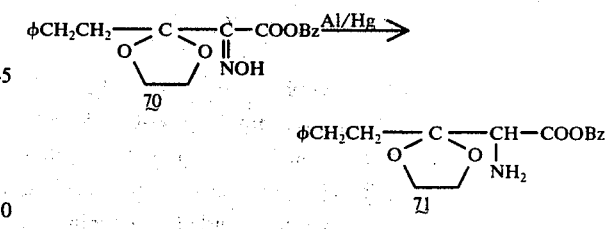

Aluminum foil (27 g.; 1 mole) cut into small strips and loosely folded was covered with 5% NaOH and allowed to react for 2-3 minutes. It was decanted and washed successively with water and .95% EtOH, then covered with 2% mercuric chloride and allowed to react for 2 minutes. After decanting, it was washed with water and ether, and finally covered with "wet ether". To this amalgam with stirring was added an ether solution of the "oximinoester" 70 (43 g.; 0.12 mole) in ether (300 ml.). There was an exothermic reaction and after it subsided, the system was refluxed for 4 hours. The inorganic material was filtered on celite and the filtrate shaken well with 10% HCl (100 ml.) White crystals separated and were collected by filtration, washed with ether and dried in a dessicator to give 54.0 g. solid, m.p. 186-188°. The free base was obtained by suspending the solid in water, carefully alkalizing with cold concentrated NH₄OH and extracting with CH₂Cl₂. After evaporation of the solvent, 27.91 g. of a yellow oil was obtained.

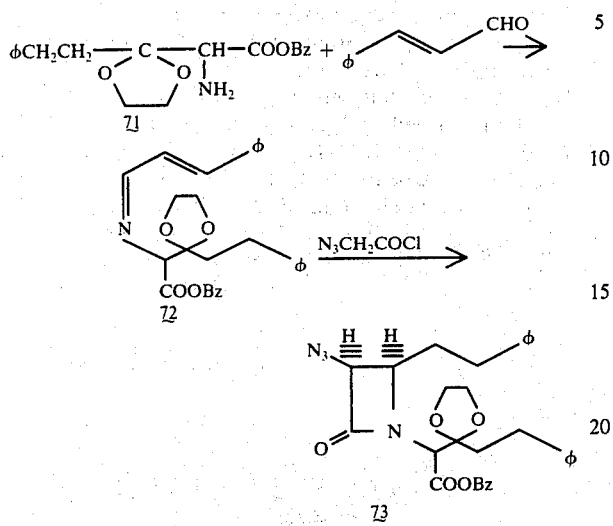

A mixture of "amine-ketal" 71 (27.6 g.; 81 mm) and cinnamaldehyde (10.7 g.; 81 mm) in CH₂Cl₂ (500 ml.) was refluxed over a Dean-Stark water trap while 200 ml. solvent was removed. By replacing the solvent removed with fresh one, a further 3 × 250 ml. fractions were removed also. Finally, the residue was evaporated to dryness on the aspirator and pumped down at 0.05 millimeter/Hg. and 40° C. for 10 minutes. The residue was re-dissolved in CH₂Cl₂ (250 ml.), triethylamine (11.9 ml.; 85 mm) was added and while stirring and cooling in an ice bath, to it was added dropwise in 2½ hours a solution of azidoacetyl chloride (10.15 g.; 85 mm) in CH₂Cl₂ (100 ml.). It was kept at room temperature under nitrogen for 16 hours and refluxed for 1 hour. The solution was cooled, washed with 10% HCl, then with brine, dried over Na₂SO₄ and evaporated on the aspirator to give 44.77 g. red oil. It was used as such with no further purification.

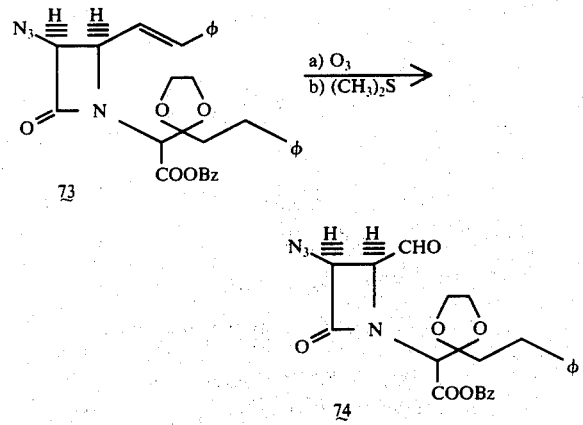

Styryl β-lactam 73(6.7 g.; 12.5 mm) was dissolved in Ch₂Cl₂ (150 ml.), and ozonized at −78° until a blue color appeared, and then nitrogen was used to flush away the excess ozone. To the solution was added dimethyl sulfide (4.5 ml.; 65 mm) and the cooling bath was allowed to warm up to 25° spontaneously. The solution was kept at room temperature for 16 hours then washed with 1% NaHCO₃ and brine, dried over Na₂-SO₄ and evaporated to dryness. It was then pumped down at 0.05 millimeter/Hg. and 50° C. for 20 hours to remove most of the benzaldehyde. The residue was chromatographed on 250 g. of silica gel III, eluting with; first ether/petroleum ether 2:1 (to remove benzaldehyde) and then with ether.

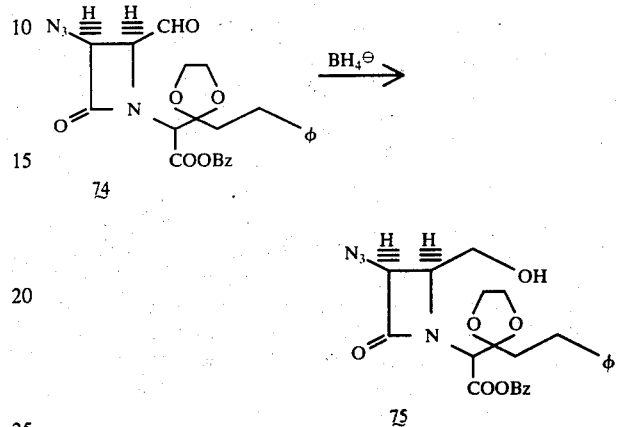

A solution of aldehyde 74(4.1 g.; 8.8 mm) in THF (100 ml.; A.R.) was cooled to −5° and while stirring, to it was added sodium borohydride (0.17 g.; 4.5 mm) all at once.

It was stirred at 315° C. for 1½ hours, then carefully acidified with 10% HCl, saturated with sodium chloride and extracted with ether. The ether phase was washed with water, and brine, dried over Na₂SO₄ and evaporated to give 3.8 g. oil. It was used with no further purification.

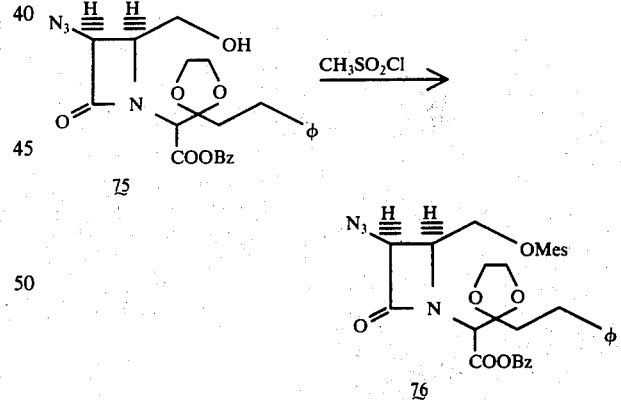

A mixture of alcohol 75 (3.8 g.; 8.3 mm) and triethylamine (1.25 ml.; 9 mm) in CH₂Cl₂(50 ml.) was cooled to 0°, and with stirring under nitrogen, to it was added dropwise, a solution of methanesulfonyl chloride (1.0 g.; 9 mm) in CH₂Cl₂ (25 ml.). It was stirred at room temperature for 1½ hours, then washed with 10% HCl water and brine, and dried over Na₂SO₄. It was then evaporated to give 4.3 g. oil. This was purified by chromatography on 250 g. silica gel III eluting with ether/petroleum ether 3:1. 2.05 g. of pure mesylate was obtained.

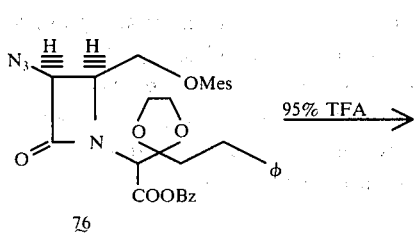

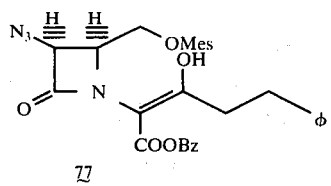

Ketal-mesylate 76 (2.05 g.; 3.7 mm) was dissolved in 95% trifluoroacetic acid (200 ml.) and stirred at 50°-55° C. for 2 hours on an oil bath. It was then poured into a mixture of crushed ice and brine and extracted with $CH_2Cl_2$. After washing the organic extracts with water, and drying over $Na_2SO_4$, the solvent was removed on the aspirator and left 1.73 g. oil. No further purification was attempted.

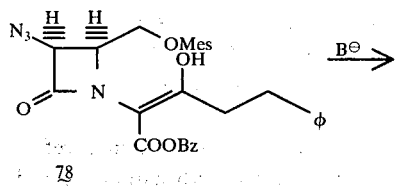

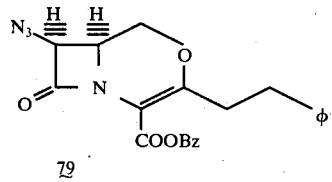

A mixture of crude "enol-mesylate" 78 (1.71 g.; 3.4 mm) and triethylamine (0.48 ml.; 3.4 mm) in $CH_2Cl_2$ (50 ml.) was refluxed for 5 hours. It was cooled, washed with 10% HCl and water, dried over $Na_2SO_4$ and evaporated on the aspirator to give 1.35 g. oil. This was purified by chromotography on 75 g. silica gel III eluting with ether/petroleum ether 2:1. The pure cis-β-lactam was obtained as white crystals, m.p. 97°-98° (MeOH).

Anal. Calc'd. for $C_{22}H_{20}N_4O_4$: C, 65.34; H, 4.98; N, 13.85. Found: C, 65.36; H, 4.96; N, 13.97.

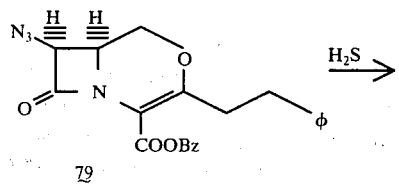

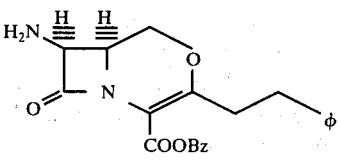

A mixture of "azido isocephem" 80, (0.81 g.; 2 mm) and triethylamine (0.56 ml.; 4 mm) in $CH_2Cl_2$ (50 ml.) was cooled in an ice bath and while being stirred, was saturated with $H_2S$. The cooling bath was removed and there was gas evolution. After stirring at room temperature for 1 hour, the solution was evaporated at room temperature and partitioned between ether and 10% HCl. White crystals separated and were collected by filtration, washed with ether and dried to give 1.12 g. white solid, m.p. 120°-123° with decomposition. The free base was obtained by suspending the solid in water, alkalizing with cold concentrated $NH_4OH$ and extracting with $CH_2Cl_2$. This was washed with brine, dried over $Na_2SO_4$ and evaporated on the aspirator.

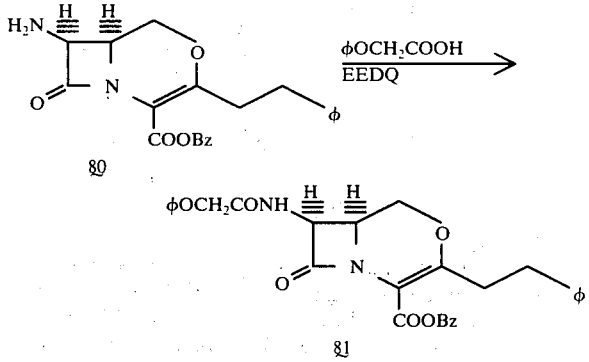

A solution of "amino isocephem" 80 (0.49 g.; 1.05 mmole), phenoxyacetic acid (0.16 g.; 1.05 mm) and EEDQ (0.26 g.; 1.05 mm) in $CH_2Cl_2$ (50 ml.) was stirred at room temperature for 2 hours. It washed with 1% $NaHCO_3$ solution, then with brine, dried over $Na_2SO_4$ and evaporated on the aspirator to leave 0.49 g. white solid, m.p. 146°-148° C. It was used with no further purification.

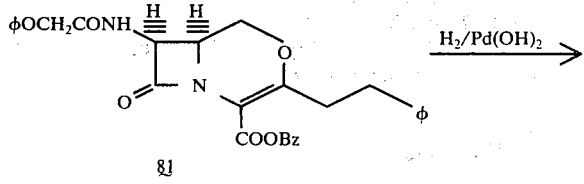

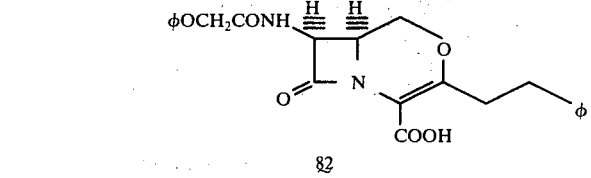

A solution of isocephem compound 81 (0.49 g.; 0.9 mm) in ethyl acetate (75 ml.) was added to a prehydrogenated sample of 20% $Pd(OH)_2$ on carbon (0.50 g.) in ethyl acetate (25 ml.). It was then stirred under hydrogen at atmospheric pressure and after 15 minutes, gas consumption had ceased. It was filtered through a celite pad, washed well with ethyl acetate, and the solvent was removed on the aspirator to leave 0.40 g. of an amorphous solid. This was suspended in ether and extracted with 2% $NaHCO_3$. The aqueous extract was acidified with 10% HCl and the white solid collected by suction filtration, washed with water and dried to give a white solid, m.p. 160°-162° with decomposition. Recrystallized from CHCl₃/ether, m.p. 162°-163° with decomposition.

Anal. Calc'd for $C_{23}H_{22}N_2O_6$: C, 65.39; H, 5.25; N, 6.63. Found: C, 65.28; H, 5.36; N, 6.56.

A sample of compound 82 prepared above which can be named 7β-phenoxyacetamido-3-phenethyl-Δ³-O-2-isocephem-4-carboxylic acid (also called BC-L54) after solution in water and dilution with Nutrient Broth was found to exhibit the following Minimum Inhibitory Concentrations (M.I.C.) in mcg./ml. versus the indicated microorganisms as determined by overnight incubation at 37° C. by tube dilution. Cephalexin was included as a comparison compound.

Table 4

M.I.C. in mcg./ml.

| Organism | | BC-L54 | Cephalexin |
|---|---|---|---|
| D. pneumoniae +5% serum* | A9585 | .03 | .13 |
| Str. pyogenes +5% serum* | A9604 | .03 | .13 |
| S. aureus Smith | A9537 | .06 | .25 |
| S. aureus Smith +50% serum | A9537 | 4 | .5 |
| S. aureus BX1633-2 at 10⁻³ dil'n | A9606 | 8 | 1 |
| S. aureus BX1633-2 at 10⁻² dil'n | A9606 | >125 | 4 |
| S. aureus meth.-resist; at 10⁻³ dil'n | A15097 | 125 | 32 |
| Sal. enteritidis | A9531 | >125 | 2 |
| E. coli Juhl | A15119 | .5 | 4 |
| E. coli | A9675 | >125 | 8 |
| K. pneumoniae | A9977 | >125 | 2 |
| K. pneumoniae | A15130 | >125 | 8 |
| Pr. mirabilis | A9900 | >125 | 4 |
| Pr. morganii | A15153 | >125 | >125 |
| Ps. aeruginosa | A9843A | >125 | >125 |
| Ser. marcescens | A20019 | >125 | >125 |
| Ent. cloacae | A9656 | >125 | >125 |
| Ent. cloacae | A9657 | >125 | 2 |
| Ent. cloacae | A9659 | >125 | >125 |

*50% Nutrient Broth - 45% Antibiotic Assay Broth
at 10⁻⁴ dilution.

EXAMPLE 7

Potassium 7β-Phenoxyacetamido-Δ³-O-2-isocephem-4-carboxylate

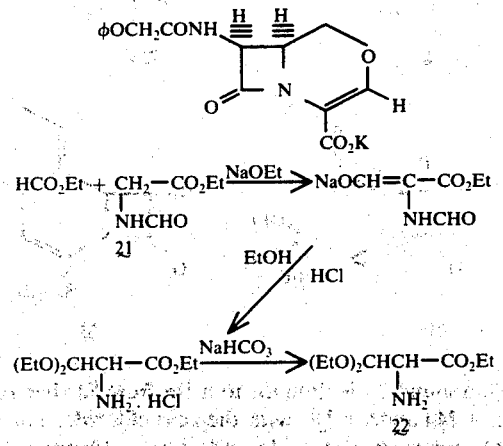

Procedure: A mixture of ethyl N-formyl glycinate (21) (454 g., 3.46 moles) and ethyl formate (1800 ml.) was slowly added into a suspension of freshly prepared sodium ethoxide (3.46 moles, dried in high vacuum at 150° C. for 24 hrs. the sodium ethoxide must be completely free of ethanol as yields are considerably lowered otherwise) in 2620 ml. of dry benzene with stirring in an ice bath for three hours. The suspension was allowed to stand at 4° C. for 18 hours. The solution was carefully decanted and the solid residue washed several times with benzene. To the solid was added slowly 4500 ml. of 15% HCl-absolute ethanol.

The solution was stirred at 25° C. for 18 hours. The ethanol was removed by distillation at reduced pressure. The residue was dissolved in 4.8 liters methanol, then 750 g. of sodium bicarbonate was added at 25° C. The suspension was stirred 18 hours, filtered and the filtrate evaporated. The residue was taken up in 4 liters of ether, dried over anhydrous sodium sulfate and evaporated. The oily residue was distilled to give 170 g. (28%) β,β-diethoxyethylalanate (22), b.p. 90°-94° C. (0.1 - 0.13 mm). (Literature b.p. 71°/1 mm; Ellis V. Brown, Chemistry of Penicillin (H. T. Clarke et al.) Princeton Univ. Press, 1949, p. 473-534.)

The NMR and IR spectra of 22 were consistent with the assigned structure.

β,β-diethoxyethylalanate was also prepared by the following procedure:

To a suspension of 49.5 g. (0.65 moles) of sodium ethoxide (Note 1) in 300 ml. benzene was added a solution of 65.5 g. (0.05 moles) N-formyl ethyl glycinate in 300 ml. ethylformate in a 3 L. flask equipped with a mechanical stirrer at 0° C. over 30 minutes. After stirring for 1 hour, the solution clarified and was allowed to stand 18 hours at 4° C. A solid separated from the solution. The supernatant liquid was decanted and the residue washed with 300 ml. benzene.

To the solid was added 150 ml. ethanol and 550 ml. $CH_2Cl_2$ and the suspension was cooled to 0-5° C. in an ice bath. To the solution a stream of dry HCl gas was added for 1 hour. The cooling was removed and the HCl gas bubbled in an additional 5.5 hours after which the solution was allowed to stand at 25° C. for 18 hours. The excess HCl was purged by passing a stream of nitrogen through the solution for 30 minutes and the solution cooled to −10° C. in a methanol-ice bath. A stream of ammonia was passed through the solution until the pH = 9.0. The solution was diluted with 500 ml. $CH_2Cl_2$ and the solid ammonium chloride removed by filtration. The filter cake was washed with an additional 500 ml. $CH_2Cl_2$. The filtrate was evaporated to dryness at reduced pressure (bath temperature <45° C.). The residual oil was extracted with ether (2 × 500 ml.) and the extracts evaporated to dryness. The residual oil was extracted into petroleum ether (20°-60° C.) (3 × 300 ml.). The extracts were dried over $Na_2SO_4$, filtered and evaporated to yield 54.6 g. (~54%). The NMR and IR spectra of this oil were identical in all respects to those of authentic 22. This oil could be used as such in subsequent steps. Distillation gave 43.7 g. (42.5%) of pure 22 b.p. 60°-75° C. (0.005 millimeter/Hg.).

Note 1. Commercial NaOEt was used. The 30% excess was necessary.

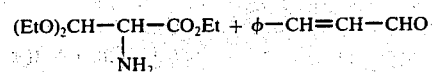

22

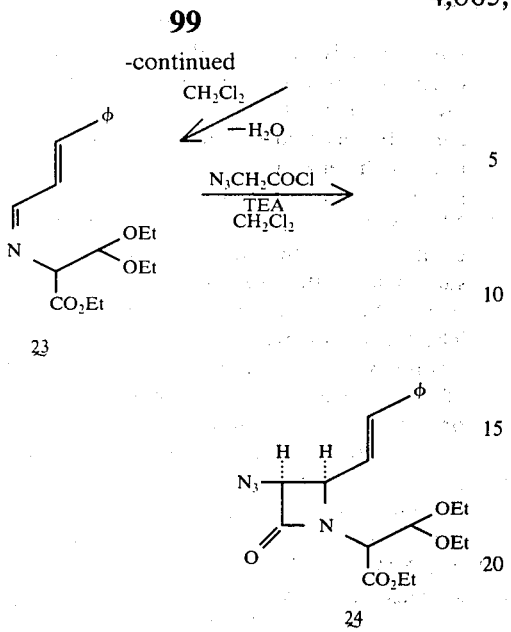

Procedure:

A. Preparation of Schiff Base (23). A mixture of 95.2 g. (0.46 mole) β,β-diethoxyalanine ethyl ester and 60.8 g. (0.46 mole) cinnamaldehyde in 1.5 L. of methylene chloride was boiled at reflux for 30 minutes. After this initial reflux period 850 ml. of methylene chloride were distilled at atmospheric pressure over 1.5 hours. (azeotrope with water). The concentrated solution was dried over anhydrous sodium sulfate (large excess >100 g.) for 1 hour. The drying agent was removed by filtration and the solution of 23 evaporated to dryness at reduced pressure and the residue pumped at <1 millimeter/Hg. pressure for 30 minutes at 40° C. The residue was then diluted to 1.3 liters with dry methylene chloride.

The formation of the Schiff base may be accomplished in a number of ways. On a small scale the two reactants may be mixed in a suitble solvent (benzene, ether, $CH_2Cl_2$, etc.) in the presence of a drying agent ($Na_2SO_4$, $MgSO_4$). Alternatively the water may be removed azeotropically with benzene. Inasmuch as the subsequent reaction is done in methylene chloride the above method is preferred. The $CH_2Cl_2$ is dried by passing thru an alumina (Act I) column which removed any alcohol which may be present as preservative. At the end of the reaction a small aliquot was evaporated and the NMR and IR spectra taken to check for completeness; the yield is quantitative.

B. Preparation of azidoacetyl chloride. The azidoacetyl chloride was prepared via a modification of the method of J. H. Boyer and J. Horner, J. Am. Chem. Soc., 77, 951 (1955).

To 128 g. (1.354 mole) chloroacetic acid in 300 ml. of water was added 7 ml. 50% sodium hydroxide solution (0.0875 mole) and 110 g. (1.69 moles) of sodium azide. The slurry was contained in a three-necked 2 liter round-bottomed flask fitted with two efficient condensers and an addition funnel. [THE REACTION MUST BE DONE IN AN EFFICIENT FUME HOOD! The original literature preparation used at least one equivalent of sodium hydroxide whereas we used less than 10 mole %.] The mixture was layered with 100 ml. ether and heated on a steambath for 24 hours. The orange solution (occasionally colorless) was cooled to 0°-5° C. in an ice bath. To the cooled solution was added 300 ml. of 10% $H_2SO_4$ followed by solid sodium chloride to saturation. The solution was extracted with ether (5 × 200 ml.), the extracts dried over sodium sulfate. The drying agent filtered, and the ether evaporated below 30° C. at reduced pressure. The NMR spectrum of the residual oil indicated it to be a ½ hydrate of azidoacetic acid contaminated with 10% ether. The oil was used without further purification.

To the oil cooled in an ice bath was added 340 g. (2.85 moles) thionyl chloride (the addition of the first 50 ml. is slow as vigorous gas evolution occurs, the remainder is added quickly). After addition, the solution was refluxed 2 hours. The excess thionyl chloride was distilled at reduced pressure (<50° C., 70 mm). The residue was distilled to yield 93 g. (57.2%) azidoacetyl chloride, b.p. 38°-40° C/12-15 mm Hg. The distillation must be carried out using a water bath the temperature of which must never exceed 80° C. An explosion occurred in one run where higher bath temperatures were utilized. The NMR and IR spectra are consistent with the assigned structure.

C. β-lactam formation. The freshly prepared Schiff base solution (0.46 moles in 1.3 l. methylene chloride) was cooled to 0°-5° C. with ice bath. To this 46.1 g. (0.46 mole) triethylamine was added. A solution of 56.0 g. (0.46 moles) azidoacetyl chloride in 500 ml. methylene chloride was added dropwise over 1 hour. The solution was stirred an additional 30 min., washed with water, saturated NaCl solution, and dried over $Na_2SO_4$. Evaporation of this solution yielded 187.0 g. (>98% crude yield) of compound 24 as a reddish oil.

The compound 24 was obtained as a mixture of diastereoisomers (24a and 24b). Occasionally a by-product was also obtained when excesses of azido acetyl chloride were used. This by-product has been identified as 25.

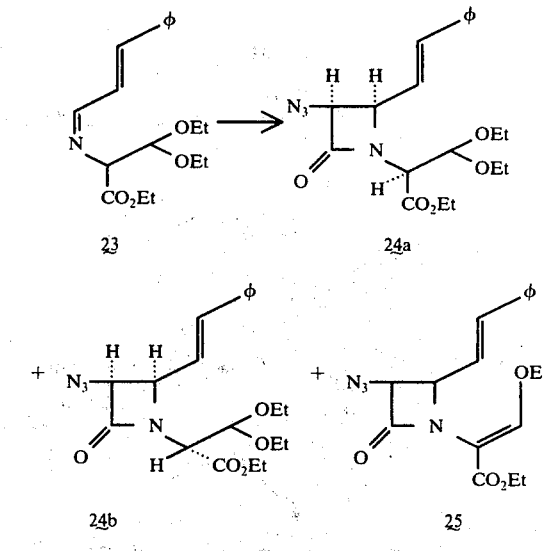

Compound 25 is thought to arise from further reaction of 24a and/or 24b with the acid chloride. The stereochemistry of the azido and styrryl substituents of 24a, 24b and 25 has been shown to be exclusively cis; no trace of trans component could be detected by NMR. The mixture of compounds 24a and 24b was readily separated from 25 by column chromatography (Dry-column technique on silica gel (15% $H_2O$) using ether as eluent).

Purification of compounds 24a and 24b by chromatography was not satisfactory as losses occurred. Only partial separation could be achieved. When the cycloaddition was carried out as described formation of 25 was minimal (<2 - 5%).

Compound 25 was shown to be a single geometrical isomer as indicated in the diagram above.

Generally the compound 24 was used as such in subsequent reactions.

A small sample of the crude β-lactam 24 was chromatographed on silica gel (deactivated - 15% water) by dry column technique using methylene chloride as eluent. Two pure fractions (as determined by TLC and NMR) were obtained corresponding to compounds 24 and 25. The oils were analyzed. Compound 24 (mixture of diastereoisomers) MW = 402.460

Anal. Calc'd for $C_{20}H_{26}N_4O_5$. 0.1 $CH_2Cl_2$: C, 58.50; H, 6.35; N, 13.64. Found: C, 58.48; H, 6.48; N, 13.38.
Compound 25
MW = 356 390

Anal. Calc'd For $C_{18}H_{20}N_4O_4$: C, 60.66; H, 5.66; N, 15.72. Found: C, 60.78; H, 5.73; N 15.91.

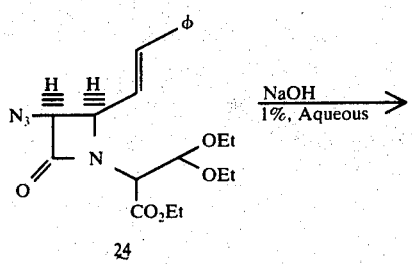

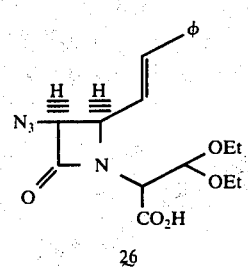

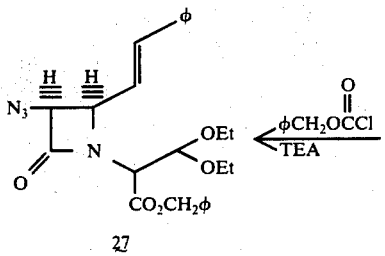

Procedure:

A. In a 3 liter round bottomed flask equipped with a magnetic stirrer was dissolved 119 g. (0.296 moles) of compound 24 in 1 liter of ethanol. To this was added 100 ml. of water followed by 1230 ml. of 1% aqueous sodium hydroxide over a period of 1.5 hours. The solution was maintained at 20° - 25° C. After addition, the solution was stirred 1 hour. To the solution was added 10% HCl to pH 3 followed by 500 ml. saturated NaCl solution. The aqueous phase was extracted by three portions of CHCl₃ (600, 300, 300 ml.) and the organic layer evaporated. The residue was re-dissolved in 500 ml. ether and extracted with three portions (600, 300, 300 ml.) of saturated sodium bicarbonate solution. The aqueous layer was acidified to pH 3 with 10% HCl and extracted into CHCl₃ (in three portions, 600, 300 and 300 ml.). The organic layer was dried over MgSO₄, filtered, and evaporated to yield 97 g. (88% yield) of crude acid 26. The IR and NMR spectra of the acid were consistent with the assigned structure.

B. The acid 26 (192 g.) was dissolved in 1 l. dry CH₂Cl₂ with 53.5 g. (73 ml.) of triethylamine and cooled to 0° - 5° C. in an ice bath. To this was added benzyl chloroformate (96 g.) dropwise over a two hour period with stirring. Following the addition the solution was stirred at room temperature for 30 min. The solution was washed with water (2 × 200 ml.) until neutral, with brine solution (100 ml.) and then dried over MgSO₄. Evaporation afforded 27 as a dark brown oil. The oil was passed through a column of granular adsorbant magnesium silicate (Florisil; 400 g.) with methylene chloride to give 204 g. (85% crude yield) of the desired ester 27. NMR and IR spectra were compatible with the assigned structure.

Generally the oil was not purified further but was used as such in subsequent reactions.

The reaction proceeds according to the following scheme.

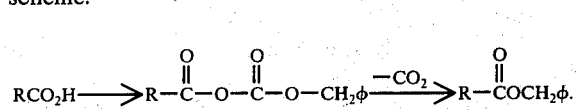

The IR spectrum of the crude reaction mixture indicates no mixed anhydride to be present.

The crude product contained the mixture of desired diastereoisomeric esters, benzyl alcohol, and a small amount of acid. The column chromatography removed much of the acid and other impurities. The benzyl esters are generally not very stable to column chromatography so purification is usually carried out at a later step in the sequence.

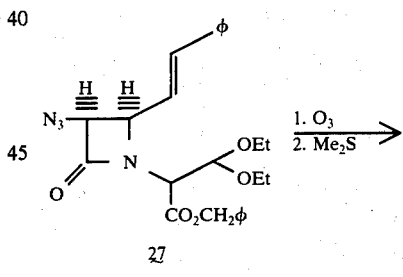

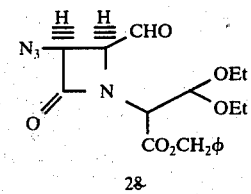

Procedure:

A solution of 4.8 g. (10.04 mmoles) compound 27 in 80 ml. dry methylene chloride was prepared and cooled to −78° C. in an acetone-dry ice bath. To this was added ozone until a blue color persisted. The ozone addition was ended and the excess ozone removed by bubbling dry nitrogen through the solution. To the solution was added 5 ml. of dimethyl sulfide.

The purpose of the dimethyl sulfide is to decompose the initially formed ozonide.

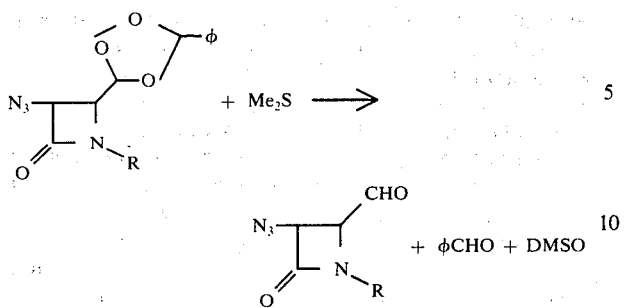

the DMSO thus produced can also react with the ozonide as shown below

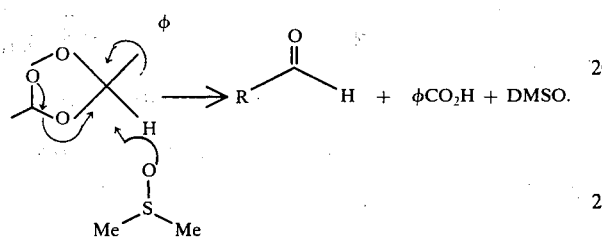

The washing with the NaHCO₃ removes the benzoic acid thus produced.

The solution was allowed to come to room temperature over 1 hour. The solution was then washed with water (20 ml.), saturated NaHCO₃ (20 ml.), water (10 ml.), brine, and dried over MgSO₄. The solution was filtered and evaporated to give 5.0 g. of an oil. The by-product benzaldehyde was removed by distillation at 0.05 mm. Hg. and a bath temperature of ~65° C. The residual oil 4.0 g. (95%) was analyzed by NMR which indicates 77% free aldehyde 28.

The desired aldehyde forms a hydrate which tends to lower the amount of free aldehyde observable in the NMR spectrum.

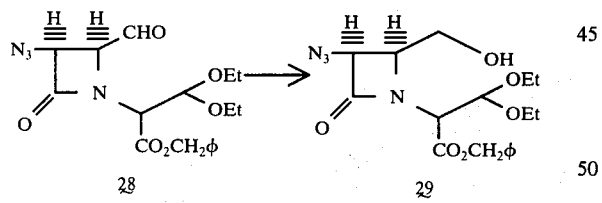

procedure:

To 3.5 g. (9.0 mmoles) of compound 28 in 30 ml. 95% ethanol at 0°–5° C. was added 255 mg. (6.0 mmoles) of sodium borohydride with stirring. After 30 min. at 0°–5° C. the solution was stirred an additional 30 min. at 25° C. The solution was acidified to about pH 4 with 10% hydrochloric acid and diluted with 40 ml. ice water. The aqueous layer was extracted with chloroform (3 × 30 ml.). The combined extracts were washed with water (2 × 10 ml.), brine, dried over MgSO₄, filtered and evaporated to yield 3.4 g. crude alcohol 29. The oil was chromatographed on silica gel (5% water) with chloroform to yield 3.0 g. pure alcohol 29 (85%). The Ir and NMR spectra were compatible with the assigned structure.

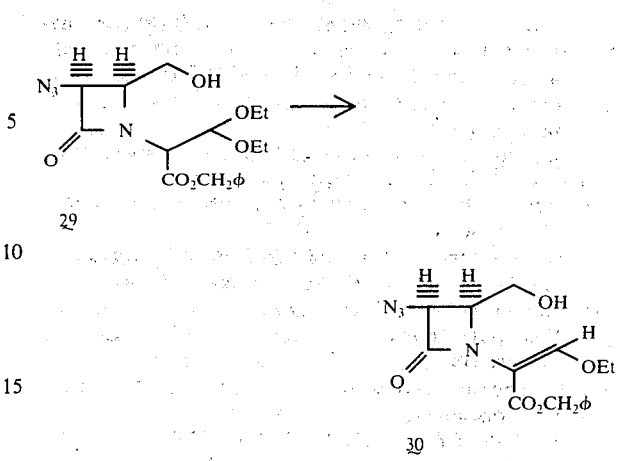

Procedure:

A mixture of 3.2 g. (8.17 mmoles) compound 29, 11 ml. acetic anhydride, and 1.12 g. (8.2 mmoles) zinc chloride was stirred 18 hours at 25° C. The reaction mixture was evaporated at reduced pressure and the residue taken up in 50 ml. — methylene chloride — 20 ml. water. The organic phase was separated, washed with water, brine, dried over MgSO₄, filtered and the filtrate evaporated to yield 3.0 g. of an oil. The oil was chromatographed on 50 g. silica gel (deactivated — 5% water) by dry column technique using chloroform as an eluent. Evaporation of the eluent gave 1.3 g. (41%) of pure 30 as an oil. The IR and NMR spectra were compatible with the assigned structure.

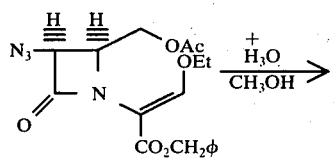

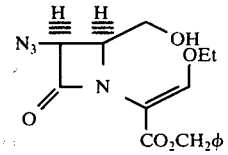

Procedure:

Compound 30, 5.95 g. (15.35 mmoles) was refluxed in 35 ml. CH₃OH and 35 ml. 10% hydrochloric acid for a period of 1 hour. The solvent was partially evaporated at reduced pressure and the aqueous residue was extracted with chloroform (3 × 30 ml.). The combined extracts were washed with water (2 × 10 ml.), saturated brine, and dried over anhydrous magnesium sulfate. The solution was filtered and evaporated to give 4.6 g. (87% yield) of 31 as an oil. The NMR and IR spectra of this oil were consistent with the assigned structure.

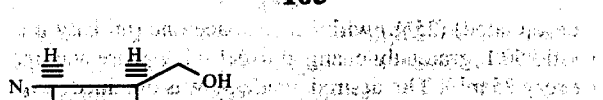

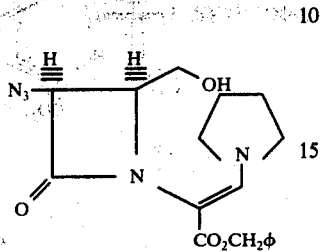

Procedure:

A solution of 4.6 g. (13.3 mmoles) compound 31, 1.03 g. (14.0 mmoles) pyrrolidine, and 900 mg. (14.0 mmoles) acetic acid in 50 ml. of benzene was refluxed 18 hours. The solvent was evaporated at reduced pressure and the residual oil was taken up in 60 ml. of chloroform. The chloroform solution was washed with water (15 ml.), brine, and dried over MgSO$_4$. The drying agent was filtered off and the filtrate evaporated to dryness to give 3.50 g. (71% yield) of crystalline enamine 32, m.p. 111.5° - 112.5° C. The NMR and Ir spectra were compatible with the assigned structure.

Anal. Calcd for $C_{18}H_{21}N_5O_4$: C, 58.21; H, 5.70; N, 18.86. Found: C, 58.23; H, 5.72; N, 19.10.

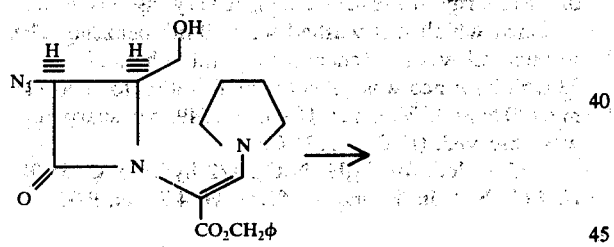

Procedure:

A solution of 2.44 g. (6.6 mmoles) compound 32, 3.9 g. (33 mmoles) methane sulfonyl chloride and 3.3 g (33 mmoles) triethylamine in 50 ml. methylene chloride was stirred at ambient (25° C.) temperature for 74 hours. The reaction mixture was washed with water (2 × 10 ml.), brine, and dried over Na$_2$SO$_4$. The drying agent was filtered off and the filtrate evaporated to dryness. The oil was filtered through a silica gel column (deactivated — 15% water) (16 g.) with chloroform to give 2.6 g. (90%) of crystalline mesylate 33, m.p. 116° - 117.5° C. The IR and NMR spectra were compatible with the assigned structures.

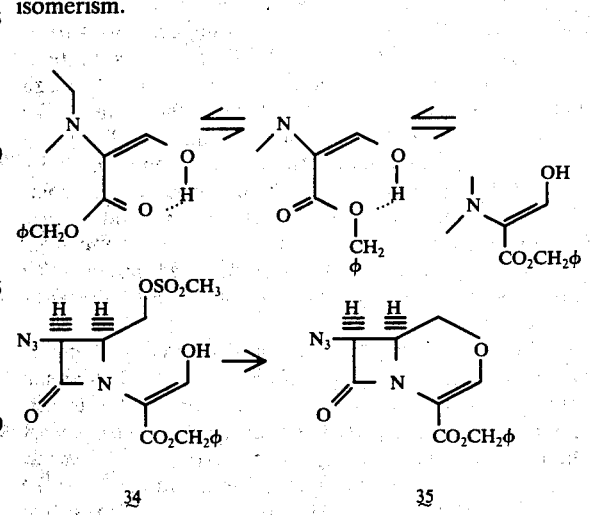

Procedure:

A solution of 2.28 g. (5.26 mmoles) compound 33 in 25 ml. of acetone and 25 ml. 10% hydrochloric acid was refluxed 15 minutes. The acetone was evaporated at reduced pressure and the residue extracted with chloroform (3 × 30 ml.). The chloroform layer was washed with water and evaporated to dryness. The residual oil was dissolved in ether (20 ml.) and the solution extracted with saturated sodium bicarbonate solution (4 × 8 ml.). The bicarbonate was acidified to pH 4 with 10% HCl and re-extracted with chloroform (3 × 50 ml.). The choroform was washed with water, brine and dried over MgSO$_4$. The drying agent was filtered off and the filtrate evaporated to give 1.62 g. (81%) of compound 34. The IR and NMR spectra of 34 were compatible with the assigned structure.

The NMR spectrum of 34 shows two signals for the benzyl group. This may be due to two causes — hydrogen bonding causing restricted rotation or geometrical isomerism.

Procedure:

To a suspension of 198 mg (4.70 mmoles) sodium hydride (55% mineral oil dispersion, washed 3X with petroleum ether) in 5 ml. dry dimethyl sulfoxide (DMSO) was added a solution of 1.62 g. (4.27 mmoles) compound 34 in 5 ml. DMSO over 5 min. with stirring at 25° C. [Gas evolution was observed to cease after 15 - 20 minutes. Prolonged reaction times gave lower yields of 35. The optimum time was 45-60 minutes.] After 1 hour, the reaction mixture was poured into 50 ml. 1% HCl-ice water and was extracted with chloroform (4 × 30 ml.). The organic layer was washed with water (3 × 10 ml.) brine, and dried over MgSO$_4$. Filtration and evaporation of the filtrate gave 1.2 g. of 35 as an oil. Trituration with ether caused crystallization; 545 mg., m.p. 110°, of 35 were collected. The NMR and IR spectra were compatible with the assigned structure.

Anal. Calcd. for C$_{14}$H$_{12}$N$_4$O$_4$: C, 55.99; H, 4.03; N, 18.66. Found: C, 55.23; H, 4.02; N, 18.91.

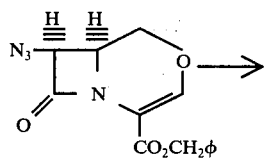

35

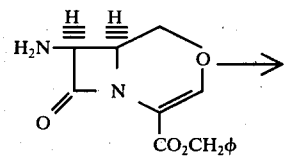

36

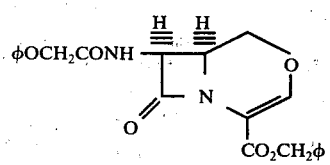

37

procedure:

A. Compound 35 (500 mg.; 1.66 mmoles) was dissolved in 20 ml. of dry ethyl acetate. To this was added 450 mg. of 10% Pd/C and the solution was stirred under hydrogen at atmospheric pressure and room temperature for 30 min. The solution was filtered through diatomaceous earth ("Celite") and the filter cake washed thoroughly with methyllene chloride. Evaporation of the filtrate yielded 500 mg. of crude amine 36. The NMR and IR spectra of the compound were compatible with the assigned structure. Compound 36 was used in the subsequent step without further purification. [On standing some decomposition was noted. The amine should be used as soon as possible after preparation.]

B. Compound 36 (500 mg.) was dissolved in 10 ml. of dry methylene chloride and cooled to 0°-5° C. in an ice bath. To this was added 280 mg. (2.8 mmoles) of triethylamine and 346 mg. (2.0 mmoles) of phenoxyacetyl chloride was added slowly. After stirring for 1 hour at 0°-5° C. the solution was washed with water (2 + ml.) and dried over Na$_2$SO$_4$. After evaporation the residual oil was taken up in 50 ml. of ether and filtered. The filtrate was evaporated and triturated with ether-petroleum ether (1:1). The solid thus obtained was colleced by filtration to yield 570 mg. crude amide 37. The amide was chromtographed on a silica gel column (un-deactivated) (25 g.) with benzene-acetone (initially in a ratio 50:1, gradually changed to 1:1 - 2% more acetone every 25 ml.). The desired amide 37 was obtained pure, 195 mg.

The NMR and IR spectra were compatible with the assigned structure.

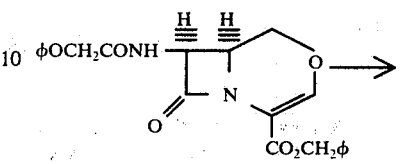

37

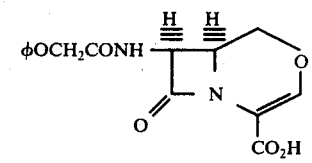

38

Procedure:

Compound 37 (210 mg.; 0.514 mmoles) was dissolved in 40 ml. ethyl acetate and 1 ml. glacial acetic acid was added. Using 610 mg. (~20%) palladium hydroxide on charcoal as catalyst, the solution was hydrogenated at 58 psi for 50 minutes.

The reaction mixture was filtered through "Celite" (twice) and the catalyst was washed thoroughly with chloroform (20 ml.). The filtrate was evaporated to dryness and then evaporated 3 times with benzene in order to strip off the acetic acid. A very viscous oil was obtained which was washed with 10 ml. benzene. The residual oil was scratched with 10 ml. ether. The solid 38 which formed was collected by filtration to yield 115 mg. (70.5%). U.V. λmax. 168, ε = 9549. No. sharp m.p. was observed. (D.P. <252° C.)

Anal. Calcd. for C$_{15}$H$_{14}$N$_2$O$_6$. 1/2 hydrate: C, 55.06; H, 4.62; N, 8.56. Found: C, 55.19; H, 4.70; N, 9.00.

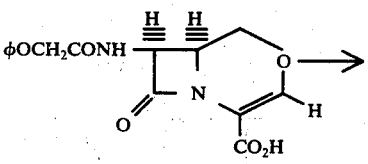

38

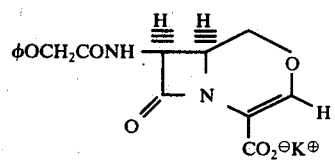

39

Procedure:

To a solution of 30 mg. compound 38 in 3 ml. methyl isobutyl ketone was added one or two drops of 50% solution of potassium 2-ethylhexanoate in butanol. A white crystalline material separated almost immediately which was collected by filtration, washed with methyl isobutyl ketone and dried over P$_2$O$_5$ for 48 hours under high vacuum to yield 18 mg.

39 (53.5%).

U.V. λmax. 265, ε 5528.

No sharp m.p. or d.p. could be observed.

Anal. Calcd. for C$_{15}$H$_{13}$N$_2$O$_6$K·1/2 H$_2$O: C, 49.31; H, 3.82; N, 7.67. Found: C, 49.35 H, 3.94; N, 8.21.

A sample of compound 39 prepared above which can be named potassium 7 β-phenoxyacetamido-Δ$^3$-O-2-isocephem-4-carboxylate (called BC-L2) after solution in water and dilution with Nutrient Broth was found to exhibit the following Minimum Inhibitory Concentrations (M.I.C.) in mcg./ml. versus the indicated microorganisms as determined by overnight incubation at 37° C. by Tube Dilution. One old, orally absorbed cephalosporin (cephalexin) was included.

Table 5

| | M.I.C. in mcg./ml. | |
|---|---|---|
| Organism | BC-L2 | Cephalexin |
| D. pneumoniae +5% serum* | A9585 | .6 | .6 |
| Str. Pyogenes +5% serum* | A9604 | .6 | .3 |
| S. aureus Smith+ | A9537 | 1.3 | 1.3 |
| S. aureus Smith+ +50% serum | A9537 | 1 | 2.5 |
| S. aureus BX1633-2 at 10$^{-3}$ dil'n | A9606 | 2.5 | 4 |
| S. aureus BX1633-2 at 10$^{-2}$ dil'n | A9606 | >125 | 8 |
| Sal enteritidis+ | A9531 | 16 | 4 |
| E. coli Juhl+ | A15119 | 63 | 8 |
| E. coli+ | A9675 | >125 | 16 |
| K. pneumoniae+ | A9977 | 32 | 8 |
| K. pneumoniae+ | A15130 | >125 | 16 |
| pr. mirabilis+ | A9900 | 63 | 4 |
| Pr. morganii+ | A15153 | >125 | >125 |
| Ps. aeruginosa+ | A9843A | >125 | >125 |
| Ser. marcescens+ | A20019 | >125 | >125 |
| S. aureus meth.-resist; at 10$^{-3}$ dil'n | A15097 | >125 | 32 |

*50% Nutrient Broth - 45% Antibiotic Assay Broth at 10$^{-4}$ dilution

EXAMPLE 8

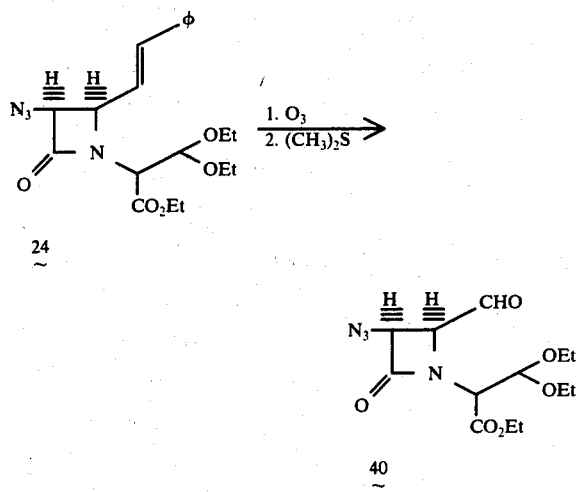

24

40

Procedure:

A solution of 43.0 g. (0.107 mole) of compound 24 (as prepared by the method of Example 7) in 700 ml. of dry methylene chloride was cooled to −78° C. in an acetone dry ice bath and a stream of ozone passed through for 2 hours. At the end of this time the solution turned bluish-green and the ozone was replaced by a stream of dry nitrogen. When the excess ozone had been purged (as indicated by the disappearance of the blue color) 30 ml. of dimethyl sulfide was added. The solution was allowed to come to room temperature (∼25° C.) over 1 hour. The solution was evaporated to dryness and the residue redissolved in 800 ml. CH$_2$Cl$_2$. The solution was washed with water, brine and dried over MgSO$_4$. Evaporation of the solution gave an oily residue which was distilled for 18 hours at 40°− 50° C. and 0.1 mmHg to remove benzaldehyde. This yielded 40.5 g. of 40 as an oil. The NMR spectrum indicated 76% free aldehyde. The crude aldehyde was used in the next step without further purification.

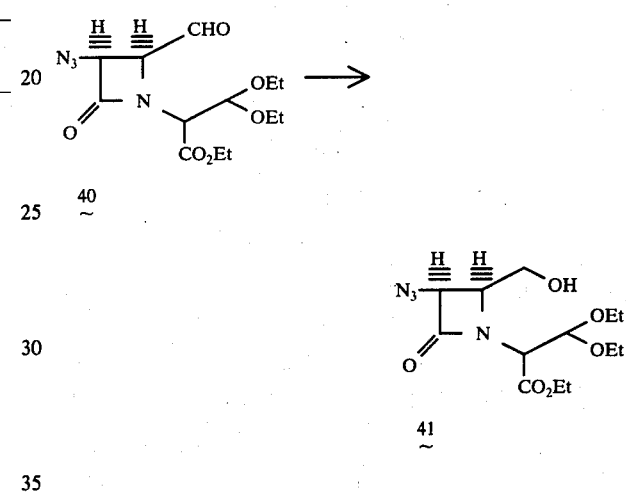

40

41

Procedure:

A solution of 40.3 g. of compound 40 in 250 ml. ethanol −12.5 ml. H$_2$O was prepared and cooled to 0-5° C. in an ice bath. To this was added 1.56 g. (0.041 moles) sodium borohydride and the solution was stirred for 30 min. at 0°-5° C. To the solution was added 10% hydrochloric acid to pH 4. The reaction mixture was evaporated to dryness at reduced pressure below 35° C. To the residue was added 200 ml. of brine and the solution was extracted with chloroform (3 × 200 ml.). The extracts were dried over Na$_2$SO$_4$, filtered and evaporated to yield 37.0 g. of crude alcohol 41. The crude alcohol was filtered through a column of activity III alumina (550 g.) using chloroform as an eluent to yield 27.0 g. of reasonably pure alcohol "(>90%). The IR and NMR spectra of the oil were compatible with the assigned structure.

The overall yield from compound 24 was 76.5%. It has been found that the ozonolysis and reduction procedure can be combined by carrying out the oxidation in ethanol and reducing the ozonide in situ with NaBH$_4$. This gives an 83-85% yield of equimolar amounts of 41 and benzyl alcohol. A small sample of the alcohol was purified by column chromatography on alumina (Act II).

NW — 330.351.

Anal. Calcd. for C$_{13}$H$_{22}$N$_4$O$_6$: C, 47.27; H, 6.71; N, 16.96. Found: C, 47.26; H, 6.85; N, 17.15.

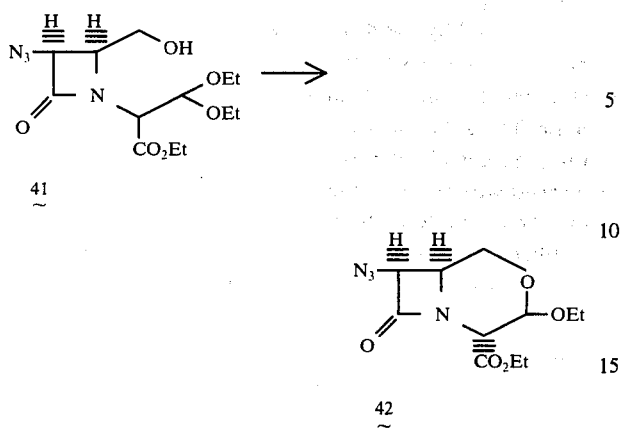

41

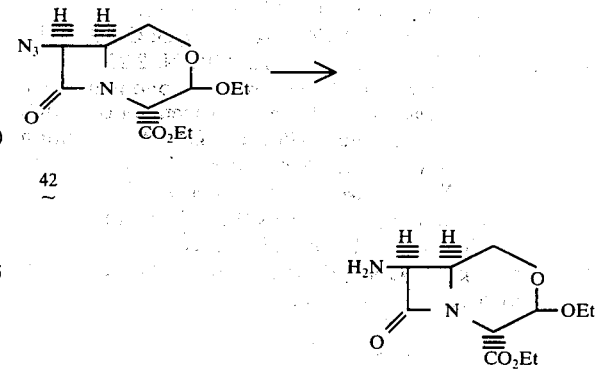

42

Procedure:

To a solution of 6.20 g. (18.8 mmole) of alcohol 41 in 100 ml. of dry methylene chloride was slowly added a solution of 4.0 g. (28.2 mmole, 3.54 ml.) boron trifluoride etherate in 20 ml. dry methylene chloride over 15 min. at 0°–5° C. The cooling bath was removed and stirring was continued for 18 hours. The reaction mixture was filtered through a column of activity III alumina (40 g.). The column was washed with 300 ml. chloroform. The eluted fractions were evaporated to dryness to yield 6.0 g. of 42 as an oil which by TLC analysis was at least 90% pure. The NMR and IR spectra were compatible with the assigned structure [In contrast to the methyl ester dimethyl acetal analog of 41 only one isomer was obtained on cyclization. Careful chromatography of 42 gave a 76% yield of one pure isomer with the stereochemistry indicated in the figure. A small sample was rechromatographed for analysis.

Anal. Calcd for $C_{11}H_{16}N_4O_5$: C, 46.47; H, 5.67; N, 19.71. Found: C, 46.54; H, 5.85; N, 19.34.

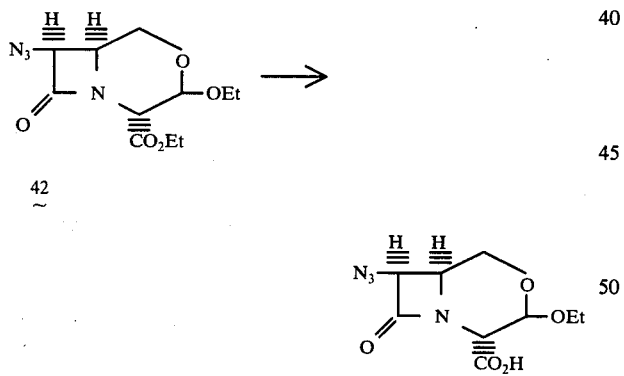

42

Procedure:

To a solution of 12.2 g. (43 mmoles) of compound 42 in 180 ml. ethanol was added 175 ml. 1% sodium hydroxide over a period of 10 min. at <25° C. The solution was stirred an additional 20 minutes. The ethanol was evaporated at reduced pressure and the alkaline solution was extracted with ether (2 × 200 ml.). The organic layer was discarded and the aqueous solution acidified to pH 3–4 with 10% hydrochloric acid. The solution was extracted with chloroform (2 × 100 ml.), the organic layer washed with water (50 ml.), brine (50 ml.), and dried over MgSO₄. Evaporation gave 7.25 g. (66%) of acid 43. Trituration with ether and filtration give pure acid 43, m.p. 114°–115° C. The NMR and IR spectra were compatible with the assigned structure. Anal. Calcd. for $C_9H_{12}N_4O_5$: C, 42.19; H, 4.72; N, 21.87. Found: C, 42.18; H, 4.83; N, 22.01.

42

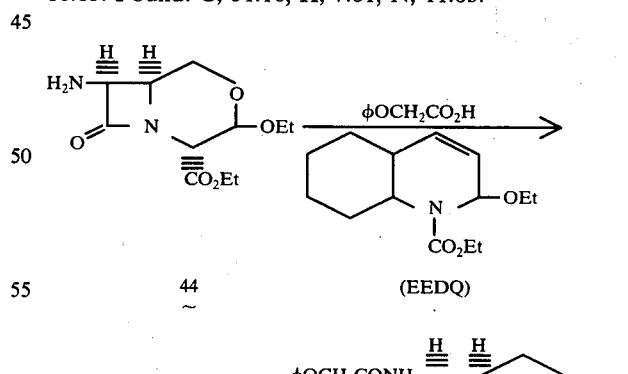

44

Procedure:

A mixture of 760 mg. (2.8 mmole) of compound 42, 925 mg. ammonium chloride (17.1 mmoles) and 620 mg. (17.1 mm.) zinc powder in 35 ml. ethanol was stirred at 25° C. for 3 hours. The reaction mixture was filtered through "Celite" and the filtrate evaporated to dryness. The residue was taken up in chloroform and filtered through 30 g. of Alumina (Act III). Evaporation of the eluent yielded 578 mg. of crude amine 44. The amine was redissolved in 15 ml. chloroform and extracted into 10% HCl (2 × 3 ml.). The aqueous layer was neutralized with sodium bicarbonate and extracted into chloroform. The extracts were dried over Na₂SO₄, filtered, and extracted into chloroform. The extracts were dried over Na₂SO₄, filtered, and evaporated to yield 360 mg. of an oil which crystallized on standing. The amine 44 was recrystallized from ether, m.p. 98.5°–99° C. The IR and NMR spectra were compatible with the assigned structure.

NW = 258.

Anal. Calcd. for $C_{11}H_{18}N_2O_5$: C, 51.15; H, 7.03; N, 10.85. Found: C, 51.16; H, 7.01; N, 11.03.

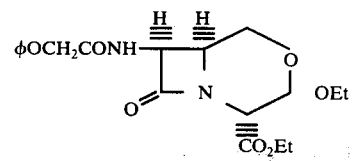

44    (EEDQ)

45

Procedure:

A solution of 400 mg. (1.55 mmole) of compound 44, 410 mg. (1.64 mmole) EEDQ and 250 (1.69 mmole)

phenoxyacetic acid in 20 ml. dry methylene chloride was stirred at 25° C. for a period of 1.5 hours. The reaction mixture was filtered through a column of alumina (activity III 8 g.) and the eluent evaporated to dryness. The resultant solid was washed with ether and collected by filtration to yield 554 mg. (90%), m.p. 162°–164°. Recrystallization from chloroform-ether gave analytically pure amide 45, m.p. 166.5°–167.5° C. The IR and NMR spectra were compatible with the assigned structure. NW = 392.417

Anal Calcd. for $C_{19}H_{24}N_2O_7$: C, 58.15; H, 6.16; N, 7.14. Found: C, 57.93; H, 6.23; N, 7.34.

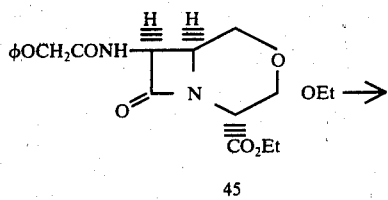

45

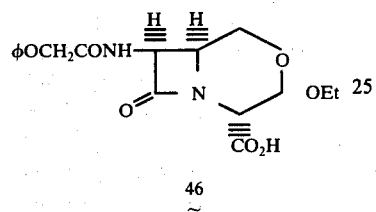

46

Procedure:

A solution of 392 mg. (1 mmole) compound 45 in 13 ml. warm methanol was added to 12 ml. 1% NaOH at 25° C. with stirring over 10 min. After 1 hour the methanol was evaporated and the alkaline solution was extracted with chloroform (2 × 20 ml.). The aqueous solution was acidified to pH ~ 4 with 10% HCl and extracted with chloroform (2 × 15 ml.). The extracts were washed with water, dried over $Na_2SO_4$, filtered, and evaporated to give 200 mg. (55%) of a white solid. Recrystallization from methanol-ether gave pure acid 46, m.p. 150°–151.5° C. The IR and NMR spectra were compatible with the assigned structures.

NW = 364.363

Anal. Calcd. for $C_{17}H_{20}N_2O_7 \cdot 0.5\ CH_3OH$: C, 55.26; H, 5.83; N, 7.37. Found: C, 55.08; N, 5.53; N, 7.48.

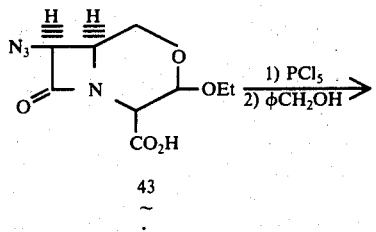

43

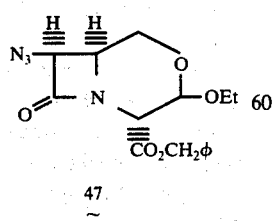

47

Procedure:

To a solution of 0.25 g. (25.6 mmoles) of compound 43 in 100 ml. of ether was added 5.35 g. (25.6 mmoles) phosphorous pentachloride. The suspension was refluxed for 15 min. after which the clear solution was decanted and evaporated to dryness. The residual oil was taken up in 50 ml. benzene and evaporated to dryness at reduced pressure. This procedure was repeated three times to remove phosphorous oxychloride. The residual oil was then pumped in high vacuum (0.05 mm Hg) at 30° C. for 1 hour. The NMR and IR spectra were compatible for the desired acid chloride.

The acid chloride was taken up in 20 ml. dry methylene chloride and was added to a mixture of 2.7 g. (26 mmole) benzyl alcohol and 3.2 g. triethylamine in 50 ml. dry methylene chloride at 25° C. over a period of 10 minutes. The solution was stirred for 1 hour, washed with water (2 × 20 ml.), brine and filtered through 20 g. of "Florisil." The eluent was treated with charcoal (Norite), dried over $MgSO_4$, filtered and evaporated to give 7.4 g. (83.5%) of crude benzyl ester 47. Trituration with benzene-petroleum ether caused crystallization. The solid was recrystallized from benzene-petroleum ether to yield pure 47, m.p. 79°–79.5° C. The IR and NMR spectra were compatible with the assigned structure.

NW = 346.352

Anal. Calcd. for $C_{16}H_{18}N_4O_5$: C, 55.49; H, 5.24; N, 16.18. Found: C, 55.81; H, 5.36; N, 16.40.

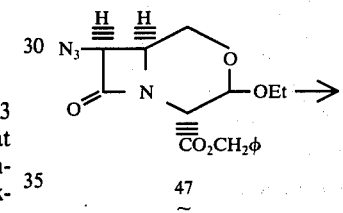

47

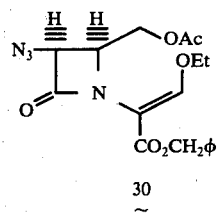

30

Procedure:

A mixture of 6.5 g. (18.8 mmole) compound 47, 50 ml. acetic anhydride, and 5.1 g. (37.6 mm) zinc chloride was stirred at 0°–5° C. for 30 min. then at 25° C. for 18 hours. The reaction mixture was evaporated to dryness at reduced pressure and the residue taken up in 200 ml. methylene chloride–50 ml. water. The organic phase was separated, washed with water, brine, and dried over $MgSO_4$. Filtration and evaporation of the filtrate gave an oily residue which was chromatographed on 60 g. alumina (Activity III) with chloroform to yield 5.35 g. (73%) of compound 30 identical in all respects with that obtained earlier.

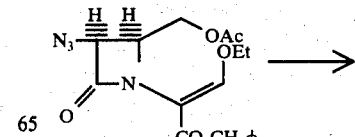

30

-continued

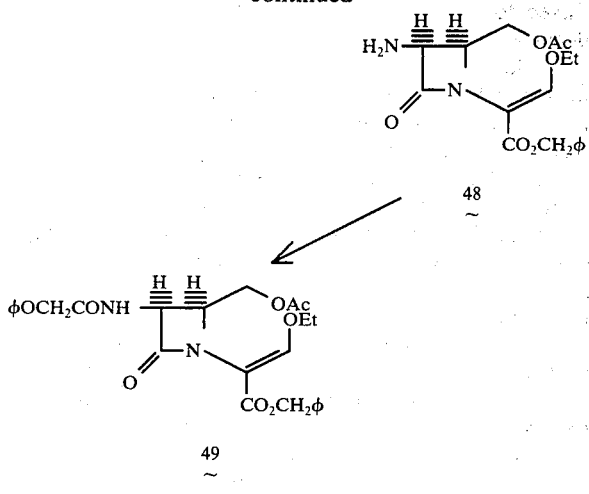

Procedure:

To 325 mg. (0.84 mmole) of compound 30 in 5 ml. dry methanol was added 325 mg. zinc powder and 300 mg. ammonium chloride at 0°–5° C. The suspension was stirred for 1 hour, filtered, and the filtrate evaporated to yield 312 crude amine 48. The IR spectrum indicated complete reduction of the azido function.

The crude amine 48 was treated with 140 mg. (0.92 mmole) phenoxyacetic acid and 230 mg. (0.92 mmole) EEDQ in 10 ml. methylene chloride at 25° C. for 1 hour. The solution was washed with 10% HCl (5 ml.), water (5 ml.), brine, dried over Na₂SO₄, filtered, and the filtrate evaporated. The crude amide 49 was chromatographed on alumina (Activity III) using chloroform as eluent to give 230 mg. pure amide 49 and an additional 100 mg. of ~80% pure amide. The NMR and IR spectra were compatible with the assigned structures.

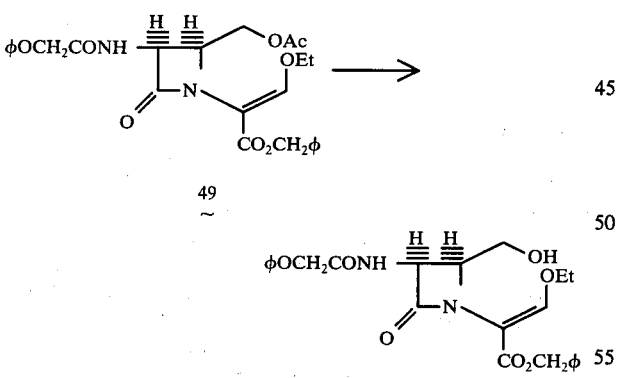

Procedure:

A solution of 110 mg. (0.222 mmole) of 49 in 4 ml. methanol and 2 ml. 10% hydrochloric acid was refluxed for 1 hour, diluted to 20 ml. with water and extracted into chloroform. The extracts were dried over Na₂SO₄, filtered, and evaporated to yield 74 mg. (75%) of the desired alcohol 50. The NMR and IR spectra were compatible with the assigned structure.

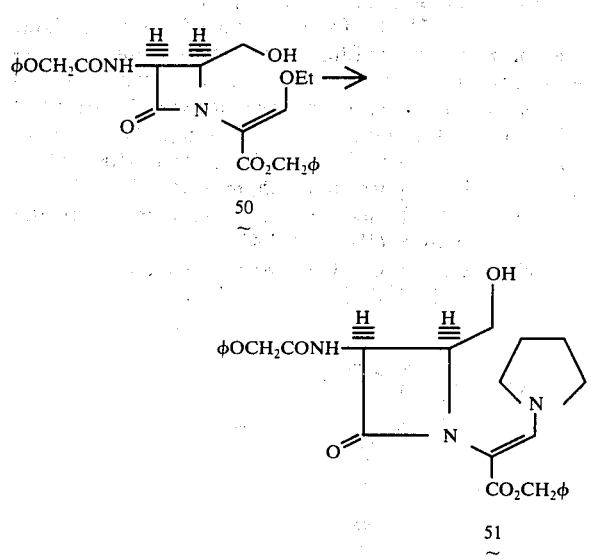

Procedure:

A solution of 140 mg. (0.31 mmole) compound 50, 140 mg. acetic acid, and 140 mg. pyrrolidine in 10 ml. benzene was boiled at reflux for 16 hours. The solution was evaporated to dryness, taken up in chloroform (20 ml.), washed with water (5 ml.), 10% HCl (5 ml.), saturated NaHCO₃ solution (5 ml.), brine (5 ml.), dried over Na₂SO₄, filtered, and evaporated to yield 157 mg. crude enamide 51 (100%). The IR and NMR spectra were compatible with the assigned structure.

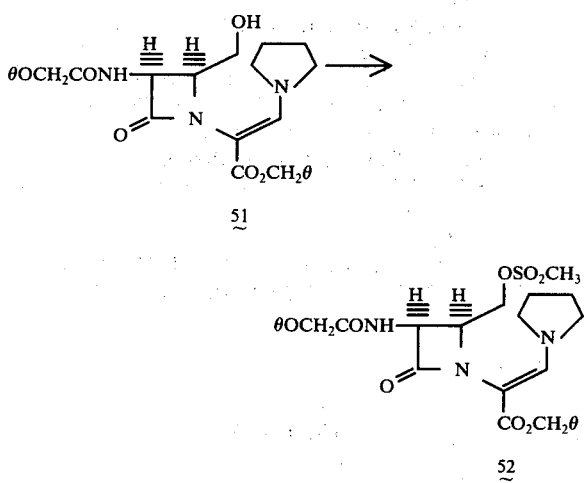

Procedure:

To a solution of 157 mg. (0.31 mmole) of crude 51 and 0.5 ml. pyridine in 5 ml. methylene chloride was added 170 mg. of methane sulfonyl chloride at 0°–5° C. The solution was stirred at 25° C. for 48 hours, evaporated at reduced pressure, taken up in chloroform, washed with water and dried over Na₂SO₄. The solution was filtered and passed through a short column of alumina (5 g. Activity III) with chloroform as eluent. Evaporation of the eluted fraction gave 170 mg. (>90%) crude mesylate 52. The NMR and IR spectra of 52 were compatible with the assigned structure.

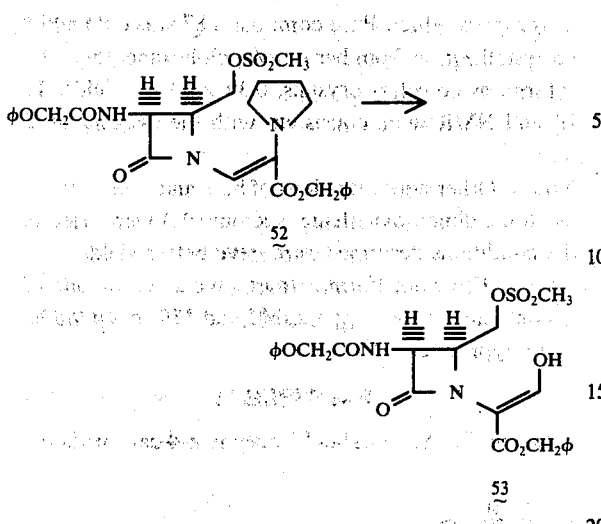

Procedure:

A solution of 200 mg. compound 52 in 6 ml. acetone and 1.5 ml. 10% HCl was refluxed for 15 min., diluted to 50 ml. with water and extracted into chloroform (3 × 25 ml.). The extracts were evaporated and the residue redissolved into chloroform which was extracted with sodium bicarbonate solution. The aqueous layer was acidified to pH ~ 4 with 10% HCl and extracted into chloroform (3 × 25 ml.). The extracts were dried over $Na_2SO_4$, filtered, and evaporated to yield 180 mg. crude enol 53. The NMR and IR spectra were compatible with the assigned structure.

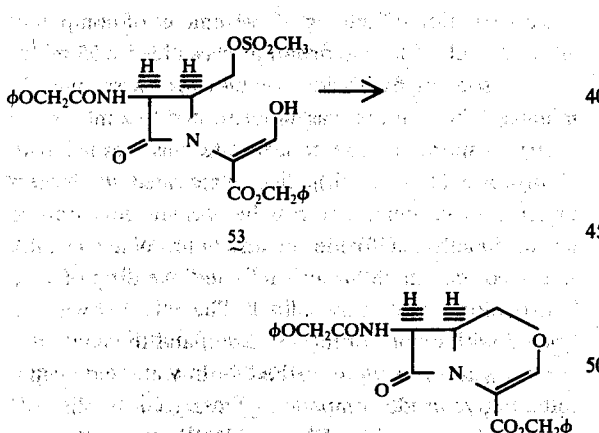

Procedure:

Compound 53 (70 mg.) was treated for 1 hour with 5.6 mg. (60% mineral oil dispersion - washed with petroleum-ether) of sodium hydride in 2 ml. DMSO at 25° C. The solution was poured into 20 ml. ice cold 1% HCl and extracted into chloroform (3 × 10 ml.). The solution was washed with water (2 × 10 ml.), brine (10 ml.), dried over $Na_2SO_4$, filtered, and evaporated to give 60 mg. of crude 37 identical in all respects to that obtained via acylation of 36.

EXAMPLE 9

Benzyl 7β-Azido-Δ³-0-2-isocephem-4-carboxylate

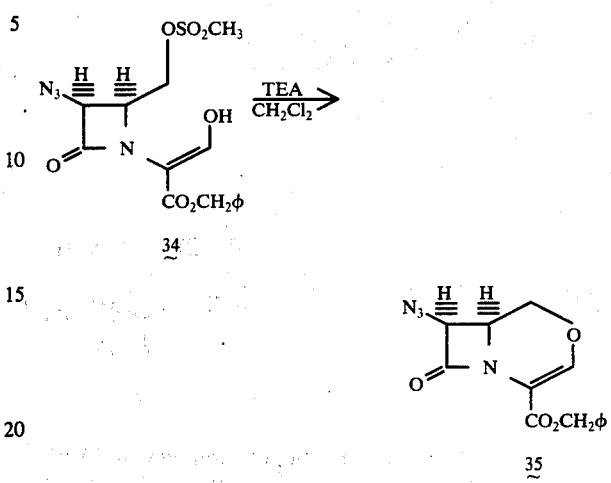

A solution of 682 mg. (0.00174 moles) of 34 and 195 mg. (0.00192 moles) TEA in 10 ml. $CH_2Cl_2$ was refluxed for 5 hours. The solution was washed with water, brine, dried over $Na_2SO_4$, filtered and evaporated to yield an oil. Trituration with ether and filtration gave 393 mg. (75.5%) pure 35. An additional 21.0 mg. were recovered from the mother liquors. Compound 35 prepared in this manner was identical in all respects with that obtained earlier (m.p., IR and NMR).

EXAMPLE 10

Ethyl 7β-Azido-Δ³-0-2-isocephem-4-carboxylate

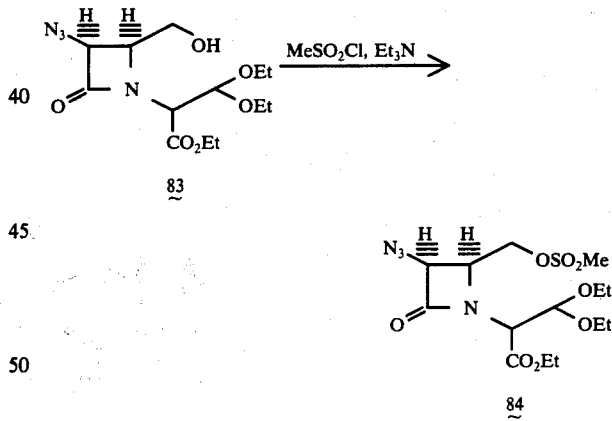

To a solution of 9.6 g. (29 mmole) of compound 83 (note 1) and 9.0 ml. of triethylamine in 96 ml. of methylene chloride at 0°–5° was added dropwise a solution of 4.8 g. (42 mmole) of methanesulfonyl chloride in 24 ml. of methylene chloride. After standing at 25° for one hour, the solution was washed with equal volumes of water and 10% hydrochloric acid. Evaporation of the solvent gave a yellow oil which was chromatographed on 180 g. of alumina (grade III). Elution with chloroform gave the partially purified product 84 as a yellow oil, 5.56 g. (47% yield). The IR and the NMR were consistent with the assigned structure. (Note 2)

Note 1: The purity of the starting material (compound 83) was not known with certainty but it may have been less than 70% pure.

Note 2: The NMR indicated the product was of about 70% purity.

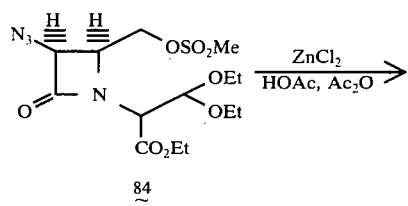

84

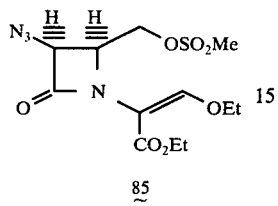

85

A mixture of 4.9 g. (12 mmole) of compoun 84, 10 ml. of acetic anhydride, 10 ml. of acetic acid and 1.75 g. (13 mmole) of zinc chloride was stirred at 25° for 17 hours, then evaporated to a tar. A methylene chloride solution of the tar (50 ml.) was washed with equal volumes of water, 5% sodium bicarbonate and dilute sodium chloride. The methylene chloride solution was filtered through 15 g.. of alumina (grade III) and evaporated to give an oil. Trituration of the oil with ether gave pure compound 85 as a colorless powder, 1.88 g. (45% yield). The IR and NMR were consistent with the assigned structure.

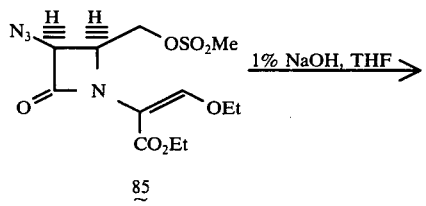

85

86

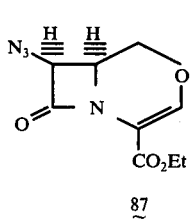

87

To a solution of 1.83 g. (5.99 mmole) of compound 85 in 20 ml. of tetrahydrofuran was added 20.0 ml. of 0.25M sodium hydroxide (Note 1) solution dropwise over 10 minutes. The resulting solution was concentrated to 20 ml. on the rotary evaporator at 30°. The concentrate was washed with chloroform (3 × 10 ml.) (Note 2). The aqueous layer was evaporated to dryness under high vacuum. The resulting residue (sodium enolate 86) was stirred with 7.5 ml. of dimethyl sulfoxide for one hour. Water (30 ml.) and saturated sodium chloride (40 ml.) followed by a few drops of 10% hydrochloric acid were added to the dimethylsulfoxide solution. The resulting mixture was extracted with chloroform (3 × 40 ml.) and the combined chloroform layers were washed with ater and evaporated to give the crude product. Pure compound 87 was obtained by recrystallization from benzene/cyclohexane, then chloroform, as colorless crystals, 0.39 g. (33% yield). The IR and NMR were consistent with the assigned structure.

Note 1: Other concentrations of base and other solvents (acetone, dimethoxyethane, acetonitrile) were tried but the conditions described here gave better yields.

Note 2: The chloroform extract gave a yellow oil, 0.58 g. containing 65% compound 85 and 35% of an unidentified byproduct.

EXAMPLE 11

Benzyl 7β-Azido-Δ³-0-2-isocephem-4-carboxylate

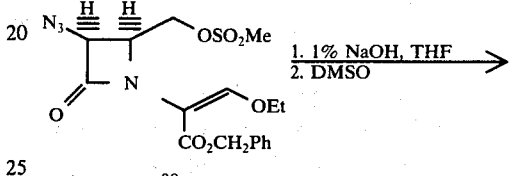

88

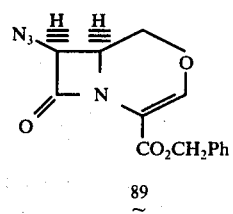

89

To a solution of 260 mg. (0.64 mmole) of compound 88 in 2.5 ml. of tetrahydrofuran was added 2.55 ml. of 0.25 M sodium hydroxide solution dropwise over 10 minutes. The solution was concentrated to 2 ml. on the rotary evaporator. The concentrate was washed with chloroform (2 × 2 ml.), then evaporated to dryness under high vacuum. The residue was stirred with one ml. of dimethyl sulfoxide for one hour. Water (1 ml.), saturated sodium chloride (1 ml.) and one drop of 10% hydrochloric acid were added. The mixture was extracted with chloroform (3 × 2 ml.) and the combined chloroform layers were washed with water and evaporated togive crude compound 89 as a yellow solid, 103 mg. (54% yield). The IR and NMR were consistent with the assigned structure. The NMR indicated the product was about 75% pure (i.e. true yield of 40%).

EXAMPLE 12

7β-Phenoxyacetamido-3-carbomethoxymethylene-Δ³-0-2-isocephem-4-carboxylic acid

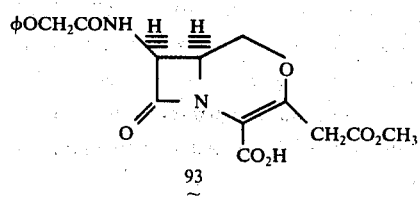

93

-continued

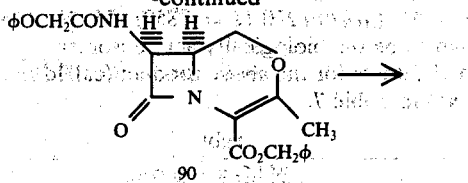
90

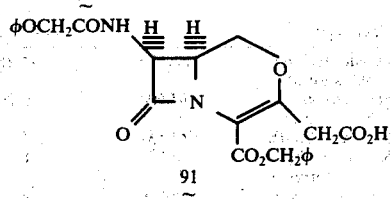
91

Apparatus consisting of a 250 ml. three necked flask equipped with a low temperature therometer, a gas inlet, protected with a gas bubbler (parrafin oil) and magnetic stirring, was dried by heating with a bunsen torch while passing dry nitrogen through the apparatus. It was allowed to cool to 25° C. before being opened, under nitrogen flow, to introduce the reagents.

A solution of benzyl 7-β-[aminophenoxyacetoyl]-3-methyl-Δ³-0-2-isocephem-4-carboxylate 90 (2.11 g.; 5 mmole) in 100 ml. of THF[1] was cooled to −70° under a slow nitrogen stream. A solution of 1.66 M butyl lithium[2] (6.34 ml.; 10.5 mmole) was slowly added keeping the reaction temperature at −70° C. A slow stream of dry carbon dioxide gas was then introduced into the reaction mixture, the cooling bath was removed, and the carbon dioxide introduction continued until the reaction temperature reached 25°.

The reaction mixture was poured into 200 ml. of 10% hydrochloric acid, saturated with sodium chloride, and extracted three times with diethylether (150 ml. portions).

The combined extracts were washed three times with brine, dried (anhydrous sodium sulfate) and evaporated in vacuo to give 2.09 g. of a yellow gum. This gum was partitioned between diethylether and 10% sodium bicarbonate solution three times. The bicarbonate solutions were then washed with diethylether (twice; 50 ml. portions) and with methylene chloride (twice; 50 ml. portions). The bicarbonate solution was then acidified to pH2 with concentrated hydrochloric acid and extracted three times with methylene chloride (100 ml. portions). The methylene chloride extracts were washed twice with brine, dried (anhydrous sodium sulfate), and evaporated in vacuo to give 0.31 g. of a colorless gum. This gum was used as such in the next step.

1. The THF used was reagent grade which had been further dried by passing over an alumina column.
2. Foote Mineral Company

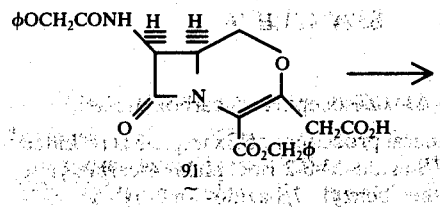
91

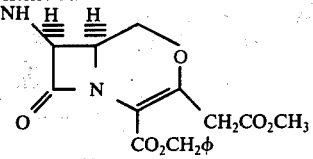
92

A solution of diazomethane in diethylether[1] was slowly added to a solution of benzyl 7-B-[aminophenoxyacetoyl]-3-carboxymethylene-Δ³-0-2-isocephem-4-carboxylate 91 (0.88 g.) in 100 ml. of diethylether, until a permanent yellow color (exces diazomethane) was produced. The reaction mixture was then stirred at room temperature for 10 minutes. The reaction was acidified with 10% hydrochloric acid and extracted twice with 100 ml. portions of diethylether. The extract was washed with 10% sodium bicarbonate solution (twice; 75 ml. portions), with brine (once; 100 ml.), dried (anhydrous sodium sulfate), and evaporated in vacuo to give 0.72 g. of crude product and then dry column chromatograhed over 36 g. of activity III silica gel. Eluton with chloroform gave a fraction containing 240 mg. of methyl ester 92 NMR and IR spectra are in agreement with the assigned structure. This material was used as such in the next step.

1. Prepared from nitrosomethylurea according to A. I. Vogel, "Practical Organic Chemistry," 3rd Edn., Longmans & Green Co., London, 1958, p. 969.

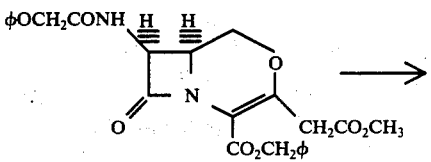
92

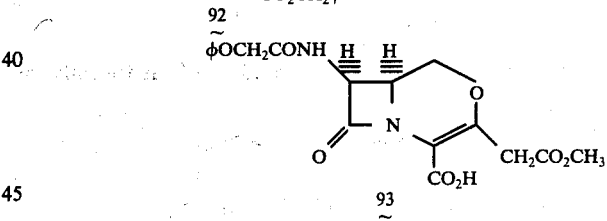
93

A mixture of benzyl 7-β-[aminophenoxyacetoyl]-3-carbomethylene-Δ³-0-2-isocephem-4-carboxylate 92 (147 mg.), 10% Pd-C, (100 mg.), 25 ml. of ethanol (USP) and 15 ml. of THF was hydrogenated in a Parr hydrogenator at 17 psig for 1 hour. The catalyst was filtered off and the filtrate evaporated to dryness in vacuo togive 87 mg. of a white foam.

The potassium salt of acid 93 was prepared by dissolving the foam in a small amount of methylisobutylketone and adding a saturated solution of potassium 2-ethylhexanoate in butanol. The resultant precipitate was filtered off and washed with methylisobutylketone and then diethylether.

M.P. 139°–145° C. with decomposition (cor.). Spectral data confirm structure assignment.

Anal.Calc'd. for $C_{18}H_{17}KN_2O_8 \cdot 1/2H_2O$: C, 49.42; H, 4.15; N, 6.40. Found: C, 49.05; H, 4.07; N, 6.29.

A sample of compound 93 prepared above (called BC-L33) after solution in water and dilution with Nutrient Broth was found to exhibit the following Minimum Inhibitory Concentrations (M.I.C.) in mcg./ml. versus the indicated microorganisms as determined by overnight incubation at 37° C. by tube dilution. Cephalexin was included as a comparison compound.

Table 6

| Organism | | M.I.C. in mcg./ml. | |
|---|---|---|---|
| | | BC-L33 | Cephalexin |
| D. pneumoniae +5% serum* | A9585 | .06 | .16 |
| Str. pyogenes +5% serum* | A9604 | .06 | .16 |
| S. aureus Smith+ | A9537 | .25 | .6 |
| S. aureus Smith+ +50% serum | A9537 | 1 | 1.3 |
| S. aureus BX1633-2 at 10⁻³ dil'n | A9606 | 16 | 2 |
| S. aureus BX1633-2 at 10⁻² dil'n | A9606 | >125 | 4 |
| S. aureus meth.-resist; at 10⁻³ dil'n | A15097 | >125 | 32 |
| Sal. enteritidis+ | A9531 | 8 | 1 |
| E. coli Juhl+ | A15119 | 125 | 4 |
| E. coli+ | A9675 | >125 | 16 |
| K. pneumoniae+ | A9977 | 63 | 2 |
| K. pneumoniae+ | A15130 | >125 | 8 |
| Pr. mirabilis+ | A9900 | 32 | 2 |
| Pr. morganii+ | A15153 | >125 | >125 |
| Ps. aeruginosa+ | A9843A | >125 | >125 |
| Ser. marcescens+ | A20019 | >125 | >125 |
| Ent. cloacae | A9656 | >125 | >125 |
| Ent. cloacae | A9657 | >125 | 2 |
| Ent. cloacae | A9659 | >125 | >125 |

*50% Nutrient Broth - 45% Antibiotic Assay Broth
+at 10⁻⁴ dilution.

EXAMPLE 13

Separation of Diastereomers of

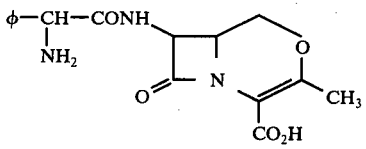

The N-protected benzyl ester (1.3 g.) of the formula

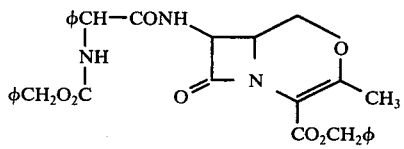

was placed on a silica gel column (340 g. of silica gel - 15% water) and eluted with ether/petroleum ether (30°-60° boiling) 70:30 ratio. Initial fractions consisted entirely of one isomer designated "isomer A", intermediate fractions were mixtures of isomer A and the other isomer designated "isomer B", and later fractions (212 mg.) contained 75-80% isomer B and 20-25% isomer A.

A solution of the isomer B concentrate (150 mg.) in 10 ml. of ethyl acetate plus 10 ml. of 95% ethanol was treated with exactly one equivalent (0.26 ml.) of 1N HCl. To this solution was added 150 mg. of 30% palladium-on-diatomaceous earth and the mixture was hydrogenated at room temperature and atmospheric pressure until uptake of hydrogen ceased. The catalyst was removed by filtration and the solvent evaporated to give 7β-(α-amino-α-phenylacetamido)-3-methyl-Δ³-0-2-isocephem-4-carboxylic acid (75-80% isomer B, 20-25% isomer A) with 1/4 to 1 mole ethanol and 1 to 2 moles H₂O of crystallization per mole of acid. Any attempts at purification led to degradation. The product had U.V. $\lambda_{Max.}^{H_2O}$ 270 ($\epsilon$ = 7850). The B isomer was found to be the biologically active isomer.

M.I.C. data for the above product (called BC-L45) is shown in Table 7.

Table 7

| Organism | | M.I.C. in mcg./ml. | |
|---|---|---|---|
| | | BC-L45 | Cephalexin |
| D. pneumoniae +5% serum* | A9585 | <.25 | .13 |
| Str. pyogenes +5% serum* | A9604 | <.25 | .13 |
| S. aureus Smith+ | A9537 | 1 | .25 |
| S. aureus Smith+ +50% serum | A9537 | 8 | 1 |
| S. aureus BX1633-2 at 10⁻³ dil'n | A9606 | 8 | 1 |
| S. aureus BX1633-2 at 10⁻² dil'n | A9606 | 63 | 4 |
| S. aureus meth.-resist; at 10⁻³ dil'n | A15097 | 63 | 63 |
| Sal. enteritidis+ | A9531 | 4 | 2 |
| E. coli Juhl+ | A15119 | 4 | 8 |
| E. coli+ | A9675 | 32 | 32 |
| K. pneumoniae+ | A9977 | 4 | 4 |
| K. pneumoniae+ | A15130 | 8 | 16 |
| Pr. mirabilis+ | A9900 | 8 | 4 |
| Pr. morganii+ | A15153 | 63 | >125 |
| Ps. aeruginosa+ | A9843A | >125 | >125 |
| Ser. marcescens+ | A20019 | >125 | >125 |
| Ent. cloacae | A9656 | 125 | >125 |
| Ent. cloacae | A9657 | 4 | 4 |
| Ent. cloacae | A9659 | 125 | >125 |

*50% Nutrient Broth - 45% Antibiotic Assay Broth
+at 10⁻⁴ dilution.

Mouse Blood Levels of BC-L45 and cephalexin after oral administration of 100 mg./kg. body weight are shown below:

| Compound | Blood Levels (μg/ml) | | | |
|---|---|---|---|---|
| | 0.5 | 1 | 2 | 3.5 |
| | Hours after administration | | | |
| BC-L45 | 19.4 | 15.7 | 7.3 | 2.9 |
| Cephalexin | 42.4 | 23.7 | 9.8 | 4.0 |

EXAMPLE 14

7β-Amino-3-benzyl-Δ³-0-2-isocephem-4-carboxylic acid

When the general procedure of Example 3 is repeated using benzyl 7β-azido-3-benzyl-Δ³-0-2-isocephem-4-carboxylate in place of the benzyl 7β-azido-3-methyl-Δ³-0-2-isocephem-4-carboxylate used therein, the title product is obtained.

EXAMPLE 15

7β-Amino-3-phenethyl-Δ³-0-2-isocephem-4-carboxylic acid

When the general procedure of Example 3 is repeated using benzyl 7β-azido-3-phenethyl-Δ³-0-2-isocephem-4-carboxylate in place of the benzyl 7β-azido-3-methyl-Δ³-0-2-isocephem-4-carboxylate used therein, the title product is obtained.

EXAMPLE 16

7β-Amino-Δ³-0-2-isocephem-4-carboxylic acid

When the general procedure of Example 3 is repeated using benzyl 7β-azido-Δ³-0-2-isocephem-4-carboxylate in place of the benzyl 7β-azido-3-methyl-Δ³ -0-2-

EXAMPLE 17

Pivaloyloxymethyl 7β-amino-3-methyl-Δ³-0-2-isocephem-4-carboxylate

The title compounds is produced according to the method of Example 2 of U.K. Specification 1,229,453 by replacing the 7-aminocephalosporanic acid used therein by 7β-amino-3-methyl-Δ³-0-2-isocephem-4-carboxylic acid.

The respective acetoxymethyl, methoxymethyl, acetonyl and phenacyl esters of 7β-amino-3-methyl-Δ³-0-2-isocephem-4-carboxylic acid are prepared by substituting in the method above for the chloromethyl pivalate used therein an equimolar weight of chloromethyl acetate, chloromethyl methyl ether, chloroacetone and phenacyl bromide, respectively.

EXAMPLE 18

Pivaloyloxymethyl 7β-amino-Δ³-0-2-isocephem-4-carboxylate

When the procedure of Example2 of U.K. Pat. No. 1,229,453 is repeated using 7β-amino-Δ³-0-2-isocephem-4-carboxylic acid in place of the 7-amino-cephalosporanic acid used therein, there is produced pivaloyloxymethyl 7β-amino-Δ³-0-2-isocephem-4-carboxylate.

The respective acetoxymethyl, methoxymethyl, acetonyl and phenacyl esters of 7β-amino-Δ³-0-2-isocephem-4-carboxylic acid are prepared by substituting in the method above for the chloromethyl pivalate used therein an equimolar weight of chloromethyl acetate, chloromethyl methyl ether, chloroacetone and phenacyl bromide, respectively.

EXAMPLE 19

Pivaloyloxymethyl 7β-amino-3-benzyl-Δ³-0-2-isocephem-4-carboxylate

When the procedure of Example 2 of U.K. Pat. No. 1,229,453 is repeated using 7β-amino-3-benzyl-Δ³-0-2-isocephem-4-carboxylic acid in place of the 7-aminocephalosporanic acid used therein, there is produced the title product.

The respective acetoxymethyl, methoxymethyl, acetonyl and phenacyl esters of 7β-amino-3-benzyl-Δ³-0-2-isocephem-4-carboxylic acid are prepared by substituting in the method above for the chloromethyl pivalate used therein an equimolar weight of chloromethyl acetate, cloromethyl methyl ether, chloroacetone and phenacyl bromide, respectively.

EXAMPLE 20

Pivaloyloxymethyl 7β-amino-3-phenethyl-Δ³-0-2-isocephem-4-carboxylate

When the procedure of Example 2 of U.K. Pat. No. 1,229,453 is repeated using 7β-amino-3-phenethyl-Δ³-0-2-isocephem-4-carboxylic acid in place of the 7-aminocephalosporanic acid used therein, there is produced the title product.

The respective acetoxymethyl, methoxymethyl, acetonyl and phenacyl esters of 7β-amino-3-phenethyl-Δ³-0-2-isocephem-4-carboxylic acid are prepared by substituting in the method above for the chloromethyl pivalate used therein an equimolar weight of chloromethyl acetate, chloromethyl methyl ether, chloroacetone and phenacyl bromide, respectively.

isocephem-4-carboxylate used therein, the title product is obtained.

EXAMPLE 21

7β-(D-α-aminophenylacetamido)-Δ³-0-2-isocephem-4-carboxylic acid

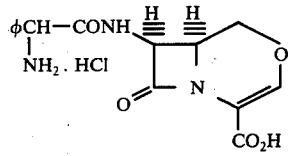

Benzyl 7β-azido-Δ³-0-2-isocephem-4-carboxylate (300.3 mg., 1 mmole) and 300 mg. 10% Pd/C in 40 ml. ethyl acetate was shaken under $H_2$ for 45 minutes at 60 psi. The suspension was filtered through celite and evaporated to dryness. The IR spectrum of residue indicated complete reduction of azido function to benzyl 7β-amino-Δ³-0-2-isocephem-4-carboxylate.

The above-mentioned benzyl 7-amino intermediate was dissolved in 25 ml. $CH_2Cl_2$ and treated with 285 mg. (1 mmole) N-carbobenzoxy-D-phenyl glycine and 247.3 mg. (1 mmole) EEDQ for 2 hours. The solution was washed with 10% HCl (2 × 30 ml.), saturated aqueous $NaHCO_3$ and brine. The crude amide was chromatographed on silica gel and eluted with $CH_2Cl_2$. The IR and NMR spectra indicated formation of the N-protected compound of the formula

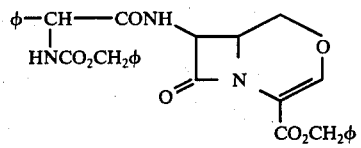

A suspension of the above N-protected compound (308.5 mg., 0.570 mmole) and 900 mg. 20% Pd $(OH)_2$/C in a mixture of 40 ml. ethyl acetate and 1 ml. acetic acid was shaken under $H_2$ at 60 psi for 1 hour. The suspension was filtered through celite (filter cakes washed with 200 ml. $CH_2Cl_2$) and evaporated to yield the free carboxylic acid of the above N-protected ester.

U.V. $\lambda_{Max}^{EtOH}$ 264, ε = 5203

Anal. Calc'd for $C_{22}H_{21}N_3O_7 \cdot 1/2H_2O$: C, 58.92; H, 4.97; N, 9.37. Found: C, 59.12; H, 4.95; N, 8.95.

A suspension of 305 mg. (0.695 mmole) of the above free acid, 59 mg. anhydrous $NaHCO_3$ and 300 mg. 30% Pd/diatomaceous earth in 25 ml. $H_2O$-15 ml. dioxane (pH 7-7.5) was agitated under $H_2$ at 60 psi for 45 minutes. The suspension was filtered (filter cake washed with 50 ml. MIBK and 10 ml. water) and filtrate was stirred for 20 minutes (pH 7.0). The organic layer was separated and the pH of the aqueous layer adjusted to 3.75 with HCl. The solvent was pumped under high vacuum (freeze-dried) for 21.5 hours to give 200 mg. of the title product as a pale yellow powder.

U.V. $\lambda_{Max}^{EtOH}$ = 261, ε = 1000.

A sample of the title product (called BC-L6) after solution in water and dilution with Nutrient Broth was found to exhibit the following Minimum Inhibitory Concentrations (M.I.C.) in mcg./ml. versus the indicated microorganisms as determined by overnight incubation at 37° C. by tube dilution. Cephalexin was included as a comparison compound.

Table 8

| Organism | | M.I.C. in mcg./ml. | |
|---|---|---|---|
| | | BC-L6 | Cephalexin |
| D. pneumoniae —5% serum* | A9585 | 16 | .3 |
| Str. pyogenes —5% serum* | A9604 | 16 | .3 |
| S. aureus Smith= | A9537 | 32 | 1.3 |
| S. aureus Smith= —50% serum | A9537 | 250 | 5 |
| S. aureus BX1633-2 at $10^{-3}$ dil'n | A9606 | 125 | 4 |
| S. aureus BX1633-2 at $10^{-2}$ dil'n | A9606 | 500 | 8 |
| S. aureus meth.-resist; at $10^{-3}$ dil'n | A15097 | >500 | 32 |
| Sal. enteritidis= | A9531 | 32 | 4 |
| E. coli Juhl= | A14119 | 125 | 8 |
| E. coli= | A9675 | 250 | 16 |
| K. pneumoniae= | A9977 | 63 | 4 |
| K. pneumoniae= | A15130 | 125 | 16 |
| Pr. mirabilis= | A9900 | 125 | 4 |
| Pr. morganii= | A15153 | >500 | >125 |
| Ps. aeruginosa= | A9843A | >500 | >125 |
| Ser. marcescens= | A20019 | >500 | >125 |
| Ent. cloacae | A9656 | — | — |
| Ent. cloacae | A9657 | — | — |
| Ent. cloacae | A9659 | — | — |

*50% Nutrient Broth - 45% Antibiotic Assay Broth
=at $10^{-4}$ dilution.

EXAMPLE 22

7β-(D-α-aminophenylacetamido)-3-benzyl-Δ³-0-2-isocephem-4-carboxylic acid

If the procedure of Example 21 is repeated by replacing the benzyl 7β-amino-Δ³-0-2-isocephem-4-carboxylate used therein by an equimolar weight of benzyl 7β-amino-3-benzyl-Δ³-0-2-isocephem-4-carboxylate, the title product is obtained.

EXAMPLE 23

7β-(D-α-aminophenylacetamido)-3-phenethyl-Δ³-0-2-isocephem-4-carboxylic acid

If the procedure of Example 21 is repeated by replacing the benzyl 7β-amino-Δ³-0-2-isocephem-4-carboxylate used therein by an equimolar weight of benzyl 7β-amino-3-phenethyl-Δ³-0-2-isocephem-4-carboxylate, the title product is obtained.

EXAMPLE 24

7β-(2-Aminomethylphenylacetamido)-3-methyl-Δ³-0-2-isocephem-4-carboxylic acid

To a suspension of 1.2 g. (0.038 mole) of potassium 2-(1-carbomethoxypropen-2-ylaminomethyl)phenylacetate in 23 ml. of tetrahydrofuran was added 3 drops of dimethylbenzylamine. The mixture was cooled in a dry ice bath to −40° and 520 mg. (0.038 mole) of isobutyl chloroformate was added all at once. The mixture was stirred for 5 minutes and added to a cooled (3°) solution of 500 mg. of 7-amino-3-methyl-Δ³-0-2-isocephem-4-carboxylic acid and 0.71 ml. of N-methylmorpholine in 13 ml. of water. The solution was stirred in an ice-bath for 1 hour at 0°, then concentrated hydrochloric acid was added dropwise to pH 5.2. The tetrahydrofuran was removed at 30° (15 mm) and the aqueous solution was layered with ethyl acetate. The mixture was stirred at 25° for 1 hour and the crystals were collected, washed with water and dried over $P_2O_5$ to constant weight to give 85 mg; mp > 150° slow decomposition. The NMR and IR spectra were consistent for the structure.

Anal. Calc'd. for $C_{17}H_{19}N_3O_5.H_2O$: C, 56.19; H, 5.82; N, 11.56. Found: C, 56.00; H, 5.68; N, 11.32.

EXAMPLE 25

7β-(α-Benzoylureidophenylacetamido)-3-methyl-Δ³-0-2-isocephem-4-carboxylic acid 972 mg. (0.003 moles) of benzyl 7β-amino-3-methyl-Δ³-0-2-isocephem-4-carboxylate hydrochloride was partially dissolved in 40 ml. of dry methylene chloride and 302 mg. (0.003 moles) of N-methylmorpholine. To this was added 892 mg. (0.003 moles) of α-benzoylureidophenylacetic acid and 760 mg. (0.003 moles) of EEDQ. The slurry was stirred for 30 minutes at room temperature. Not all went in solution and 12 ml. of N,N-dimethylformamide was added. A cloudy solution resulted which turned clear after stirring for 30 minutes. The yellow solution was stirred for 2½ hours and was then concentrated to an oil, which was redissolved in 80 ml. of ethyl acetate and extracted with 80 ml. of 5% aqueous sodium bicarbonate and 80 ml. of 5% hydrochloric acid. The ethyl acetate phase was dried over magnesium sulfate, filtered and concentrated to dryness. The resulting foam was triturated with ether and the resulting tan solid was removed by filtration and dried in vacuo. Wt = 700 mg. Infrared spectrum and NMR spectrum indicated the solid to be benzyl 7β-(α-benzoylureidophenylacetamido)-3-methyl-Δ³-0-2-isocephem-4-carboxylate. This was dissolved in 95 ml. of 100% ethanol and 5 ml. of water at 39°. 700 mg. of 30% palladium on Celite was added. It was reduced at 50 lbs./sq. inch in a Parr hydrogenation apparatus for 30 minutes. The catalyst was removed by filtration through Celite and it was washed with 100 ml. of 100% ethanol. The combined filtrates were concentrated to an oil which was solidified by slurrying it in ether. A tan solid resulted. It was removed by filtration and dried in high vacuum. Wt = 250 mg. Infrared spectrum and NMR spectrum were consistent with the desired material.

Anal. Cald'd. $C_{24}H_{22}N_4O_7.4H_2O$: C, 52.60; H, 5.51; N, 10.20. Found: C, 52.45; H, 4.26; N, 10.22.

EXAMPLE 26

7β-(2,6-Dimethoxybenzamido)-3-methyl-Δ³-0-2-isocephem-4-carboxylic acid 729 mg. (0.00225 moles) of benzyl 7-amino-3-methyl-Δ³-0-2-isocephem-4-carboxylate hydrochloride was dissolved in 15 ml. of acetonitrile and 453 mg. (0.0045 moles) of N-methylmorpholine. To this was added 420 mg. (0.00225 moles) of 2,6-dimethoxybenzoyl chloride. The yellow solution was stirred for 2 hours at room temperature. A thin layer chromatogram was taken at that point and it had one major spot at Rf 0.6 indicating product. The reaction mixture was concentrated to dryness, taken up in ethyl acetate and extracted with 30 ml. of 5% aqueous sodium bicarbonate and 30 ml. of 5% hydrochloric acid. The ethylacetate phase was dried over magnesium sulfate, filtered and concentrated to a yellow foam. It was solidified with ether, filtered and dried in high vacuum for 15 hours. A tan solid resulted, wt = 500 mg. Infrared spectrum and NMR spectrum indicated it to be the desired benzyl 7β-(2,6-dimethoxybenzamido)-3-methyl-Δ³-0-2-isocephem-4-carboxylate. This was dissolved in 100 ml. of 100% ethanol at 40°. A 90% solution resulted. To this was added 500 mg. of 30% palladium on Celite. It was reduced at 50 lbs./sq. inch in a Parr hydrogenation apparatus for 40 minutes. The reaction mixture was heated to 40° and the catalyst was removed by filtration through Celite. It was washed twice with 100 ml. of 100% ethanol and the combined filtrates were concentrated to a greyish solid, which was washed with ether, filtered and dried in vacuo, wt = 350 mg. Infrared spectrum and NMR spectrum were consistent with the desired material.

Anal. Calc'd. for $C_{17}H_{18}N_2O_7 \cdot H_2O$: C, 53.85; H, 5.27; N, 7.38. Found: C, 54.77; H, 5.15; N, 7.19.

EXAMPLE 27

7β-(D-α-Hydroxyphenylacetamido)-3-methyl-Δ³-0-2-isocephem-4-carboxylic acid

Benzyl 7β-amino-3-methyl-Δ³-0-2-isocephem-4-carboxylate hydrochloride (972 mg., 0.003 moles) was dissolved in 20 ml. of dry methylene chloride and 302 mg. (0.003 moles) of N-methylmorpholine. To this was added 536 mg. (0.003 moles) of D-anhydro-o-carboxymandelic acid. The yellow solution was stirred for 2 hours at room temperature. Then the reaction mixture was extracted with 20 ml. of 5% aqueous sodium bicarbonate and 20 ml. of 5% hydrochloric acid. The methylene chloride phase was dried over magnesium sulfate, filtered and concentrated to an oil. It was triturated with ether. A yellow foam resulted, wt = 550 mg. Infrared spectrum and NMR spectrum indicated this to be desired benzyl 7β-(D-α-hydroxyphenylacetamido)-3-methyl-Δ³-0-2-isocephem-4-carboxylate. This was dissolved in 100 ml. of 100% ethanol and 550 mg. of 30% palladium on Celite was added. It was reduced at 50 lbs./sq. inch in a Parr hydrogenation apparatus for 30 minutes. The catalyst was removed by filtration through Celite and was washed twice with 100 ml. of 100% ethanol. The combined filtrates were concentrated to a greyish solid, which was washed with ether, filtered and dried in vacuo, wt = 420 mg. Infrared spectrum and NMR spectrum were consistent with the desired material.

Anal. Calc'd. for $C_{16}H_{16}N_2O_6 \cdot C_2H_5OH$: C, 57.06; H, 5.69; N, 7.41, Found: C, 57.06; H, 5.15; N, 6.93.

EXAMPLE 28

7β-[N-(Phenylacetimidoyl)aminoacetamido]-3-methyl-Δ³-0-2-isocephem-4-carboxylic acid Method 1:

Benzyl 7β-amino-3-methyl-Δ³-0-2-isocephem-4-carboxylate hydrochloride (243 mg., 0.00075 moles) was dissolved in 10 ml. of dry methylene chloride and 75 mg. (0.00075 moles) of N-methylmorpholine. To this was added 170 mg. (0.00075 moles) of 3-benzyl-1,2,4-oxadiazole-5-one-4-acetic acid and 190 mg. (0.00075 moles) of EEDQ. It was stirred for 2 hours at room temperature and then concentrated to an orange-brown foam. It was taken up in 2 ml. of ethyl acetate and extracted with 20 ml. of 5% aqueous sodium bicarbonate and 2 ml. of 5% hydrochloride acid. The ethyl acetate phase was dried over magnesium sulfate, filtered and concentrated to a brown oil, wt = 100 mg. Infrared spectrum and NMR spectrum indicated the desired benzyl 7β-(3-benzyl-1,2,4-oxadiazole-5-one-4-acetamido)-3-methyl-Δ³-0-2-isocephem-4-carboxylate.

Method 2:

3-Benzyl-1,2,4-oxadiazole-5-one-4-acetic acid (1.0 g., 0.00427 moles) was slurried in 12.5 ml. of dry methylene chloride and hydrogen chloride gas was bubbled into the reaction mixture for 2 minutes with cooling. The insoluble material was filtered off and 1.15 g. (0.00553 moles) of phosphorus pentachloride was added to the filtrate in small portions. All went in solution. It was stirred for 15 hours at room temperature. The reaction mixture was concentrated to dryness and the crystalline residue was triturated with cyclohexane, filtered and dried in high-vacuum for 30 minutes. Infrared spectrum indicated this to be desired 3-benzyl-1,2,4-oxadiazole-5-one-4-acetyl chloride. In the meantime, 243 mg. (0.00075 moles) of benzyl 7β-amino-3-methyl-Δ³-0-2-isocephem-4-carboxylate hydrochloride was dissolved in 10 ml. of dry methylene chloride and 151 mg. (0.0015 moles) of N-methylmorpholine. To this was added 188 mg. (0.00075 moles) of 3-benzyl-1,2,4-oxadiazole-5-one-4-acetyl chloride. The slightly yellow solution was stirred for 2 hours at room temperature. Then it was extracted with 10 ml. of 5% sodium bicarbonate. 10 ml. of 5% hydrochloric acid and 10 ml. saturated sodium chloride solution. The methylene chloride phase was dried over magnesium sulfate, filtered, and concentrated to a yellow foam, wt = 130 mg. Infrared spectrum and NMR spectrum indicated this to be desired benzyl 7β-(3-benzyl-1,2,4-oxadiazole-5-one-4-acetamido)-3-methyl-Δ³-0-2-isocephem-4-carboxylate.

Benzyl 7β-(3-benzyl-1,2,4-oxadiazole-5-one-4-acetamido)-3-methyl-Δ³-0-2-isocephem-4-carboxylate (200 mg.) was dissolved in 100 ml. of 100% ethanol and 10 ml. of water at 40°. To this was added 200 mg. of 30% palladium on Celite. It was hydrogenated in a Parr hydrogenation apparatus at 30 lbs./sq. inch for 40 minutes. The catalyst was removed by filtration through Celite and wash washed thoroughly with 100 ml. of 100% ethanol. The combined filtrates were concentrated to a brown oil, which was solidified with ether, filtered and dried in high vacuum. A brownish solid resulted, wt = 100 mg. Infrared spectrum and NMR spectrum were consistent with the desired material.

Anal. Calc'd. for $C_{18}H_{20}N_4O_5 \cdot H_2O$: C, 55.60; H, 5.70; N, 14.38. Found: C, 55.45; H, 5.63; N, 14.18.

EXAMPLE 29

7β-Valeramido-3-methyl-Δ³-0-2-isocephem-4-carboxylic acid

Benzyl 7β-amino-3-methyl-Δ³-0-2-isocephem-4-carboxylate hydrochloride (1.21 g., 0.00375 moles) was dissolved in 25 ml. of dry methylene chloride and 375 mg. (0.00375 moles) of N-methylmorpholine. To this was added 380 mg. (0.00375 moles) of valeric acid and 950 mg. (0.00375 moles) of EEDQ. The slightly yellow solution was stirred for 2 hours at room temperature. Then the reaction mixture was washed with 50 ml. of 5% aqueous sodium bicarbonate and 50 ml. of 5% hydrochloric acid. The methylene chloride phase was dried over magnesium sulfate, filtered and concentrated to a yellow oil, which was washed with ether and dried in high vacuum. A yellow oil resulted, wt = 602 mg. Infrared spectrum and NMR spectrum indicated this to be the desired benzyl 7β-valeramido-3-methyl-Δ³-0-2-isocephem-4-carboxylate. This was dissolved in 100 ml. of 100% ethanol and 600 mg. of 30% palladium on Celite was added. This was reduced at 40 lbs./sq. inch in a Parr hydrogenation apparatus for 35 minutes. The catalyst was removed by filtration through Celite and washed thoroughly with 100 ml. of 100% ethanol. The combined filtrates were concentrated to a brown oil, which was solidified by washing with ether. A tan solid resulted. It was removed by filtration and dried in vacuo for 15 hours, wt = 310 mg. Infrared spectrum and NMR spectrum were consistent with the desired material.

Anal. Calc'd. for $C_{13}H_{18}N_2O_5$: C, 55.50; H, 6.44; N, 9.96. Found: C, 55.39; H, 6.06; N, 9.07.

EXAMPLE 30

Replacement of the 7β-amino-3-methyl-Δ³-0-2-isocephem-4-carboxylic free acid, benzyl ester, or hydrochloride salt of Examples 24–29 with an equimolar weight of the free acid, benzyl ester or hydrochloride salt of 7β-amino-Δ³-0-2-isocephem-4-carboxylic acid, 7β-amino-3-benzyl-Δ³-0-2-isocephem-4-carboxylic acid and 7β-amino-3-phenethyl-Δ³-0-2-isocephem-4-carboxylic acid, respectively, produces 7β-(2-aminomethylphenylacetamido)-Δ³-0-2-isocephem-4-carboxylic acid, 7β-(2-aminomethylphenylacetamido)-3-benzyl-Δ³-0-2-isocephem-4-carboxylic acid, 7β-(2-aminomethylphenylacetamido)-3-phenethyl-Δ³-0-2-isocephem-4-carboxylic acid, 7β-(α-benzoylureidophenylacetamido)-Δ³-0-2-isocephem-4-carboxylic acid, 7β-(α-benzoylureidophenylacetamido)-3-benzyl-Δ³-0-2-isocephem-4-carboxylic acid, 7β-(α-benzoylureidophenylacetamido)-3-phenethyl-Δ³-0-2-isocephem-4-carboxylic acid, 7β-(2,6-dimethoxybenzamido)-Δ³-0-2-isocephem-4-carboxylic acid, 7β-(2,6-dimethoxybenzamido)-3-benzyl-Δ³-0-2-isocephem-4-carboxylic acid, 7β-(2,6-dimethoxybenzamido)-3-phenethyl-Δ³-0-2-isocephem-4-carboxylic acid, 7β-(D-α-hydroxyphenylacetamido)-Δ³-0-2-isocephem-4-carboxylic acid, 7β-(D-α-hydroxyphenylacetamido)-3-benzyl-Δ³-0-2-isocephem-4-carboxylic acid, 7β-(D-α-hydroxyphenylacetamido)-3-phenethyl-Δ³-0-2-isocephem-4-carboxylic acid, 7β-[N-(phenylacetimidoyl)aminoacetamido]-Δ³-0-2-isocephem-4-carboxylic acid, 7β-[N-(phenylacetamidoyl)aminoacetamido]-3-benzyl-Δ³-0-2-isocephem-4-carboxylic acid, 7β-[N-(phenylacetamidoyl)aminoacetamido]-3-phenethyl-Δ³-0-2-isocephem-4-carboxylic acid, 7β-valeramido-Δ³-0-2-isocephem-4-carboxylic acid, 7β-valeramido-3-benzyl-Δ³-0-2-isocephem-4-carboxylic acid, 7β-valeramido-3-phenethyl-Δ³-0-2-isocephem-4-carboxylic acid, respectively.

EXAMPLE 31

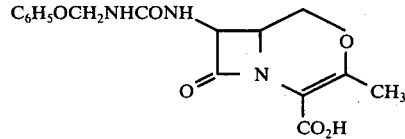

A mixture of benzyl 7β-amino-3-methyl-Δ³-0-2-isocephem-4-carboxylate (1.44 g.; 5 mmole) and phenoxyacetylazide[1] (1.0 g.; 5.5 mmole) in benzene (100 ml.) was refluxed for 24 hours. After being kept at room temperature for 3 days, some white crystals separated and were collected by suction filtration; 0.30 g. white solid m.p. 195°–196° with decomposition was obtained. The filtrate was washed with 10% HCl, water and brine and then dried ($Na_2SO_4$) and evaporated to give 1.73 g.

of a brown oil. Spectral data were in accordance with the structure

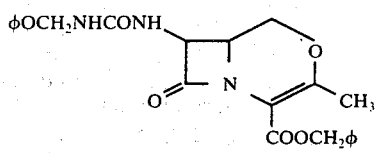

1. Joseph Weinstock, J. Org. Chem. 26, 3511(1961).

A solution of the above isocephem compound (1.73 g.; 4.0 mmole) in absolute alcohol (25 ml.) and tetrahydrofuran (10 ml.) was added to 10% Pd on C (1.7 g.) and stirred under hydrogen at atmospheric pressure for 2 hours. The solution was filtered from the catalyst through celite and evaporated to give 1.03 g. oil. This was partitioned between ether and saturated $NaHCO_3$. The aqueous phase was separated, acidified with cold 10% HCl, and extracted with $CH_2Cl_2$. The $CH_2Cl_2$ extract was washed with water, and brine, dried ($Na_2SO_4$) and evaporated to give 0.20 g. brown semi-solid. This was crystallized in benzene/petroleum ether (30–60) and gave a light yellow shiny solid identified by spectral analysis as the compound of the formula

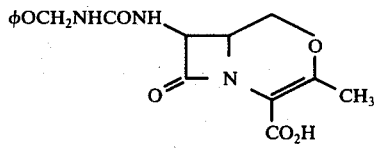

M.P. 177°–182° with decomposition.

Anal Calc'd. for $C_{16}H_{17}N_3O_6$. 1/4 $H_2O$: C, 54.62; H, 5.01; N, 11.94. Found: C, 54.59; H, 4.96; N, 11.46.

M.I.C. data for the above product (called (BC-L24) is shown in Table 9 on page 336.

EXAMPLE 32

7β-Phenylacetamido-3-methyl-Δ³-0-2-isocephem-4-carboxylic acid

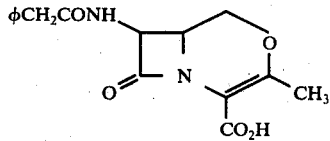

A mixture of benzyl 7β-amino-3-methyl-Δ³-0-2-isocephem-4-carboxylate (2.1 g.; 7.3 mmole), phenylacetic acid (1.0 g.; 7.3 mmole) and EEDQ (1.8 g.; 7.3 mmole) in 50 ml. $CH_2Cl_2$ was stirred at room temperature for 2 hours, then washed successively with 1% $NaHCO_3$, 10% HCl and brine. It was dried ($Na_2SO_4$) and evaporated to give 2.95 g. of a thick syrup identified as benzyl 7β-phenylacetamido-3-methyl-Δ³-0-2-isocephem-4-carboxylate. This ester was used as such with no further purification.

A mixture of the above benzyl ester (0.50 g.; 1.2 mmole) and 10% Pd on C (0.50 g.) in THF (20 ml.) was hydrogenated at atmospheric pressure and after 10 minutes, uptake of hydrogen was complete. If was filtered (washed well with $CH_2Cl_2$) and evaporated to give 0.29 g. of a solid. This was recrystallized from acetone/ether to give a white solid, m.p. 197°–198° with decomposition, which was identified by IR and NMR as the title product.

Anal Calc'd. for $C_{16}H_{16}N_2O_5 \cdot 1.5H_2O$: C, 55.97; H, 5.57; N, 7.15. Found: C, 55.83; H, 5.85; N, 7.17.

M.I.C. data for the above product (called BC-L30) is shown in Table 9.

EXAMPLE 33

7β-(2-Thienylacetamido)-3-methyl-Δ³-0-2-isocephem-4-carboxylic acid

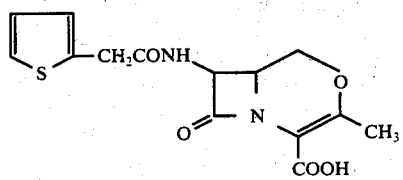

Benzyl 7β-azido-3-methyl-Δ³-0-2-isocephem-4-carboxylate (314 mg.; 1 mmole) in 50 ml. of absolute ethanol was hydrogenated at 40 psi of hydrogen in the presence of palladium chloride (100 mg.) for 1 hour. The palladium black was filtered off and the solvent was removed on a flash evaporator leaving a crude hydrochloride salt of 7β-amino-3-methyl-Δ³-0-2-isocephem-4-carboxylic acid (234 mg.).

This crude hydrochloride salt was dissolved in 5 ml. of water and cooled to 0° C. in ice bath. Sodium bicarbonate (500 mg.; 6 mmole) was added followed by 2-thienyl acetyl chloride (320 mg.; 2 mmole) in 2 ml. of acetone. The mixture was stirred for 1 hour and then extracted twice with diethylether (10 ml. portions). The aqueous layer was acidified with hydrochloric acid (aqueous 10%) and extracted 3 times with chloroform (10 ml. portions). The combined chloroform extracts were concentrated to a residual oil on an evaporator. A solid was obtained upon trituration with diethylether and was recrystallized from ethanol to give 160 mg. (50%) of the title product; m.p. 213° C. (corrected).

U.V. $\lambda_{max}^{EtOH} = 270$; $\epsilon = 9187$

Anal. Calc'd. for $C_{14}H_{14}N_2O_5S$: C, 52.17; H, 4.38; N, 8.69; S, 9.95. Found: C, 51.89; H, 4.59; N, 8.61; S, 9.78.

M.I.C. data for the above product (called BC-L55) is shown in Table 9.

EXAMPLE 34

7β-[α-carboxy-α-phenylacetamido]-3-methyl-Δ³-0-2-isocephem-4-carboxylic acid

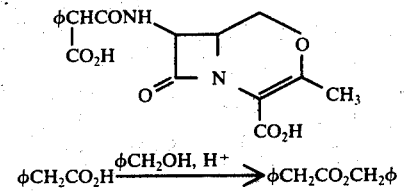

A solution of phenyl acetic acid (27.2 g.), benzyl alcohol (21.6 g.) and p-toluenesulfonic acid (380 mg.) in 100 ml. of toluene was heated under reflux under a Dean-Stark trap until the theoretical (3.6 ml.) quantity of water had been collected. On cooling, the solution was washed with dilute $NaHCO_3$ and saturated NaCl and solvent was removed in vacuo.. The resulting oil was distilled at 125°-129° (0.4 torr)[1] to give pure benzyl phenylacetate, 37.7 g. (83% yield).

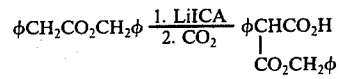

A solution of 20.8 ml. of 2.4 M n-butyl lithium in hexane was added to a solution of i-propylcyclohexylamine (7.06 g.) in 35 ml. of tetrahydrofuran at −78°. After 10 minutes, a solution of phenylacetic acid benzyl ester (11.3 g.) in 55 ml. of tetrahydrofuran was added over 10 minutes. After 5 minutes, carbon dioxide was bubbled into the solution until the yellow color faded. After warming to 0°, dilute sodium carbonate and ether were added until all the solid returned to solution. The aqueous layer was separated and the organic layer extracted with more dilute sodium carbonate. The combined aqueous layers were washed with ether, cooled to 0° and acidified with cold 3N hydrochloric acid. The aqueous was extracted with ether (2 × 100 ml.) and the ether washed with saturated sodium chloride, dried (sodium sulfate) and evaporated in vacuo to give the desired acid as an oil, 7.8 g., 58% yield. The acid has been reported in the literature: Chem. Abs. 63, 13269 g (1965).

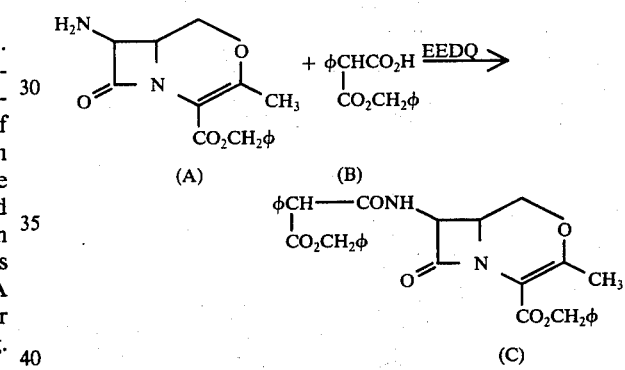

A solution of one millimole each of A, B and EEDQ in 8 ml. of methylene chloride was maintained at 24° for 16 hours. The resulting solution was washed with 2% sodium bicarbonate (8 ml.), 10% hydrochloric acid (2 × 8 ml.) and saturated sodium chloride (8 ml.), then dried (sodium sulfate) and absorbed onto 2 g. of grade III silica gel.

The crude product, absorbed onto silica gel, was washed with methylene chloride (10 ml.), then extracted from the silica gel with ethyl acetate (100 ml.). The extracts were absorbed onto 1.7 g. of silica gel and placed on an 11 g. column of silica gel (grade III). Elution with ether/hexane 75:25 gave pure (C) as the major fraction (30% yield). Recrystallization from ether/methylene chloride gave material with m.p. 152°-157° (with decomposition).

Anal. Calc'd. for $C_{31}H_{28}N_2O_7$: C, 68.88; H, 5.22; N, 5.18. Found: C, 68.50; H, 5.38; N, 5.19.

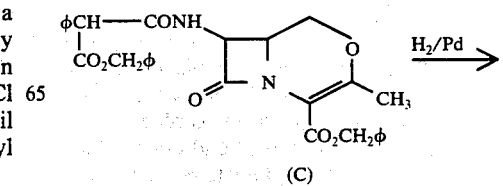

-continued

φ—CH—CONH  
|  
$CO_2H$ (structure with β-lactam fused to oxazine ring with CH₃ and COOH)

(D)

To a solution of (C) (200 mg.) in 10 ml. of ethanol plus 10 ml. of ethyl acetate was added 100 mg. of 30% palladium on diatomaceous earth. The resulting mixture was hydrogenated at atmospheric pressure and 24° until uptake of hydrogen ceased. The catalyst was removed by filtration and the solvent evaporated to give the title product (D) in quantitative yield. Attempts to crystallize the crude product led to loss of purity.

U.V. $\lambda_{max}^{MeOH}$ 269 ($\epsilon$ = 8800)

Anal Calc'd. for $C_{17}H_{16}N_2O_7 \cdot C_2H_6O \cdot 1/2H_2O$: C, 54.94; H, 5.38; N, 6.74. Found: C, 54.90; H, 5.28; N, 6.91.

M.I.C. data for the above product (called BC-L48) is shown in Table 9.

EXAMPLE 35

7β-(o-Hydroxyphenylacetamido)-3-methyl-Δ³-0-2-isocephem-4-carboxylic acid (structure: o-hydroxyphenyl-CH₂CONH- attached to isocephem with CH₃ and $CO_2H$)

The acylation procedure of Example 34 was repeated with the acylating acid used therein replaced by an equimolar weight of o-hydroxyphenylacetic acid. The crude acylation product, absorbed onto silica gel, was placed on a column of silica gel (grade III, 8 g.). Elution with ether gave, as the major fraction, benzyl 7β-(o-hydroxyphenylacetamido)-3-methyl-Δ³-0-2-isocephem-4-carboxylate, in 26.5% yield. The benzyl ester was hydrogenated as in Example 34 to give the title product.

U.V. $\lambda_{max}^{MeOH}$ 274 ($\epsilon$ = 7200).

Anal. Calc'd. for $C_{16}H_{16}N_2O_6 \cdot 1/4H_2O$: C, 57.06; H, 4.94; N, 8.32. Found: C, 56.92; H, 5.03; N, 8.33.

M.I.C. data for the above product (called BC-L49) is shown in Table 9.

EXAMPLE 36

7β-[Cyanoacetamido]-3-methyl-Δ³-0-2-isocephem-4-carboxylic acid

N≡CCH₂CONH- (structure of isocephem with CH₃ and $CO_2H$)

The acylation procedure of Example 34 was repeated with the acylating acid used therein replaced by an equimolar weight of cyanoacetic acid. The crude acylation product, absorbed onto silica gel, was placed on a column of silica gel (grade III, 3.5 g.) and eluted with ether, methylene chloride and ethyl acetate. The methylene chloride and ethyl acetate fractions were combined and triturated with chloroform several times to give benzyl 7β-(cyanoacetamido)-3-methyl-Δ³-0-2-isocephem-4-carboxylate in 31% yield. The benzyl ester was hydrogenated as in Example 34 to give the title product.

U.V. $\lambda_{max}^{MeOH}$ 269 ($\epsilon$ = 6400)

Anal. Cal'd. for $C_{11}H_{11}N_3O_5 \cdot 1/4H_2O$: C, 48.98; H, 4.30; N, 15.58. Found: C, 49.34; H, 4.42; N, 15.41.

M.I.C. data for the above product (called BC-L50) is shown in Table 9.

If the procedure of Example 36 is repeated using α-cyanopropionic acid in place of the cyanoacetic acid used therein, there is obtained 7β-(α-cyanopropionamido)-3-methyl-Δ³-0-2-isocephem-4-carboxylic acid.

EXAMPLE 37

7β-[2-(2H)-tetrazolylacetamido]-3-methyl-Δ³-0-2-isocephem-4-carboxylic acid (tetrazole-CH₂CONH- attached to isocephem with CH₃ and $CO_2H$)

(Reaction scheme:) 
2H-tetrazolyl-CH₂CO₂Et $\xrightarrow{\text{1. KOH}}_{\text{2. H}^+}$ 2H-tetrazolyl-CH₂CO₂H · H₂O A solution of potassium hydroxide (4.5 g.) in 70 ml. of absolute ethanol was added to a solution of the above ethyl ester [1] (5.0 g.) in 25 ml. of absolute ethanol. After heating under reflux for 30 minutes, the solution was evaporated to dryness in vacuo. The residue was dissolved in 50 ml. water and a slurry (52 ml.) of ion exchange resin (Dowex 50W-X4-acid form) was added. After brief stirring, the resin was filtered off, the solution treated with charcoal, filtered and evaporated in vacuo to give the acid indicated above as a crystalline solid, 3.68 g. (79% yield); m.p. 156°-158° C. (With decomposition).

1. W. G. Finnegan, R. A. Henry, R. Lofquist, J. Am. Chem Soc. 80, 3908 (1958)

The acylation procedure of Example 34 was repeated with the acylating acid used therein replaced by an equimolar weight of 2-(2H)-tetrazoleacetic acid and acetonitrile used as the solvent. The crude acylation product was crystallized from ethyl acetate to give pure benzyl 7β-[2-(2H)-tetrazolylacetamido]-3-methyl-Δ³-0-2-isocephem-4-carboxylate in 48% yield; m.p. 169°-170° (with decomposition).

Anal. Calc'd. for $C_{18}H_{18}N_6O_5$: C, 54.28; H, 4.55; N, 21.10. Found: C, 54.37; H, 4.75; N, 20.48.

The mother liquors from the crystallization of the above benzyl ester were placed on a 3.5 g. silica gel (grade III column. Elution with ether/ethyl acetate gave benzyl 7β-(ethoxycarboxamido)-3-methyl-Δ³-0-2-isocephem-4-carboxylate in 21.5% yield which was used in the following example.

The benzyl 7β-[2-(2H)-tetrazolylacetamido]-3-methyl-Δ³-0-2-isocephem-4-carboxylate was hydrogenated as in Example 34 to give the title product;

U.V. $\lambda_{max}^{MeOH}$ 270 ($\epsilon$ = 9200).

Anal. Calc'd for $C_{11}H_{12}N_6O_5 \cdot C_2H_6O \cdot 1/2H_2O$: C, 42.97; H, 5.27; N, 23.13. Found: C, 42.99; H, 4.58; N, 23.08.

M.I.C. data for the above product (called BC-L51) is shown in Table 9.

EXAMPLE 38

7β-(Ethoxycarboxamido)-3-methyl-Δ³-0-2-isocephem-4-carboxylic acid

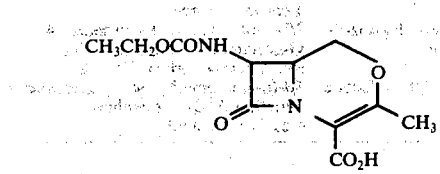

Benzyl 7β-(ethoxycarboxamido)-3-methyl-Δ³-0-2-isocephem-4-carboxylate (as produced in Example 37) was hydrogenated as in Example 34 to give the title product.

U.V. $\lambda_{max}^{MeOH}$ 269 (ε = 7600).

Anal Calc'd. for $C_{11}H_{14}N_2O_6 \cdot 1/4C_2H_6O \cdot 1/4H_2O$: C, 48.25; H, 5.63; N, 9.79. Found: C, 47.95; H, 5.12; N, 9.92.

M.I.C. data for the above product (called BC-L52) is shown in Table 9.

EXAMPLE 39

7β-[3-(o-chlorophenyl)-5-methyl-isoxazol-4-ylcarboxamido]-3-methyl-Δ³-0-2-isocephem-4-carboxylic acid

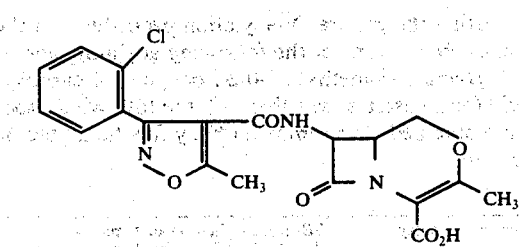

To a solution of 1.0 mmole of benzyl 7β-amino-3-methyl-Δ³-0-2-isocephem-4-carboxylic acid and 1.10 ml. triethylamine in 5 ml. methylene chloride was added a solution of 1.10 mmole of 3-(o-chlorophenyl)-5-methyl-4-isoxazole-carboxylic acid chloride in 5 ml. methylene chloride. After 18 hours at 24° C., the solution was diluted with 50 ml. methylene chloride and washed with 50 ml. each of saturated NaCl, 10% HCl, saturated $NaNCO_3$ and saturated NaCl. The methylene chloride solution was dried (sodium sulfate) and evaporated in vacuo to a brown solid which was triturated with ether.

The solid crude acylation product was dissolved in methylene chloride and absorbed onto 25 g. silica gel (grade III). The silica gel was eluted with methylene chloride, then ethyl acetate. The ethyl acetate extract was triturated with ether to give benzyl 7β-[3-(o-chlorophenyl)-5-methylisoxazol-4-yl-carboxamido]-3-methyl-Δ³-0-2-isocephem-4-carboxylate in 80.5% yield; m.p. 100°-110° C (with decomposition). Hydrogenation of the benzyl ester according to the procedure of Example 34 gave the title product.

U.V. $\lambda_{max}^{MeOH}$ 271 (ε = 9600).

Anal Calc'd for $C_{19}H_{16}ClN_3O_6 \cdot C_2H_2O \cdot H_2O$: C, 52.34; H, 5.02; N, 8.72; Cl, 7.36 Found: C, 51.81; H, 4.54; N, 9.37; Cl, 7.15.

Residue: 1.95%.

M.I.C. data for the above product (called BC-L59) is shown in Table 9.

EXAMPLE 40

7β-[1-(1H)-Tetrazolylacetamido]-3-methyl-Δ³-0-2-isocephem-4-carboxylic acid

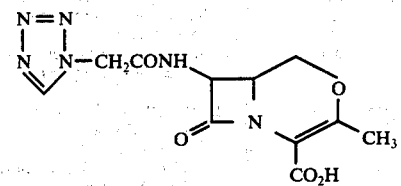

1-(1H)-Tetrazolylacetic acid (256 mg.), 6.25 ml. of benzene and 1.25 ml. oxalyl chloride were stirred at 24° for 3 days. The starting acid was filtered off and evaporation of the solution gave 1-(1H)-tetrazoleacetyl chloride in 58% yield.

The acylation procedure of Example 39 was repeated with the acylating acid chloride used therein replaced by an equimolar weight of 1-(1H)-tetrazoleacetyl chloride. The solid acylation product, i.e. benzyl 7β-[1-(1H)-tetrazolylacetamido]-3-methyl-Δ³-0-2-isocephem-4-carboxylate, was obtained in 22.5% yield.

Hydrogenation of the benzyl ester according to the procedure of Example 34 gives the title product.

EXAMPLE 41

Replacement of the 7β-amino-3-methyl-Δ³-0-2-isocephem-4-carboxylic acid of Examples 31-40 with an equimolar weight of 7β-amino-Δ³-0-2-isocephem-4-carboxylic acid, 7β-amino-3-benzyl-Δ³-0-2-isocephem-4-carboxylic acid or 7β-amino-3-phenethyl-Δ³-0-2-isocephem-4-carboxylic acid, respectively, produces the corresponding 7β-acylamido-Δ³-0-2-isocephem-4-carboxylic acids, 7β-acylamido-3-benzyl-Δ³-0-2-isocephem-4-carboxylic acids and 7β-acylamido-3-phenethyl-Δ³-0-2-isocephem-4-carboxylic acids, respectively.

EXAMPLE 42

Repeating the general N-acylation procedures of the examples above to react the following acylating agents with 7β-amino-3-methyl-Δ³-0-2-isocephem-4-carboxylic acid (or an ester or salt thereof), the following products are obtained after removal of any functional blocking groups.

| | |
|---|---|
| 4-nitrophenylacetyl chloride | 7β-(4-mitrophenylacetamido)-3-methyl-Δ³-0-2-isocephem-4-carboxylic acid |
| p-fluorophenylacetyl chloride | 7β-(p-fluorophenylacetamido)-3-methyl-Δ³0-2-isocephem-4-carboxylic acid |
| p-acetoxyphenylacetyl chloride | 7β-(p-acetoxyphenylacetamido)-3-methyl-Δ³-0-2-isocephem-4-carboxylic acid |
| o-chlorophenylacetyl chloride | 7β-(o-chlorophenylacetamido)-3-methyl-Δ³-0-2-isocephem-4-carboxylic acid |
| 3-thienylacetyl chloride | 7β-(3-thienylacetamido)-3-methyl-Δ³-0-2-isocephem-4-carboxylic acid |
| p-aminophenylacetyl chloride | 7β-(p-aminophenylacetamido)-3-methyl-Δ³-0-2-isocephem-4-carboxylic acid |
| p-methylphenylacetyl chloride | 7β-(p-methylphenylacetamido)-3-methyl-Δ³-0-2-isocephem-4-carboxylic acid |
| 4-guanidinophenylacetyl chloride hydrochloride | 7β-(4-guanidinophenylacetamido)-3-methyl-Δ³0-2-isocephem- |

| | |
|---|---|
| 4-isopropylphenylacetyl chloride | 7β-(4-isopropylphenylacetamido)-3-methyl-Δ³-0-2-isocephem-4-carboxylic acid |
| 4-methylthiophenylacetyl chloride | 7β-(4-methylthiophenylacetamido)-3-methyl-Δ³-0-2-isocephem-4-carboxylic acid |
| 4-cyanophenylacetyl chloride | 7β-(4-cyanophenylacetamido)-3-methyl-Δ³-0-2-isocephem-4-carboxylic acid |
| 4-methoxyphenylacetyl chloride | 7β-(4-methoxyphenylacetamido)-3-methyl-Δ³-0-2-isocephem-4-carboxylic acid |
| 2,6-dimethoxyphenylacetyl chloride | 7β-(2,6-dimethoxyphenylacetamido)-3-methyl-Δ³-0-2-isocephem-4-carboxylic acid |
| 3-sulfamylphenylacetyl chloride | 7β-(3-sulfamylphenylacetamido)-3-methyl-Δ³-0-2-isocephem-4-carboxylic acid |
| 2-methyl-4-chlorphenyl-acetyl chloride | 7β-(2-methyl-4-chlorophenyl-acetamido)-3-methyl-Δ³-0-2-isocephem-4-carboxylic acid |
| syndnone-3-acetyl chloride | 7β-(sydnone-3-acetamido)-3-methyl-Δ³-0-2-isocephem-4-carboxylic acid |
| syndnone-4-acetyl chloride | 7β-(syndone-4-acetamido)-3-methyl-Δ³-0-2-isocephem-4-carboxylic acid |
| 2-furylacetyl chloride | 7β-(2-furylacetamido)-3-methyl-Δ³-0-2-isocephem-4-carboxylic acid |
| 3-furylacetyl chloride | 7β-(3-furylacetamido)-3-methyl-Δ³-0-2-isocephem-4-carboxylic acid |
| 1,2,5-thiadiazole-3-acetyl chloride | 7β-(1,2,5-thiadiazole-3-acetamido)-3-methyl-Δ³-0-2-isocephem-4-carboxylic acid |
| 1-cyclohexenylacetyl chloride | 7β-(1-cyclohexenylacetamido)-3-methyl-Δ³-0-2-isocephem-4-carboxylic acid |
| 1,4-cyclohexadienylacetyl chloride | 7β-(1,4-cyclohexadienylacetamido)-3-methyl-Δ³-0-2-isocephem-4-carboxylic acid |
| 3-(1,4-cyclohexadien-1-yl) propionyl chloride | 7β-[3-(1,4-cyclohexadien-1-yl)-propionamido]-3-methyl-Δ³-0-2-isocephem-4-carboxylic acid |
| isothiazol-4-yl-acetic acid | 7β-(isothiazol-4-yl-acetamido)-3-methyl-Δ³-0-2-isocephem-4-carboxylic acid |
| isothiazol-5-yl-acetic acid | 7β-(isothiazol-5-yl-acetamido)-3-methyl-Δ³-0-2-isocephem-4-carboxylic acid |
| isothiazol-3-yl-acetic acid | 7β-(isothiazol-3-yl-acetamido)-3-methyl-Δ³-0-2-isocephem-4-carboxylic acid |
| 5-phenyl-1,3,4-thiadiazolyl-2- | 7β-)-5-phenyl-1,3,4-thiadiazol-2-yl-acetamido)-3-methyl-Δ³-0-2-isocephem-4-carboxylic acid |
| thiazol-2-yl-acetyl chloride | 7β-(thiazol-2-yl-acetamido)-3-methyl-Δ³-0-2-isocephem-4-carboxylic acid |
| imidazol-2-yl-acetyl chloride | 7β-(imidazol-2-yl-acetamido)-3-methyl-Δ³-0-2-isocephem-4-carboxylic acid |
| 1,2,3-triazol-4-yl-acetic acid | 7β-(1,2,3-triazol-4-yl-acetamido)-3-methyl-Δ³-0-2-isocephem-4-carboxylic acid |
| oxazol-2-yl-acetyl chloride | 7β-oxazol-2-yl-acetamido)-3-methyl-Δ³-0-2-isocephem-4-carboxylic acid |
| 4-pyridylacetyl chloride | 7β-(4-pyridylacetamido)-3-methyl-Δ³-0-2-isocephem-4-carboxylic acid |
| 3-pyridylacetyl chloride | 7β-(3-pyridylacetamido)-3-methyl-Δ³-0-2-isocephem-4-carboxylic acid |
| 3-phenylpropionyl chloride | 7β-(3-phenylpropionamido)-3-methyl-Δ³-0-2-isocephem-4-carboxylic acid |
| 3-(p-chlorophenyl)-propionyl chloride | 7β-[3-(p-chlorophenyl)propionamido]-3-methyl-Δ³-0-2-isocephem-4-carboxylic acid |
| 3-(p-methoxyphenyl)-propionyl chloride | 7β-[3-(p-methoxyphenyl)propionamido]-3-methyl-Δ³-0-2-isocephem-4-carboxylic acid |
| 3-(p-sulfamylphenyl)-propionyl chloride | 7β-[3-(p-sulfamylphenyl)propionamido]-3-methyl-Δ³-0-2-isocephem-4-carboxylic acid |
| 3-(3,4-dimethoxyphenyl)-propionyl chloride | 7β-[3-(3,4-dimethoxyphenyl)-propionamido]-3-methyl-Δ³-0-2-isocephem-4-carboxylic acid |
| 3-(p-hydroxyphenyl)-propionic acid | 7β-[3-(p-hydroxyphenyl)propion-amido]-3-methyl-Δ³-0-2-isocephem-4-carboxylic acid |
| 3-(p-nitrophenyl)propionic acid | 7β-[3-(p-nitrophenyl)propionamido]-3-methyl-Δ³-0-2-isocephem-4-carboxylic acid |
| 3-(2-thienyl)propionyl chloride | 7β-[3-(2-thienyl)propionamido]-3-methyl-Δ³-0-2-isocephem-4-carboxylic acid |
| 3-(3-thienyl)propionyl chloride | 7β-[3-(3-thienyl)propionamido]-3-methyl-Δ³-0-2-isocephem-4-carboxylic acid |
| cyclohexylacetic acid | 7β-(cyclohexylacetamido)-3-methyl-Δ³-0-2-isocephem-4-carboxylic acid |
| 3-phenyl-5-methylisoxazol-4-yl-acetic acid | 7β-(3-phenyl-5-methylisoxazol-4-yl-acetamido)-3-methyl-Δ³-0-2-isocephem-4-carboxylic acid |
| o-aminomethylphenylacetic acid | 7β-(o-aminomethylphenylacetamido)-3-methyl-Δ³-0-2-isocephem-4-carboxylic acid |

EXAMPLE 43

When the acylating agents listed in Example 42 are reacted according to the general N-acylation procedures of the examples above with 7β-amino-Δ³-0-2-isocephem-4-carboxylic acid, 7β-amino-3-benzyl-Δ³-0-2-isocephem-4-carboxylic acid and 7β-amino-3-phenethyl-Δ³-0-2-isocephem-4-carboxylic acid, respectively, there are produced the corresponding 7β-acylamino-Δ³-0-2-isocephem-4-carboxylic acids, 7β-acylamino-3-Δ³-0-2-isocephem-4-carboxylic acids and 7β-acylamino-3-phenethyl-Δ³-0-2-isocephem-4-carboxylic acids, respectively.

EXAMPLE 44

Repeating the general N-acylation procedures of the examples above to react the following acylating agents with 7β-amino-3-methyl-Δ³-0-2-isocephem-4-carboxylic acid (or an ester or salt thereof), the following products are obtained after removal of any functional blocking groups.

| | |
|---|---|
| p-nitrophenoxyacetyl acid | 7β-(p-nitrophenoxyacetamido)-3-methyl-Δ³-0-2-isocephem-4-carboxylic acid |
| p-fluorophenoxyacetyl acid | 7β-(p-flourophenoxyacetamido)-3-methyl-Δ³-0-2-isocephem-4-carboxylic acid |
| o-chlorophenoxyacetic acid | 7β-(o-chlorophenoxyacetamido)-3-methyl-Δ³-0-2-isocephem-4-carboxylic acid |
| p-sulfamylphenoxyacetic acid | 7β-(p-sulfamylphenoxyacetamido)-3-methyl-Δ³-0-2-isocephem-4-carboxylic acid |
| p-methylphenoxyacetic acid | 7β-(p-methylphenoxyacetamido)-3-methyl-Δ³-0-2-isocephem-4-carboxylic acid |
| 4-hydroxyphenoxyacetic acid | 7β-(4-hydroxyphenoxyacetamido)-3-methyl-Δ³-0-2-isocephem-4-carboxylic acid |
| 2,4-dichlorophenoxyacetic acid | 7β-(2,4-dichlorophenoxyacetamido)-3-methyl-Δ³-0-2-isocephem-4-carboxylic acid |
| 2,6-dimethoxyphenoxy-acetic acid | 7β-(2,6-dimethoxyphenoxyacetamido)-3-methyl-Δ³-0-2-isocephem-4-carboxylic acid |
| 4-cyanophenoxyacetic acid | 7β-(4-cyanophenoxyacetamido)-3-methyl-Δ³-0-2-isocephem-4-carboxylic acid |
| α-phenoxypropionic acid | 7β-(α-phenoxypropionamido)-3-methyl-Δ³-0-2-isocephem-4-carboxylic acid |
| α-(2-chlorophenoxy)-propionic acid | 7β-(α-(2-chlorophenoxy)propion-amido]-3-methyl-Δ³-0-2-isocephem-4-carboxylic acid |
| α-(2,4-dichlorophenoxy)-n-butyric acid | 7β-[α-(2,4-dichlorophenoxy)-n-butyramido]-3-methyl-Δ³-0-2-isocephem-4-carboxylic acid |
| α-phenoxyphenylacetic acid | 7β-(α-phenoxyphenylacetamido)-3-methyl-Δ³-0-2-isocephem-4-carboxylic acid |
| α-phenoxybutyric acid | 7β-(α-phenoxybutyramido)-3-methyl-Δ³-0-2-isocephem- |

| | 4-carboxylic acid |
|---|---|
| 4-trifluoromethylphenoxy-acetic acid | 7β-(4-trifluoromethylphenoxy-acetamido)-3-methyl-Δ³-0-2-isocephem-4-carboxylic acid |
| benzyloxyacetyl chloride | 7β-(benzyloxyacetamido)-3-methyl-Δ³-0-2-isocephem-4-carboxylic acid |
| β-naphthoxyacetyl chloride | 7β-(β-naphthoxyacetamido)-3-methyl-Δ³-0-2-isocephem-4-carboxylic acid |

EXAMPLE 45

Replacement of the 7β-amino-3-methyl-Δ³-0-2-isocephem-4-carboxylic acid of Example 44 with 7β-amino-Δ³-0-2-isocephem-4-carboxylic acid, 7β-amino-3-benzyl-Δ³-0-2-isocephem-4-carboxylic acid and 7β-amino-3-phenethyl-Δ³-0-2-isocephem-4-carboxylic acid (or an ester or salt thereof), respectively, produces the corresponding 7β-acylamino-Δ³-0-2-isocephem-4-carboxylic acids, 7β-acylamino-3-benzyl-Δ³-0-2-isocephem-4-carboxylic acids and 7β-acylamino-3-phenethyl-Δ³-0-2-isocephem-4-carboxylic acids, respectively.

EXAMPLE 46

Following the general N-acylation methods of the preceeding examples, the compounds listed below are prepared by acylating 7β-amino-3-methyl-Δ³-0-2-isocephem-4-carboxylic acid with an acylating acid of the formula

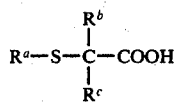

or a functional equivalent, e.g. acid halide, thereof.

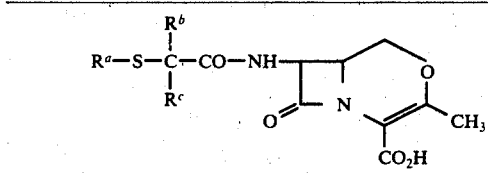

| $R^a$ | $R^b$ | $R^c$ |
|---|---|---|
| Cl—⌬— | H | H |
| ⌬(CF₃)— | H | H |
| Cl,CH₃-⌬— | H | H |
| ⌬(CH₂NH₂)— | H | H |

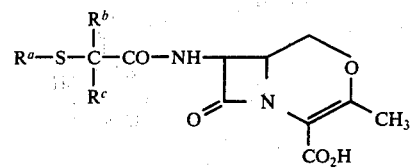

| $R^a$ | $R^b$ | $R^c$ |
|---|---|---|
| H₂NCH₂—⌬— | H | H |
| ⌬— | H | H |
| F—⌬— | H | H |
| 4-pyridyl | H | H |
| 3-pyridyl | H | H |
| ⌬—CH₂— | H | H |
| ⌬(CN)— | H | H |
| imidazolyl (2) | H | H |
| imidazolinyl (2) | H | H |
| thiazolyl (2) | H | H |
| thiazolinyl (2) | H | H |
| triazolyl (2) | H | H |
| 1-methyl-imidazolyl (2) | H | H |
| 2-thienyl | H | H |
| 3-thienyl | H | H |
| n-butyl | H | H |
| isobutyl | H | H |
| 2-acetamido-thiazol-5-yl | H | H |
| 2-phenyl-1,3,4-thiadiazol-5-yl | H | H |
| 2-methyl-1,3,4-oxadiazol-5-yl | H | H |

EXAMPLE 47

Replacement of the 7β-amino-3-methyl-Δ³-0-2-isocephem-4-carboxylic acid of Example 46 with 7β-amino-Δ³-0-2-isocephem-4-carboxylic acid, 7β-amino-3-benzyl-Δ³-0-2-isocephem-4-carboxylic acid and 7β-amino-3-phenethyl-Δ³-0-2-isocephem-4-carboxylic acid (or an ester or salt thereof), respectively, produces the corresponding 7β-acylamino-Δ³-0-2-isocephem-4-carboxylic acids, 7β-acylamino-3-benzyl-Δ³-0-2-isocephem-4-carboxylic acids and 7β-acylamino-3-phenethyl-Δ³-0-2-isocephem-4-carboxylic acids, respectively.

EXAMPLE 48

Following the general N-acylation methods of the proceeding examples, the compounds listed below are prepared by acylation of 7β-amino-3-methyl-Δ³-0-2-isocephem-4-carboxylic acid with the appropriate acylating acid of the general formula $R^a$-COOH or a functional equivalent thereof.

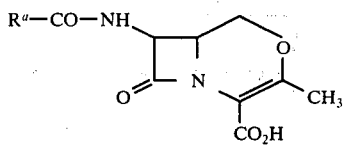

7β-(3-phenyl-5-methyl-isoxazol-4-ylcarboxamido)-3-methyl-Δ³-0-2-isocephem-4-carboxylic acid;
7β-[3-(2,6-dichlorophenyl)-5-methylisoxazol-4-ylcarboxamido]-3-methyl-Δ³-0-2-isocephem-4-carboxylic acid;
7β-(2,6-dichlorobenzamido)-3-methyl-Δ³-0-2-isocephem-4-carboxylic acid;
7β-(2-phenylbenzamido)-3-methyl-Δ³-0-2-isocephem-4-carboxylic acid;
7β-(2-aminomethylbenzamido)-3-methyl-Δ³-0-2-isocephem-4-carboxylic acid;
7β-(2-carboxybenzamido)-3-methyl-Δ³-0-2-isocephem-4-carboxylic acid;
7β-(cyclopentanecarboxamido)-3-methyl-Δ³-0-2-isocephem-4-carboxylic acid;
7β-(1-aminocyclohexanecarboxamido)-3-methyl-Δ³-0-2-isocephem-4-carboxylic acid;
7β-(cyclohexanecarboxamido)-3-methyl-Δ³-0-2-isocephem-4-carboxylic acid;
7β-(1,4-cyclohexadienylcarboxamido)-3-methyl-Δ³-0-2-isocephem-4-carboxylic acid;
7β-(4-nitrobenzamido)-3-methyl-Δ³-0-2-isocephem-4-carboxylic acid;
7β-(4-methylbenzamido)-3-methyl-Δ³-0-2-isocephem-4-carboxylic acid;
7β-(o-methoxybenzamido)-3-methyl-Δ³-0-2-isocephem-4-carboxylic acid;
7β-(o-bromobenzamido)-3-methyl-Δ³-0-2-isocephem-4-carboxylic acid;
7β-(p-ethoxybenzamido)-3-methyl-Δ³-0-2-isocephem-4-carboxylic acid;
7β-(o-acetamidobenzamido)-3-methyl-Δ³-0-2-isocephem-4-carboxylic acid;
7β-(p-allylbenzamido)-3-methyl-Δ³-0-2-isocephem-4-carboxylic acid;
7β-(2,5-dihydroxybenzamido)-3-methyl-Δ³-0-2-isocephem-4-carboxylic acid;
7β-(2-ethoxy-1-naphthamido)-3-methyl-Δ³-0-2-isocephem-4-carboxylic acid;
7β-(2-methoxy-1-naphthamido)-3-methyl-Δ³-0-2-isocephem-4-carboxylic acid;
7β-(o-dimethylaminobenzamido)-3-methyl-Δ³-0-2-isocephem-4-carboxylic acid;
7β-(benzamido)-3-methyl-Δ³-0-2-isocephem-4-carboxylic acid;
7β-(p-chlorobenzamido)-3-methyl-Δ³-0-2-isocephem-4-carboxylic acid;
7β-(2-thienylcarboxamido)-3-methyl-Δ³-0-2-isocephem-4-carboxylic acid;
7β-(3-thienylcarboxamido)-3-methyl-Δ³-0-2-isocephem-4-carboxylic acid;
7β-(2-furylcarboxamido)-3-methyl-Δ³-0-2-isocephem-4-carboxylic acid;
7β-(3-furylcarboxamido)-3-methyl-Δ³-0-2-isocephem-4-carboxylic acid;
7β-(2'-chlorocyclobutanecarboxamido)-3-methyl-Δ³-0-2-isocephem-4-carboxylic acid;
7β-(3'-fluorocyclopentanecarboxamido)-3-methyl-Δ³-0-2-isocephem-4-carboxylic acid;
7β-(3'-methylcyclopentanecarboxamido)-3-methyl-Δ³-0-2-isocephem-4-carboxylic acid;
7β-(3'-methoxycyclopentanecarboxamido)-3-methyl-Δ³-0-2-isocephem-4-carboxylic acid;
7β-(α-naphthamido)-3-methyl-Δ³-0-2-isocephem-4-carboxylic acid;
7β-(β-naphthamido)-3-methyl-Δ³-0-2-isocephem-4-carboxylic acid;
7β-(1-aminocyclopentanecarboxamido)-3-methyl-Δ³-0-2-isocephem-4-carboxylic acid;
7β-(1-aminocycloheptanecarboxamido)-3-methyl-Δ³-0-2-isocephem-4-carboxylic acid;
7β-(1-cyclohexenecarboxamido)-3-methyl-Δ³-0-2-isocephem-4-carboxylic acid.

EXAMPLE 49

Replacement of the 7β-amino-3-methyl-Δ³-0-2-isocephem-4-carboxylic acid of Example 48 with 7β-amino-Δ³-0-2-isocephem-4-carboxylic acid, 7β-amino-3-benzyl-Δ³-0-2-isocephem-4-carboxylic acid and 7β-amino-3-phenethyl-Δ³-0-2-isocephem-4-carboxylic acid (or an ester or salt thereof), respectively, produces the corresponding 7β-acylamino-Δ³-0-2-isocephem-4-carboxylic acids, 7β-acylamino-3-benzyl-Δ³-0-2-isocephem-4-carboxylic acids and 7β-acylamino-3-phenethyl-Δ³-0-2-isocephem-4-carboxylic acids, respectively.

EXAMPLE 50

Repeating the general N-acylation procedures of the above examples to react trityl chloride with 7β-amino-3-methyl-Δ³-0-2-isocephem-4-carboxylic acid (or an ester or salt thereof), there is obtained after removal of any carboxylprotecting group, 7β-triphenylmethylcarboxamido-3-methyl-Δ³-0-2-isocephem-4-carboxylic acid.

Replacement of the 7β-amino-3-methyl-Δ³-0-2-isocephem-4-carboxylic acid in the above procedure with 7β-amino-Δ³-0-2-isocephem-4-carboxylic acid, 7β-amino-3-benzyl-Δ³-0-2-isocephem-4-carboxylic acid and 7β-amino-3-phenethyl-Δ³-0-2-isocephem-4-carboxylic acid, respectively, produces 7β-triphenylmethylcarboxamido-Δ³-0-2-isocephem-4-carboxylic acid, 7β-triphenylmethylcarboxamido-3-benzyl-Δ³-0-2-isocephem-4-carboxylic acid and 7β-triphenylmethylcarboxamido-3-phenethyl-Δ³-0-2-isocephem-4-carboxylic acid, respectively.

EXAMPLE 51

Following the acylation methods of the preceeding examples and in particular those disclosed in U.S. Pat. No. 3,546,219, the compounds listed below are prepared by reacting 7β-amino-3-methyl-Δ³-0-2-isocephem-4-carboxylic acid (or an ester or salt thereof), with the appropriate acylating agent.

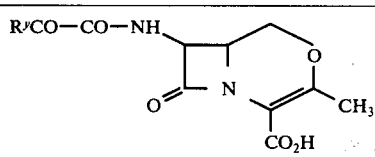

R^y phenyl p-acetamidophenyl p-methoxyphenyl p-methylphenyl

145

-continued $$R^y CO-CO-NH \diagdown \diagup O \diagdown \diagup N \diagdown \diagup CH_3 \diagdown CO_2H$$

| $R^y$ |
|---|
| 2-methoxy-5-methylphenyl |
| m-chlorophenyl |
| o-nitrophenyl |
| 2,4-dichlorophenyl |
| α-naphthyl |
| 2-phenanthryl |
| p-aminophenyl |
| 2-thienyl |
| p-dimethylaminophenyl |

EXAMPLE 52

Replacement of the 7β-amino-3-methyl-Δ³-0-2-isocephem-4-carboxylic acid of Example 51 with 7β-amino-Δ³-0-2-isocephem-4-carboxylic acid, 7β-amino-3-benzyl-Δ³-0-2-isocephem-4-carboxylic acid and 7β-amino-3-phenethyl-Δ³-0-2-isocephem-4-carboxylic acid (or an ester or salt thereof), respectively, produces the corresponding 7β-acylamino-Δ³-0-2-isocephem-4-carboxylic acids, 7β-acylamino-3-benzyl-Δ³-0-2-isocephem-4-carboxylic acids and 7β-acylamino-3-phenethyl-Δ³-0-2-isocephem-4-carboxylic acids, respectively.

EXAMPLE 53

Following the acylation methods of the preceeding examples and in particular those disclosed in U.K. Patent Nos. 1,296,081 and 1,294,541, the compounds listed below are prepared by reacting 7β-amino-3-methyl-Δ³-0-2-isocephem-4-carboxylic acid or an ester or salt thereof with an acylating agent of the formula $$R^a-CH-COOH$$
$$| $$
$$NH$$
$$| $$
$$X=C$$
$$| $$
$$H-N-C-R^i$$
$$\| $$
$$X'$$

or a functional equivalent thereof.

$$R^a-CH-CONH \diagdown \diagup O \diagdown \diagup N \diagdown \diagup CH_3 \diagdown CO_2H$$
with NH, X=C, H—N—C—R^i (with X')

| $R^a$ | X | X' | $R^i$ |
|---|---|---|---|
| phenyl | O | imino | NH₂ |
| 2-thienyl | O | imino | NH₂ |
| 3-thienyl | O | imino | NH₂ |
| m-nitrophenyl | O | imino | NH₂ |
| m-aminophenyl | O | imino | NH₂ |
| p-methylphenyl | O | imino | NH₂ |
| p-chlorophenyl | O | imino | NH₂ |
| p-methoxyphenyl | O | imino | NH₂ |
| p-hydroxyphenyl | O | imino | NH₂ |

146

-continued $$R^a-CH-CONH \diagdown \diagup O \diagdown \diagup N \diagdown \diagup CH_3 \diagdown CO_2H$$
with NH, X=C, H—N—C—R^i (with X')

| $R^a$ | X | X' | $R^i$ |
|---|---|---|---|
| p-dimethylaminophenyl | O | imino | NH₂ |
| 3,4-dimethoxyphenyl | O | imino | NH₂ |
| m-methoxyphenyl | O | imino | NH₂ |
| p-acetamidophenyl | O | imino | NH₂ |
| m-hydroxyphenyl | O | imino | NH₂ |
| 3,5-dichloro-4-hydroxyphenyl | O | imino | NH₂ |
| 3-chloro-4-hydroxyphenyl | O | imino | NH₂ |
| phenyl | O | O | 2-furyl |
| 2-thienyl | O | O | 2-furyl |
| 3-thienyl | O | O | 2-furyl |
| phenyl | O | O | phenyl |
| 2-thienyl | O | O | phenyl |
| phenyl | O | O | 2-thienyl |
| p-chlorophenyl | O | O | 2-furyl |
| p-hydroxypheny | O | O | 2-furyl |
| 3-chloro-4-hydroxyphenyl | O | O | 2-furyl |
| 3,5-dichloro-4-hydroxyphenyl | O | O | 2-furyl |
| m-aminophenyl | O | O | 2-furyl |
| p-methylphenyl | O | O | 2-furyl |
| p-dimethylaminophenyl | O | O | 2-furyl |
| p-ethoxyphenyl | O | O | 2-furyl |
| m-hydroxyphenyl | O | O | 2-furyl |
| p-acetamidophenyl | O | O | 2-furyl |
| m-nitrophenyl | O | O | 2-furyl |
| phenyl | O | O | CH₃ |
| 2-thienyl | O | O | CH₃ |
| 3-thienyl | O | O | CH₃ |
| phenyl | O | O | —CH₂—C₆H₅ |
| phenyl | O | O | (pyridyl) |
| phenyl | O | O | (thiadiazolyl) |
| phenyl | O | O | (isoxazolyl) |
| phenyl | O | O | H₃C-(isoxazolyl)-CH₃ |
| phenyl | O | O | (phenyl-isoxazolyl)-CH₃ |
| phenyl | O | O | (thiazolyl) |
| phenyl | O | O | (methylpyrazinyl) |
| phenyl | O | O | H₃C-(isoxazolyl)-C₆H₅ |
| phenyl | O | O | —CH₂-(2-thienyl) |
| phenyl | S | O | 2-furyl |
| 2-thienyl | S | O | 2-furyl |

-continued

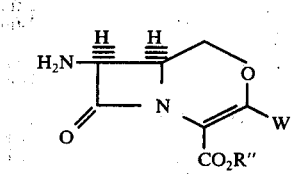

| $R^a$ | X | X' | $R^i$ |
|---|---|---|---|
| 3-thienyl | S | O | 2-furyl |
| p-hydroxyphenyl | S | O | $CH_3$ |
| phenyl | O | imino | phenyl |
| phenyl | O | imino | 2-thienyl |
| phenyl | O | imino | 2-furyl |
| 3-thienyl | O | imino | phenyl |
| phenyl | O | imino | 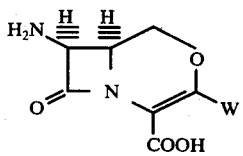 |

We claim:

1. A compound of the formula

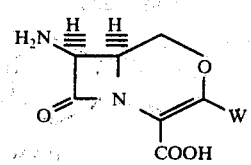

wherein W is benzyl or phenethyl and R" is hydrogen or an easily cleavable ester carboxyl-protecting group selected from the group consisting of benzhydryl, benzyl, p-nitrobenzyl, p-methoxybenzyl, trichloroethyl, trimethylsilyl, phenacyl, acetonyl, (lower)alkyl, triphenylmethyl, methoxymethyl, indanyl, phthalidyl, pivaloyloxymethyl and acetoxymethyl, or a pharmaceutically acceptable salt thereof.

2. An acid of claim 1 having the formula

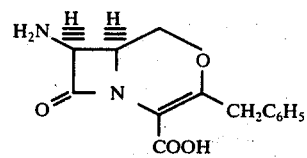

or a pharmaceutically acceptable salt thereof.

3. An acid of claim 1 having the formula

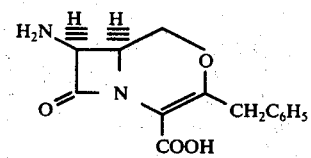

4. A compound of claim 1 wherein R" is pivaloyloxymethyl, methoxymethyl, indanyl, phthalidyl or acetoxymethyl.

5. A compound of claim 1 wherein W is benzyl.

6. The acid of claim 5 having the formula

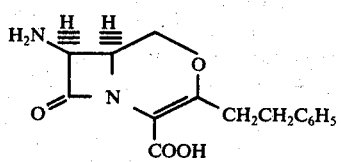

or a pharmaceutically acceptable salt thereof.

7. The acid of claim 5 having the formula

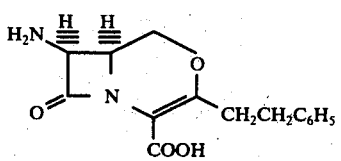

8. A compound of claim 5 wherein R" is pivaloyloxymethyl, methoxymethyl, indanyl, phthalidyl or acetoxymethyl.

9. A compound of claim 1 wherein W is phenethyl.

10. The acid of claim 9 having the formula or a pharmaceutically acceptable salt thereof.

11. The acid of claim 9 having the formula

12. A compound of claim 9 wherein R" is pivaloyloxymethyl, methoxymethyl, indanyl, phthalidyl or acetoxymethyl.

* * * * *